United States Patent [19]

Kocsis et al.

[11] Patent Number: 4,467,101
[45] Date of Patent: Aug. 21, 1984

[54] COMPOUNDS WITH TERMINAL AMINOCARBOXYLIC ACID GROUPING

[75] Inventors: Karoly Kocsis; Peter Schneider, both of Basel; Bruno Fechtig, Reinach; Riccardo Scartazzini, Basel, all of Switzerland

[73] Assignee: Ciba-Geigy Corporation, Ardsley, N.Y.

[21] Appl. No.: 420,534

[22] Filed: Sep. 20, 1982

Related U.S. Application Data

[60] Division of Ser. No. 120,591, Feb. 11, 1980, Pat. No. 4,374,134, which is a continuation of Ser. No. 923,524, Jul. 11, 1978, abandoned.

[30] Foreign Application Priority Data

Jul. 18, 1977 [LU] Luxembourg .............................. 77788

[51] Int. Cl.[3] .................. C07D 333/24; C07C 153/00; C07C 143/52; C07C 147/13
[52] U.S. Cl. ......................................... 549/76; 549/65; 549/72; 549/75; 549/415; 549/478; 549/488; 549/492; 549/493; 549/494; 549/69; 260/455 A; 260/507 R; 560/13; 560/29; 560/30; 560/33; 560/251; 562/430; 562/439; 424/275; 424/285; 424/309; 424/319
[58] Field of Search ....................... 549/65, 72, 75, 76, 549/475, 478, 488, 492, 493, 494, 69; 260/455 A, 507 R; 560/13, 29, 30, 33, 251; 562/430, 439

[56] References Cited

U.S. PATENT DOCUMENTS

3,919,206 11/1975 Patchornik et al. .................. 549/76
3,929,778 12/1975 Brever et al. .......................... 549/26
4,374,134 2/1983 Kocsis et al. ....................... 424/246

Primary Examiner—Alan Siegel
Attorney, Agent, or Firm—Joseph G. Kolodny

[57] ABSTRACT

Acylamido-3-cephem-4-carboxylic acid compounds of the formula

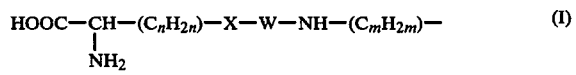

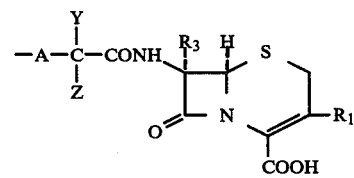

in which
the index n represents an integer of from 1 to 4,
the index m represents 0 or 1,
X represents oxygen, sulphur or an —NH— group,
W represents a —CO—, —CO—NHSO$_2$— or —SO$_2$N-H—CO— group, or
X-W together represent a —CO— or —CO—NH-SO$_2$— group,
A represents optionally substituted phenylene, thienylene or furylene,
Y represents hydrogen, hydroxyl, formyloxy, amino or sulpho optionally present in salt form, and
Z represents hydrogen, or
Y and Z together represent an oxo group or an =N—O—R° group in which R° represents hydrogen or optionally substituted lower alkyl,
R$_1$ represents hydrogen, lower alkyl, lower alkoxy, halogen or a group of the formula —CH$_2$—R$_2$ in which R$_2$ is a free, esterified or etherified hydroxy or mercapto group or a quaternary ammonium group, and
R$_3$ represents hydrogen or methoxy, wherein the carboxyl groups are optionally esterified in a form that can be split under physiological conditions, and the salts thereof, are obtained by liberating the functional group(s) in a starting compound of the formula I in which at least one of the functional groups present is protected.

The compounds are effective in vitro and in vivo against gram-positive and gram-negative bacteria and cocci.

15 Claims, No Drawings

COMPOUNDS WITH TERMINAL AMINOCARBOXYLIC ACID GROUPING

This is a division of application Ser. No. 120,591 filed Feb. 11, 1980, now U.S. Pat. No. 4,374,134, which in turn is a continuation of Ser. No. 923,524, filed July 11, 1978, (now abandoned).

The invention relates to new acylamido-3-cephem-4-carboxylic acid compounds and the salts thereof, processes for their manufacture, pharmaceutical compositions having an antibiotic activity containing these compounds and the therapeutical use thereof for treating infections, as well as to new intermediates and their manufacture.

Numerous 7β-acylamido-3-cephem-4-carboxylic acid compounds which differ in the substituents in the 3-position of the 3-cephem skeleton and in the acyl group at the 7β-amino group are already known. Reviews of such compounds, processes for their manufacture and their antibiotic activity have been published, for example by Edwin H. Flynn, Cephalosporins and Penicillins, Academic Press, New York and London, 1972, J. Cs. Jászberény and T. E. Gunda, Progr. Med. Chem., Vol. 12, 1975, pages 395–477, and Peter G. Sammes, Chemical Reviews, 1976, Vol. 76, No. 1, pages 113–155.

The appearance of new pathogenic bacteria that have become resistant to the antibiotics used hitherto, and the known phenomenon of allergenic reactions, give rise to the need for new, active compounds that exhibit the above disadvantages to a reduced extent or not at all.

The problem underlying the present invention is to produce new 7β-acylamino-3-cephem-4-carboxylic acid compounds that possess novel acyl groups which are characterised by the presence of a terminal α-aminocarboxylic acid grouping. The new compounds are distinguished by an excellent action against normal and resistant bacteria.

The invention also relates to corresponding carboxylic acids containing the novel acyl groups to be used as starting materials, and their reactive functional derivatives in which functional groups are optionally protected, and to processes for the manufacture of these compounds.

The invention relates in particular to acylamido-3-cephem-4-carboxylic acid compounds of the formula

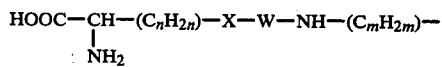

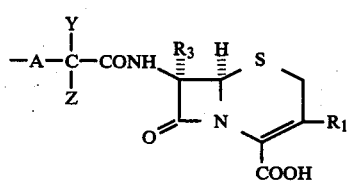

in which
the index n represents an integer of from 1 to 4,
the index m represents 0 or 1,
X represents oxygen, sulphur or an —NH— group,
W represents a —CO—, —CO—NHSO$_2$— or —SO$_2$NH—CO— group, or
X—W together represent a —CO— or —CO—NHSO$_2$— group, A represents optionally substituted phenylene, thienylene or furylene,
Y represents hydrogen, hydroxyl, formyloxy, amino or sulpho optionally present in salt form, and
Z represents hydrogen, or
Y and Z together represent an oxo group or an =N—O—R° group in which R° represents hydrogen or optionally substituted lower alkyl,
R$_1$ represents hydrogen, lower alkyl, lower alkoxy, halogen or a group of the formula —CH$_2$—R$_2$ in which R$_2$ is a free, esterified or etherified hydroxy or mercapto group or a quaternary ammonium group, and
R$_3$ represents hydrogen or methoxy,
wherein functional groups are optionally present in protected form, and to salts of such compounds with acidic and/or basic groups.

The invention relates also to processes for the manufacture of these compounds, pharmaceutical compositions containing such compounds and the therapeutical use thereof.

In the present description of the invention the term "lower" in groups such as lower alkyl, lower alkylene, lower alkoxy, lower alkanoyl and the like means that the corresponding groups, unless expressly defined otherwise, contain up to 7, preferably up to 4, carbon atoms.

A —(C$_n$H$_{2n}$)— group is a branched or unbranched alkylene chain and is especially methylene, 1,2-ethylene, 1,3-propylene or 1,4-butylene, but is also, for example, 1,1-ethylene, 1,1-propylene, 1,2-propylene, 1,1-butylene or 1,1-isobutylene.

An optionally substituted phenyl group A is especially p-phenylene, but may also be o- or m-phenylene. Substituents of the phenylene group are, for example, lower alkyl such as methyl, hydroxy, lower alkoxy such as methoxy, and/or halogen such as fluorine, chlorine or bromine.

An optionally substituted thienylene group A is especially 2,5-thienylene, or also 2,4-thienylene or 2,3-thienylene.

An optionally substituted furylene group A is especially 2,5-furylene, or also 2,4-furylene or 2,3-furylene.

Substituents of the thienylene or furylene group A are, for example, lower alkyl such as methyl, lower alkoxy such as methoxy, and/or halogen such as fluorine, chlorine or bromine.

When Z represents hydrogen, Y is preferably hydrogen or hydroxy, or alternatively amino or sulpho.

In an =N—O—R° group, which is preferably present in the syn-form, an optionally substituted lower alkyl group R° contains 1–4 carbon atoms. Substituents of such a lower alkyl group R° are, for example, lower alkoxy such as methoxy, halogen such as fluorine, chlorine or bromine, hydroxy or acylated hydroxy such as lower alkanoyloxy, for example acetoxy, sulpho and especially free or esterified carboxy.

Representative groups R° are, for example, methyl, ethyl, propyl, butyl, methoxymethyl, methoxyethyl such as 2-methoxyethyl, 3-methoxypropyl, 4-methoxybutyl, 2-haloethyl such as 2-chloroethyl, 3-halopropyl such as 3-chloropropyl, or 4-halobutyl such as 4-chlorobutyl, 2-hydroxyethyl, 3-hydroxypropyl or 4-hydroxybutyl, in which the hydroxy group may be acylated, for example, by lower alkanoyl such as acetyl, 2-sulphoethyl, 3-sulphopropyl, 2-carboxyethyl, 3-carboxypropyl or 4-carboxybutyl, in which the carboxy group may be esterified, for example, by lower alkyl such as methyl or ethyl.

A lower alkyl group $R_1$ contains 1–4 carbon atoms and is, for example, ethyl, propyl, butyl or especially methyl.

A lower alkoxy group $R_1$ contains 1–4 carbon atoms and is, for example, methoxy, ethoxy, propoxy or butoxy.

A halogen $R_1$ is fluorine, bromine, iodine or preferably chlorine.

An esterified hydroxy or mercapto group $R_2$ is esterified by a lower aliphatic carboxylic acid or by an optionally N-substituted carbamic acid.

Hydroxy group $R_2$ esterified by lower aliphatic carboxylic acids are especially lower alkanoyloxy, especially acetoxy, also formyloxy, propionyloxy, valeryloxy, hexanoyloxy, heptanoyloxy or pivaloyloxy.

Mercapto groups $R_2$ esterified by lower aliphatic carboxylic acids are lower alkanoylthio, such as acetylthio, formylthio, propionylthio, valeroylthio, hexanoylthio, heptanoylthio or pivaloylthio.

In a hydroxy or mercapto group $R_2$ esterified by an optionally N-substituted carbamic acid, N-substituents are lower alkyl, optionally substituted by halogen, for example chlorine, or by lower alkanoyl, for example acetyl or propionyl; examples of these N-substituents are methyl, ethyl, 2-chloroethyl or 2-acetoxyethyl. Hydroxy groups $R_2$ esterified in this manner are, for example, carbamoyloxy, N-methylcarbamoyloxy, N-ethylcarbamoyloxy, N-(2-chloroethyl)-carbamoyloxy or N-(2-acetoxyethyl)-carbamoyloxy. Corresponding esterified mercapto groups $R_2$ are, for example, carbamoylthio, N-methylcarbamoylthio, N-ethylcarbamoylthio N-(2-chloroethyl)-carbamoylthio or N-(2-acetoxyethyl)-carbamoylthio.

Etherified hydroxy and mercapto groups $R_2$ are etherified, for example, with an aliphatic hydrocarbon radical, and are especially lower alkoxy, especially having 1–4 carbon atoms, particularly methoxy, as well as ethoxy, n-propoxy or isopropoxy, also straight-chained or branched butoxy, or lower alkylthio, preferably having 1–4 carbon atoms, particularly methylthio, as well as ethylthio, n-propylthio or isopropylthio, and straight-chained or branched butylthio.

Preferred etherified mercapto groups $R_2$ are etherified by an optionally substituted heterocyclic radical that has 1 to 4 ring nitrogen atoms and optionally a further ring hetero atom selected from oxygen and sulphur, and that is bonded by a ring carbon atom to the mercapto group.

Heterocyclic radicals of this type are especially optionally substituted monocyclic, five-membered, diaza-, triaza-, tetraza-, thiaza-, thiadiaza-, thiatriaza-, oxaza- or oxadiazacyclic radicals of aromatic character containing, for example, the substituents mentioned below.

Substituents of such heterocyclyl radicals are, inter alia, lower alkyl, especially methyl, and ethyl, n-propyl, isopropyl or straight-chained or branched butyl; or lower alkyl, substituted by hydroxy, esterified hydroxy such as lower alkanoyloxy, halogen such as chlorine, carboxy, esterified carboxy such as lower alkoxycarbonyl, sulpho, amidated sulpho, amino, mono- or di-lower alkylamino, acylamino such as lower alkanoylamino, or by substituted lower alkanoylamino, for example carboxy- or halogen-substituted lower alkanoylamino; examples of these substituted lower alkyl substituents are 2-hydroxyethyl, 2-acetoxyethyl, 2-chloroethyl, carboxymethyl, 2-carboxyethyl, ethoxycarbonylmethyl, 2-ethoxycarbonylethyl, sulphomethyl, 2-sulphoethyl, sulphamoylmethyl, 2-sulphamoylethyl, 2-aminoethyl, 2-dimethylaminoethyl or 2-acetylaminoethyl. Further substituents of the heterocyclic radical are cycloalkyl, for example cyclopentyl or cyclohexyl; aryl such as phenyl optionally substituted by halogen, for example chlorine, or by nitro; aryl-lower alkyl, for example benzyl, or heterocyclyl such as furyl, for example 2-furyl, thienyl, for example 2-thienyl, or oxazolyl, for example 2- or 5-oxazolyl; or functional groups such as halogen, for example fluorine, chlorine or bromine, optionally substituted amino, such as amino optionally mono- or di-substituted by lower alkyl, for example amino, methylamino or dimethylamino, acylamino, such as lower alkanoylamino or lower alkanoylamino substituted by halogen or carboxy, such as acetylamino, 3-chloropropionylamino or 3-carboxypropionylamino, nitro, hydroxy, lower alkoxy, for example methoxy, ethoxy, n-butoxy or 2-ethylhexyloxy, or optionally functionally modified carboxy, such as carboxy, esterified carboxy, such as lower alkoxycarbonyl, for example methoxycarbonyl or ethoxycarbonyl, optionally substituted carbamoyl, such as N-mono- or N,N-di-lower alkylated carbamoyl, for example N-methylcarbamoyl or N,N-dimethylcarbamoyl, or cyano, as well as oxo or oxido, wherein one or more such substituents, preferably bonded to ring carbon atoms but also, especially lower alkyl and oxido, to ring nitrogen atoms, may be present.

Preferred heterocyclically etherified mercapto groups $R_2$, in which the heterocyclic radical is a corresponding monocyclic, five-membered radical, are, inter alia, imidazolylthio, for example 2-imidazolylthio; triazolylthio optionally substituted by lower alkyl and/or phenyl, for example 1H-1,2,3,-triazol-4-ylthio, 1-methyl-1H-1,2,3-triazol-4-ylthio, 1H-1,2,4-triazol-3-ylthio, 5-methyl-1H-1,2,4-triazol-3-ylthio, 3-methyl-1-phenyl-1H-1,2,4-triazol-5-ylthio, 4,5-dimethyl-4H-1,2,4-triazol-3-ylthio or 4-phenyl-4H-1,2,4-triazol-3-ylthio, especially tetrazolylthio optionally substituted as specified above, for example 1H-tetrazol-5-ylthio, 1-methyl-1H-tetrazol-5-ylthio, 1-carboxymethyl-1H-tetrazol-5-ylthio, 1-(2-carboxyethyl)-1H-tetrazol-5-ylthio, 1-sulphomethyl-1H-tetrazol-5-ylthio, 1-(2-sulphoethyl)-1H-tetrazol-5-ylthio, 1-(2-dimethylaminoethyl)-1H-tetrazol-5-ylthio, 1-phenyl-1H-tetrazol-5-ylthio or 1-(4-chlorophenyl)-1H-tetrazol-5-ylthio; thiazolylthio or isothiazolylthio optionally substituted by lower alkyl or by thienyl, for example 2-thiazolylthio, 4-(2-thienyl)-2-thiazolylthio, 4,5-dimethyl-2-thiazolylthio, 3-isothiazolylthio, 4-isothiazolylthio or 5-isothiazolylthio; especially also thiadiazolylthio optionally substituted as specified above, for example 1,2,3-thiadiazol-4-ylthio, 1,2,3-thiadiazol-5-ylthio, 1,3,4-thiadiazol-2-ylthio, 2-methyl-1,3,4-thiadiazol-5-ylthio, 2-(3-carboxypropionylamino)-1,3,4-thiadiazol-5-ylthio, 1,2,4-thiadiazol-5-ylthio or 1,2,5-thiadiazol-3-ylthio; thiatriazolylthio, for example 1,2,3,4-thiatriazolyl-5-ylthio; oxazolylthio or isoxazolylthio optionally substituted as specified above, for example 5-oxazolylthio, 4-methyl-5-oxazolylthio, 2-oxazolylthio, 4,5-diphenyl-2-oxazolylthio or 3-methyl-5-isoxazolylthio; or oxadiazolylthio optionally substituted as specified above, for example 1,2,4-oxadiazol-5-ylthio, 2-methyl-1,3,4-oxadiazol-5-ylthio, 2-phenyl-1,3,4-oxadiazol-5-ylthio, 5-(4-nitrophenyl)-1,3,4-oxadiazol-2-ylthio or 2-(2-thienyl)-1,3,4-oxadiazol-5-ylthio.

Preferred heterocyclically etherified mercapto groups $R_2$, in which the heterocyclic radical is a corresponding monocyclic, six-membered radical or a corresponding partially saturated radical, are, inter alia 1-oxidopyridylthio optionally substituted by halogen, for example 1-oxido-2-pyridylthio or 4-chloro-1-oxido-2-pyridylthio; pyridazinylthio optionally substituted by hydroxy, for example 3-hydroxy-6-pyridazinylthio; N-oxidopyridazinylthio optionally substituted by lower alkyl, lower alkoxy or halogen, for example 2-oxido-6-pyridazinylthio, 3-chloro-1-oxido-6-pyridazinylthio, 3-methyl-2-oxido-6-pyridazinylthio, 3-methoxy-1-oxido-6-pyridazinylthio, 3-ethoxy-1-oxido-6-pyridazinylthio, 3-n-butoxy-1-oxido-6-pyridazinylthio or 3-(2-ethylhexyloxy)-1-oxido-6-pyridazinylthio; or 2-oxo-1,2-dihydropyrimidinylthio optionally substituted by lower alkyl, amino, di-lower alkylamino or carboxy, for example 2-oxo-1,2-dihydro-4-pyrimidinylthio, 6-methyl-2-oxo-1,2-dihydro-4-pyrimidinylthio, 5-methyl-2-oxo-1,2-dihydro-4-pyrimidinylthio, 6-amino-2-oxo-1,2-dihydro-4-pyrimidinylthio, 6-dimethylamino-2-oxo-1,2-dihydro-4-pyrimidinylthio, 5-carboxy-2-oxo-1,2-dihydro-4-pyridimidinylthio or 6-carboxy-2-oxo-1,2-dihydro-4-pyrimidinylthio.

Quaternary ammonium groups $R_2$ are quaternary ammonium groups derived from tertiary organic bases, preferably from corresponding aliphatic amines or especially from corresponding heterocyclic nitrogen bases, and bonded by the nitrogen atom to the methyl carbon atom.

In a quaternary ammonium group $R_2$ that is derived from a tertiary organic base, the nitrogen atom is bonded to the methyl carbon atom and is accordingly present in the quaternised, positively charged form. Quaternary ammonium groups are, inter alia, tri-lower alkylammonium, for example trimethylammonium, triethylammonium, tripropylammonium or tributylammonium, but especially monocyclic or bicyclic azacyclic ammonium groups of aromatic character having 1 or 2 ring nitrogen and optionally a ring sulphur atom, such as pyrimidinium, pyridazinium, thiazolium, quinolinium and especially pyridinium, optionally mono- or polysubstituted by, for example, lower alkyl such as methyl; hydroxy-lower alkyl such as hydroxymethyl; amino; substituted sulphonamido such as 4-aminophenylsulphonamido; hydroxy; halogen such as fluorine, chlorine, bromine or iodine; halogen-lower alkyl such as trifluoromethyl; sulpho; optionally functionally modified carboxy such as carboxy, lower-alkoxycarbonyl, for example methoxycarbonyl; cyano; carbamoyl optionally N-mono- or N,N-disubstituted by lower alkyl, for example by methyl or ethyl, or by hydroxy-lower alkyl, for example hydroxymethyl, for example carbamoyl, N-methylcarbamoyl or N,N-dimethylcarbamoyl; hydrazinocarbonyl optionally N-substituted by lower alkyl, for example hydrazinocarbonyl; carboxy-lower alkyl such as carboxymethyl; lower alkanoyl such as acetyl; or 1-lower alkylpyrrolidinyl such as 1-methyl-2-pyrrolidinyl.

Heterocyclic ammonium groups $R_2$ are especially pyridinium optionally containing lower alkyl, hydroxy-lower alkyl, amino, substituted sulphonamido, hydroxy, halogen, trifluoromethyl, sulpho, carboxy, lower alkoxycarbonyl, cyano, lower alkanoyl, 1-lower alkylpyrrolidinyl or carbamoyl optionally N-substituted by lower alkyl or hydroxy-lower alkyl, for example pyridinium, 2-, 3- or 4-methylpyridinium, 3,5-dimethylpyridinium, 2,4,6-trimethylpyridinium, 2-, 3- or 4-ethylpyridinium, 2-, 3- or 4-propylpyridinium or especially 4-hydroxymethylpyridinium, also 2-amino- or 2-amino-6-methyl-pyridinium, 2-(4-aminophenylsulphonylamido)-pyridinium, 3-hydroxypyridinium, 3-fluoro-, 3-chloro-, 3-iodo- or especially 3-bromo-pyridinium, 4-trifluoromethylpyridinium, 3-sulphopyridinium, 2-, 3- or 4-carboxy- or 2,3- or 3,4-dicarboxypyridinium, 4-methoxycarbonylpyridinium, 3- or 4-cyanopyridinium, 3-carboxymethylpyridinium, 3- or 4-acetylpyridinium, 3-(1-methyl-2-pyrrolidinyl)-pyridinium, and especially 4-carbamoyl-, 3-carbamoyl-, 3,4-dicarbamoyl-, 3- or 4-N-methylcarbamoyl-, 4-N,N-dimethylcarbamoyl-, 4-N-ethylcarbamoyl-, 3-N,N-diethylcarbamoyl-, 4N-propylcarbamoyl-, 4-isopropylcarbamoyl- and 4-hydroxymethylcarbamoylpyridinium.

The functional groups present in compounds of the formula I, especially carboxyl and amino and also hydroxy and sulpho groups are optionally protected by protective groups that are used in penicillin, cephalosporin and peptide chemistry.

Such protective groups can easily be split off, that is without undesired side reactions occurring, for example under solvolytic, reductive, photolytic or physiological conditions.

Protective groups of this kind and methods of splitting them off are described, for example, in "Protective Groups in Organic Chemistry", Plenum Press, London, New York, 1973 and also in "The Peptides", Vol. I, Schröder and Lübke, Academic Press, London, New York, 1965.

Thus carboxyl groups are, for example, usually protected in esterified form, wherein such ester groupings can readily be split under gentle conditions. Suitable protected carboxyl groups are especially lower alkoxycarbonyl, especially tert.-lower alkoxycarbonyl, for example tert.-butoxycarbonyl; polycycloalkoxycarbonyl, for example adamantyloxycarbonyl; arylmethoxycarbonyl, in which aryl is preferably one or two phenyl radicals optionally mono- or polysubstituted for example by lower alkyl, especially tert.-lower alkyl, for example tert.-butyl, by lower alkoxy such as, methoxy, by hydroxy, halogen, for example chlorine, and/or by nitro, such as benzyloxycarbonyl optionally substituted, for example, as mentioned above, for example 4-nitrobenzyloxycarbonyl, or 4-methoxybenzyloxycarbonyl, or for example diphenylmethoxycarbonyl substituted as mentioned above, for example benzhydryloxycarbonyl or di-(4-methoxyphenyl)-methoxycarbonyl; or 2-halogeno-lower alkoxycarbonyl, for example 2,2,2-trichloroethoxycarbonyl; or especially aroylmethoxycarbonyl, wherein the aroyl group is preferably benzoyl optionally substituted for example by halogen, such as bromine, for example phenacyloxycarbonyl; or polyhalogenoaryloxycarbonyl, such as pentachlorophenyloxycarbonyl. Esterified carboxyl groups are also corresponding silyloxycarbonyl, especially organic silyloxycarbonyl, groups or corresponding stannyloxycarbonyl groups. In these the silicon or tin atom preferably contains lower alkyl, especially methyl, also lower alkoxy, for example methoxy, and/or halogen, for example chlorine, as substituents. Suitable silyl or stannyl protective groups are especially tri-lower alkylsilyl, especially trimethylsilyl, also dimethyl-tert.-butysilyl, lower alkoxy-lower alkylhalogenosilyl, for example methoxymethylchlorosilyl, or di-lower alkylhalogenosilyl, for example dimethylchlorosilyl, or correspondingly substituted stannyl compounds, for example tri-n-butylstannyl, Preferred protected carboxyl groups are especially tert.-butoxycarbonyl, benzyloxycarbonyl optionally substituted for example as mentioned above, for example 4-nitrobenzyloxycarbonyl, or diphenylmethoxycarbonyl, for example benzhydryloxycarbonyl.

An esterified carboxyl group that can be split under physiological conditions is especially an acyloxymethoxycarbonyl group, in which acyl represents, for example, the radical of an organic carboxylic acid, particularly an optionally substituted lower alkanecarboxylic acid, or in which acyloxymethyl forms the radical of a lactone. Groups of this type are lower alkanoyloxymethoxycarbonyl, for example acetoxymethoxycarbonyl or pivaloyloxymethoxycarbonyl, amino-lower alkanoyloxymethoxycarbonyl, especially α-amino-lower alkanoyloxymethoxycarbonyl, for example glycyloxymethoxycarbonyl, L-valyloxymethoxycarbonyl or L-leucyloxymethoxycarbonyl, also phthalidyloxycarbonyl, for example 2-phthalidyloxycarbonyl, or indanyloxycarbonyl, for example 5-indanyloxycarbonyl.

A protected amino group may be present, for example, in the form of a readily cleavable acylamino, triarylmethylamino, etherified mercaptoamino, 1-acyl-2-lower alkylideneamino, silylamino or stannylamino group or in the form of an azido group.

In a corresponding acylamino group, acyl is preferably the acyl radical of a carbonic acid semi-ester, such as lower alkoxycarbonyl, especially tert.-lower alkoxycarbonyl, for example tert.-butoxycarbonyl; polycycloalkoxycarbonyl, for example adamantyloxycarbonyl; arylmethoxycarbonyl, in which aryl is preferably one or two phenyl radicals optionally mono- or polysubstituted for example by lower alkyl, especially tert.-lower alkyl, for example tert.-butyl, by lower alkoxy such as methoxy, by hydroxy, halogen, for example chlorine, and/or by nitro, such as benzyloxycarbonyl optionally substituted, for example as mentioned above, for example 4-nitrobenzyloxycarbonyl, or, for example, diphenylmethoxycarbonyl substituted as mentioned above, for example benzhydryloxycarbonyl or di-(4-methoxyphenyl)-methoxycarbonyl; or 2-halogeno-lower alkoxycarbonyl, for example 2,2,2-trichloroethoxycarbonyl, 2-bromoethoxycarbonyl or 2-iodoethoxycarbonyl, or acyloxymethoxycarbonyl, especially aroylmethoxycarbonyl, in which the aroyl group is preferably benzoyl optionally substituted, for example, by halogen, such as bromine, for example phenacyloxycarbonyl. Acyl in an acylamino group may also represent the corresponding radical of an organic sulphonic acid; such a radical is especially arylsulphonyl, in which aryl represents a phenyl radical optionally substituted, for example by lower alkyl such as methyl, halogen such as bromine, or by nitro, for example 4-methylphenylsulphonyl.

In a triarylmethylamino group the aryl radicals are especially optionally substituted radicals; the triarylmethylamino group is especially trityl.

An etherified mercapto group in an amino group protected with such a radical is especially arylthio or aryl-lower alkylthio, in which aryl is in particular phenyl optionally substituted, for example by lower alkyl, such as methyl or tert-butyl, by lower alkoxy such as methoxy, by halogen such as chlorine, and/or by nitro. A corresponding amino protective group is, for example, 4-nitrophenylthio.

In a 1-acyl-2-lower alkylidene radical that can be used as amino protective group, acyl is preferably the corresponding radical of a lower alkanecarboxylic acid, of a benzoic acid optionally substituted for example by lower alkyl such as methyl or tert.-butyl, by lower alkoxy such as methoxy, by halogen such as chlorine, and/or by nitro, or of a carbonic acid semi-ester such as a carbonic acid lower alkyl semi-ester. Corresponding protective groups are especially 1-lower alkanoyl-2-propylidene, for example 1-acetyl-2-propylidene, or 1-lower alkoxycarbonyl-2-propylidene, for example 1-ethoxycarbonyl-2-propylidene.

A silyl- or stannylamino group is especially an organic silyl- or stannylamino group, in which the silicon or tin atom preferably contains lower alkyl, especially methyl, also lower alkoxy, for example methoxy, and/or halogen, for example chlorine, as substituents. Corresponding silyl or stannyl groups are especially tri-lower alkylsilyl, particularly trimethylsilyl, also dimethyl-tert.-butylsilyl, lower alkoxy-lower alkyl-halogenosilyl, for example methoxymethylchlorosilyl, or di-lower alkylhalogenosilyl, for example dimethylchlorosilyl, or correspondingly substituted stannyl, for example tri-n-butylstannyl.

An amino group can also be protected in protonated form; the anions that come into consideration are especially those of strong inorganic acids, such as hydrohalic acids, for example the chlorine or bromine anion, or of sulphonic acid, such as p-toluenesulphonic acid.

Preferred amino protective groups are the acyl radicals of carbonic acid semi-esters, especially tert.-lower alkoxycarbonyl, diphenylmethoxycarbonyl or benzyloxycarbonyl optionally substituted, for example, as specified above, or 2-halogeno-lower alkoxycarbonyl, such as 2,2,2-trichloroethoxycarbonyl.

Hydroxy protective groups are, for example, acyl radicals, such as 2,2-dichloroacetyl or especially one of the acyl radicals of carbonic acid semi-esters mentioned in connection with a protected amino group, particularly 2,2,2-trichloroethoxycarbonyl, or organic silyl or stannyl radicals, also 2-oxa- or 2-thia-aliphatic or 2-oxa- or 2-thia-cycloaliphatic hydrocarbon radicals that can easily be split off, especially 1-lower alkoxy-lower alkyl or 1-lower alkylthio-lower alkyl, for example 1-methoxyethyl, 1-ethoxyethyl, 1-methylthioethyl or 1-ethylthioethyl, or 2-oxa- or 2-thiacyclo-lower alkyl having 5–7 ring atoms, for example 2-tetrahydrofuryl or 2-tetrahydropyranyl or corresponding thia analogues, as well as optionally substituted α-phenyl-lower alkyl radicals that can easily be split off, such as optionally substituted benzyl or diphenylmethyl, wherein the substituents of the phenyl radicals are, for example, halogen such as chlorine, lower alkoxy such as methoxy and/or nitro.

A protected sulpho group is especially a sulpho group esterified with an aliphatic, cycloaliphatic, cycloaliphatic-aliphatic, aromatic or araliphatic alcohol, such as a lower alkanol, or with a silyl or stannyl radical, such as tri-lower alkylsilyl. In a sulpho group the hydroxy group may be etherified for example like the hyroxy group in an esterified carboxy group.

Salts are especially those of compounds of the formula I having a free carboxyl group, especially metal or ammonium salts, such as alkali metal and alkaline earth metal salts, for example sodium, potassium, magnesium or calcium salts, as well as ammonium salts with ammonia or suitable organic amines, wherein especially aliphatic, cycloaliphatic, cycloaliphatic-aliphatic or araliphatic primary, secondary or tertiary mono-, di- or polyamines, as well as heterocyclic bases are suitable for the salt formation, such as lower alkylamines, for example triethylamine, hydroxy-lower alkylamines, for example 2-hydroxyethylamine, bis-(2-hydroxyethyl)amine or tris-(2-hydroxyethyl)-amine, basic aliphatic esters of carboxylic acids, for example 4-aminobenzoic acid 2-diethylaminoethyl ester, lower alkyleneaminea, for example 1-ethylpiperidine, cycloalkylamines, for example dicyclohexylamine, or benzylamines, for example N,N'-dibenzylethylenediamine, also bases of the pyridine type, for example pyridine, collidine or quinoline. Compounds of the formula I with a basic group can form acid addition salts, for example with inorganic acids, such as hydrochloric acid, sulphuric acid or phosphoric acid, or with suitable organic carboxylic or sulphonic acids, for example trifluoroacetic acid, and with amino acids, such as arginine and lysine. Compounds of the formula I with a free carboxyl group and free amino group may also be present in the form of inner salts, that is, in the form of zwitter ions.

The acyl radical at the 7β-amino group contains one or optionally two centres of asymmetry. The centre of asymmetry next to the 7-amino group that is optionally present, namely when Y represents hydroxyl, amino or sulpho and Z represents hydrogen, is in the R,S- or preferably in the R-configuration. The centre of asymmetry at the terminal amino-carboxylic acid grouping may possess the R-, S- or R,S-configuration.

The compounds of the formula I in which carboxyl groups are optionally esterified in a form that can be split under physiological conditions, and the pharmaceutically acceptable, non-toxic salts thereof are valuable antibiotically active substances that can be used in particular as antibacterial antibiotics. For example, they are effective in vitro against gram-positive and gram-negative bacteria, such as against cocci, including types of Neisseria, and anaerobes in minimum concentrations of approximately 0.02 mcg/ml, and against enterobacteria in minimum concentrations of approximately 0.25 mcg/ml. In vivo in the case of subcutaneous application to a mouse, they are effective, for example, against gram-positive cocci, such as *Staphylococcus aureus* (in minimum doses of approximately 3 mg/kg) and *Streptococcus pneumoniae* (in minimum doses of approximately 0.15 mg/kg), against enterobacteria, such as *Escherichia coli* (in minimum doses of approximately 8 mg/kg), *Klebsiella pneumoniae* and *Proteus mirabilis* (in minimum doses of approximately 0.3 mg/kg), and against other gram-negative bacteria, such as *Pasteurella multocida* (in minimum doses of 0.1 mg/kg). The new compounds can therefore be used in corresponding manner, for example in the form of antibiotically active preparations, for treating infections caused by gram-positive or gram-negative bacteria and cocci, especially for infections caused by enterobacteria, such as *Escherichia coli, Klebsiella pneumoniae* and *Proteus mirabilis.*

Compounds of the formula I in which the functional groups are protected are used as starting materials for the production of compounds of the formula I.

The present invention relates especially to those compounds of the formula I in which the —$(C_nH_{2n})$— group is unbranched and the indices n and m have the meaning given above, X represents oxygen or an —NH— group, W represents a —CO— or —CO—NHSO$_2$— group, or X—W together represent a —CO— or —CO—NHSO$_2$— group, A represents p- or m-phenylene, 2,5-thienylene or 2,5-furylene, Y represents hydrogen, hydroxyl, amino or sulpho and Z represents hydrogen, or Y and Z together represent an =N—O—R° group, in which R° is hydrogen or methyl, R$_1$ represents lower alkyl, lower alkoxy, halogen or a group of the formula —CH$_2$—R$_2$, in which R$_2$ represents lower alkanoyloxy, carbamoyloxy, N-lower alkylcarbamoyloxy, triazolylthio, tetrazolylthio, thiazolylthio, thiatriazolylthio, thiadiazolylthio, oxazolylthio, oxadiazolylthio or pyridino, wherein the heterocyclic rings may optionally be substituted for example by lower alkyl, N,N-di-lower alkylamino-lower alkyl, carboxy-lower alkyl, amino, carboxy-lower alkanoylamino or carbamoyl, and R$_3$ represents hydrogen or methoxy, to pharmaceutically acceptable salts of such compounds, as well as the starting materials and intermediates that can be used for the manufacture thereof.

Particular mention is given to compounds of the formula I in which the —$(C_nH_{2n})$— group is unbranched and the indices n and m have the meaning given, X represents oxygen or an —NH— group, W represents a —CO— or —CO—NHSO$_2$— group, or X—W together represent a —CO— or —CO—NHSO$_2$— group, A represents p- or m-phenylene or, when m is 1, also 2,5-thienylene or 2,5-furylene, Y represents hydrogen, hydroxyl, amino or sulpho and Z represents hydrogen, or Y and Z together represent an =N—O—R° group, in which R° is hydrogen or methyl, R$_1$ represents methyl, methoxy, or a group of the formula —CH$_2$—R$_2$, in which R$_2$ represents acetoxy, carbamoyloxy, tetrazolylthio, especially 1-methyl-1H-tetrazol-5-ylthio, 1-sulphomethyl-1H-tetrazol-5-ylthio, 1-carboxymethyl-1H-tetrazol-5-ylthio or 1-(2-dimethylaminoethyl)-1H-tetrazol-5-ylthio, or thiadiazolylthio, especially 2-methyl-1,3,4-thiadiazol-5-ylthio, or carbamoylpyridinio, especially 4-carbamoylpyridinio, and R$_3$ represents hydrogen or methoxy, pharmaceutically acceptable salts of such compounds, as well as the starting materials and intermediates that can be used for the manufacture thereof.

The invention relates in particular to the compounds of the formula I described in the Examples, the pharmaceutically tolerable salts thereof, and the starting materials and intermediates described therein.

The compounds of the present invention are obtained according to methods known per se.

Compounds of the formula I, in which the carboxyl groups are optionally esterified in a form that can be split under physiological conditions, and the salts thereof, are produced by liberating the functional group(s) in a starting compound corresponding to the formula I in which at least one of the functional groups present is protected, if desired, in a compound obtained, converting a group R$_1$ into a different group R$_1$ and/or, if desired, converting a free carboxyl group into an esterified carboxyl group that can be split under physiological conditions, and/or, if desired, separating an isomeric mixture obtained into the individual isomers, and/or, if desired, converting a compound obtained into a salt or a salt obtained into a free compound or into a different salt.

In the starting compounds of the formula I in which functional groups are protected, those, for example, protected carboxyl, amino, hydroxy, mercapto and/or sulpho groups are optionally liberated in stages or simultaneously in a manner known per se, for example by means of solvolysis, especially hydrolysis, alcoholysis or acidolysis, or by means of reduction, especially hydrogenolysis or chemical reduction.

Thus, for example, a tert.-lower alkoxycarbonyl, polycycloalkoxycarbonyl or diphenylmethoxycarbonyl group can be converted into the free carboxyl group by treating with a suitable acid agent, such as formic acid or trifluoroacetic acid, optionally with the addition of a nucleophilic compound, such as phenol or anisole. An optionally substituted benzyloxycarbonyl group can be liberated, for example, by means of hydrogenolysis by treating with hydrogen in the presence of a hydrogenation catalyst, such as a palladium catalyst. Also certain substituted benzyloxycarbonyl groups such as 4-nitrobenzyloxycarbonyl, may be converted into the free carboxyl group also by means of chemical reduction, for example by treating with an alkali metal dithionite, for example sodium dithionite, or with a reducing metal, for example zinc, or metal salt, such as chromium(II) salt, for example chromium(II) chloride, usually in the presence of a hydrogen-yielding agent that together with the metal is capable of producing nascent hydrogen, such as an acid, especially acetic acid, as well as formic acid, or an alcohol, water preferably being added. By treating with a reducing metal or metal salt, as described above, it is also possible to convert a 2-halogeno-lower alkoxycarbonyl group (optionally after conversion of a 2-bromo-lower alkoxycarbonyl group into a 2-iodo-lower alkoxycarbonyl group) or an acylmethoxycarbonyl group into the free carboxyl group, wherein an aroylmethoxycarbonyl group can likewise be split by treating with a nucleophilic, preferably salt-forming reagent, such as sodium thiophenolate or sodium iodide. A polyhalogenoaryloxycarbonyl group, such as the pentachlorophenyloxycarbonyl group, is hydrolysed to form the free carboxyl group under mild basic conditions, such as by means of dilute sodium hydroxide solution or organic bases in the presence of water. A carboxyl group protected, for example, by silylation or stannylation, can be liberated in the usual manner, for example by treating with water or an alcohol.

A protected amino group is liberated in a manner known per se and, depending on the nature of the protective group, in a variety of manners, for example, by means of solvolysis or reduction. A 2-halogeno-lower alkoxycarbonylamino group (optionally after conversion of a 2-bromo-lower alkoxycarbonyl group into a 2-iodo-lower alkoxycarbonyl group), an acylmethoxycarbonylamino group or a 4-nitrobenzyloxycarbonylamino group can be liberated, for example, by treating with a suitable chemical reducing agent, such as zinc in the presence of aqueous acetic acid; an aroylmethoxycarbonylamino group also may be liberated by treating with a nucleophilic, preferably salt-forming reagent, such as sodium thiophenolate, and a 4-nitrobenzyloxycarbonylamino group also by treating with an alkali metal dithionite, for example sodium dithionite; a diphenylmethoxycarbonylamino group, tert.-lower alkoxycarbonylamino group or polycycloalkoxycarbonylamino group can be liberated by treating, for example, with formic or trifluoroacetic acid; an optionally substituted benzyloxycarbonylamino group may be liberated, for example, by means of hydrogenolysis by treating with hydrogen in the presence of a hydrogenation catalyst, such as a palladium catalyst; an aryl- or aryl-lower alkylthioamino group can be liberated, for example, by treating with a nucleophilic reagent, such as sulphurous acid; an arylsulphonylamino group can be liberated, for example, by means of electrolytic reduction; a 1-acyl-2-lower alkylideneamino group or a triarylmethyl group, for example, by treating with aqueous mineral acid, and an amino group protected with an organic silyl or stannyl group, for example, by means of hydrolysis or alcoholysis.

An amino group protected in the form of an azido group is converted into the free amino group in a manner known per se by reduction, for example by catalytic hydrogenation with hydrogen and a hydrogenation catalyst, such as platinum oxide, palladium, or also Raney nickel, or also by zinc and acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately 20° to 25°, or alternatively at reduced or elevated temperature.

A hydroxy group protected by an acyl group, a silyl or stannyl group or by an optionally substituted α-phenyl-lower alkyl radical is liberated in the same manner as a correspondingly protected amino group. A hydroxy group protected by 2,2-dichloroacetyl is liberated by basic hydrolysis and a hydroxy group protected by a 2-oxa- or 2-thia-aliphatic or -cyclo-aliphatic hydrocarbon radical is liberated by acidolysis.

A protected sulpho group is liberated analogously to the manner in which a protected carboxyl group is liberated.

Preferably the protective groups are so selected that they can all be split off simultaneously, for example by acidolysis, such as by treating with trifluoroacetic acid or formic acid, or by reduction, such as by treating with zinc and glacial acetic acid, or with hydrogen and a hydrogenation catalyst, such as a palladium/carbon catalyst.

The splitting reactions described are carried out under conditions known per se, if necessary while cooling or heating, in a closed vessel and/or in an inert gas atmosphere, for example a nitrogen atmosphere.

In a compound of the formula I in which an amino group, if necessary, is protected, and in which the carboxyl group is present in the 4-position of the cephem ring in free form, in a manner known per se a group $R_1$ can be replaced by a different radical $R_1$ or converted into a different radical $R_1$. It is thus possible, for example, in a compound of the formula I in which $R_1$ represents a group of the formula —$CH_2$—$R_2$ and $R_2$ represents, for example, a radical that can be replaced by nucleophilic substituents, or in a salt thereof, to replace such a radical $R_2$ by an etherified or esterified mercapto group $R_2$ by treating with a corresponding mercaptan or with a thiocarboxylic acid compound. A suitable radical that can be replaced by an etherified mercapto group is, for example, a hydroxy group esterified by a lower aliphatic carboxylic acid. Esterified hydroxy groups of this type are especially acetoxy, and also formyloxy.

The reaction of such a compound with a suitable mercaptan compound can be carried out under neutral or weakly basic conditions in the presence of water and optionally a water-miscible organic solvent. The basic conditions may be established, for example, by the addition of an inorganic base, such as an alkali metal or alkaline earth metal hydroxide, -carbonate or -bicarbonate, for example sodium-, potassium- or calcium hydroxide, -carbonate or -bicarbonate. As organic solvents it is possible to use, for example, water-miscible alcohols, for example lower alkanols such as methanol or ethanol, ketones, for example lower alkanones such as acetone, amides, for example lower alkanecarboxylic acid amides such as dimethylformamide, or nitriles, for example lower alkanoic acid nitriles such as acetonitrile, and the like.

Esterified hydroxy groups $R_2$ in a compound of the formula I, in which $R_1$ represents the —$CH_2$—$R_2$ group, wherein $R_2$ represents a hydroxy group esterified by the acyl radical of an optionally substituted semi-amide of the carbonic acid, may be introduced, for example, by reacting a corresponding compound of the formula I, in which $R_2$ represents free hydroxy (which can be liberated for example, by splitting off the acetyl radical from an acetoxy group $R_2$, for example by hydrolysis in weakly basic medium, such as with an aqueous sodium hydroxide solution at a pH of 9–10, or by treating with a suitable esterase, such as a corresponding enzyme from *Rhizobium tritolii, Rhizobium lupinii, Rhizobium japonicum* or *Bacillus subtilis,* or a suitable citrus esterase, for example from orange peel) with a suitable carbonic acid derivative, especially with an isocyanate or carbamic acid compound, such as a silyl isocyanate, for example silyl tetraisocyanate, a sulphonyl isocyanate, for example chlorosulphonyl isocyanate, or carbamic acid halide, for example chloride (which results in N-unsubstituted 3-aminocarbonyloxymethyl compounds), or also with an N-substituted isocyanate- or with an N-mono-or N,N-disubstituted carbamic acid compound, such as a corresponding carbamic acid halide, for example, chloride, the reaction usually being carried out in the presence of a solvent or diluent and, if necessary, while cooling or heating, in a closed vessel and/or in an inert gas atmosphere, for example a nitrogen atmosphere.

Further, a compound of the formula I in which $R_1$ represents a $-CH_2-R_2$ group, wherein $R_2$ represents, for example, the above-defined radical that can be replaced by nucleophilic substitution, may be reacted with a tertiary organic base, especially an optionally substituted pyridine, under neutral or weakly acidic conditions, preferably at a pH value of approximately 6.5 in the presence of water and optionally in a water-miscible, organic solvent, and thus compounds of the formula I obtained in which $R_1$ represents the radical of the formula $-CH_2-R_2$ and $R_2$ represents a quaternary ammonium group. The weakly acidic conditions can be established by the addition of a suitable organic or inorganic acid, for example acetic acid, hydrochloric acid, phosphoric acid or sulphuric acid. The organic solvents that may be used are, for example, the above-mentioned water-miscible solvents. To increase the yield certain salts may be added to the reaction mixture, for example, alkali metal salts, such as sodium and especially potassium salts, of inorganic acids such as hydrohalic acids, for example hydrochloric and especially hydroiodic acid, and of thiocyanic acid, or organic acids such as lower alkanecarboxylic acids, for example acetic acid. Examples of such salts are potassium iodide and potassium thiocyanate. It is also possible to use for this purpose salts of suitable anion exchangers, for example liquid ion exchangers in salt form, such as, for example, Amberlite LA-1 (liquid secondary amines having a molecular weight of 351–393; oil-soluble and water-insoluble; m eq./g=2.5–2.7, for example in acetate form), with acids, for example acetic acid.

Quaternary ammonium groups $R_2$ can advantageously be produced using an intermediate of the formula I in which $R_2$ represents a substituted carbonylthio group, especially an aromatically substituted carbonylthio group, and in particular the benzoylthio group. Such an intermediate, which can be obtained, for example, by reacting a compound of the formula I in which $R_2$ in the radical $R_1$ represents an esterified hydroxy group, especially a lower alkanoyloxy, for example acetoxy group, with a suitable salt, such as an alkali metal salt, for example a sodium salt, of a thiocarboxylic acid, such as an aromatic thiocarboxylic acid, for example thiobenzoic acid, is reacted with the tertiary amine, especially a tertiary heterocyclic base such as an optionally substituted pyridine, the quaternary ammonium compound being obtained. The reaction is usually carried out in the presence of a suitable desulphurisation agent, especially a mercury salt, for example mercury(II) perchlorate, and of a suitable solvent or diluent or a mixture thereof, if necessary while cooling or heating, in a closed vessel and/or in an inert gas atmosphere, for example a nitrogen atmosphere.

The conversion of a free carboxyl group in a compound of the formula I obtained into an esterified carboxyl group, which can be split under physiological conditions, is carried out according to esterification methods that are known per se, for example by esterifying a compound of the formula I in which further functional groups, such as amino, hydroxy or sulpho groups, are optionally present in protected form, or a functional derivative thereof reactive with respect to the carboxyl group to be esterified, or a salt thereof, with a corresponding alcohol or a reactive functional derivative thereof.

Salts of compounds of the formula I can be produced in a manner known per se. Thus salts of compounds of the formula I having acid groups, can be formed, for example, by treating with metal compounds, such as alkali metal salts of suitable carboxylic acids, for example the sodium salt of α-ethylcaproic acid or sodium bicarbonate, or with ammonia or a suitable organic amine, stoichiometric amounts or only a small excess of the salt-forming agent preferably being used. Acid addition salts of compounds of the formula I are obtained in the usual manner, for example by treating with an acid or a suitable anion exchange reagent. Inner salts of compounds of the formula I that contain a free carboxyl group can be formed, for example, by neutralising salts, such as acid addition salts, to the isoelectric point, for example with weak bases, or by treating with liquid ion exchangers.

Salts can be converted into the free compounds in usual manner; metal and ammonium salts can be converted, for example, by treating with suitable acids, and acid addition salts, for example, by treating with a suitable basic agent.

The process comprises also those embodiments according to which compounds produced as intermediates are used as starting materials and the remaining process steps are carried out with these, or the process is interrupted at any stage; also starting materials in the form of derivatives can be used or formed during the reaction.

Preferably such starting materials are used and the reaction conditions so selected that the compounds listed hereinbefore as being particularly preferred are obtained.

The present invention also relates to starting materials of the formula I, in which at least one of the functional groups is present in protected form, and to processes for the manufacture thereof. These compounds can be produced in a manner known per se for example.

(a) by acylating the amino group in a compound of the formula

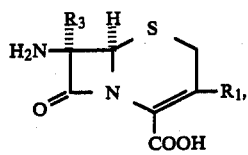

(II)

in which the amino group is optionally substituted by a group allowing acylation, and in which the 4-carboxyl group and further functional groups optionally present in the radical R₁ may be present in protected form, by treating with an acid of the formula

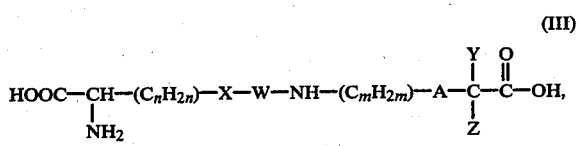

(III)

in which the aminocarboxylic acid grouping HOOC—CH(NH₂)— and further functional groups optionally present in the grouping —A—C(Y)(Z)— are present in protected form, or with a reactive functional acid derivative or a salt thereof, or (b) by acylating the amino group in a compound of the formula

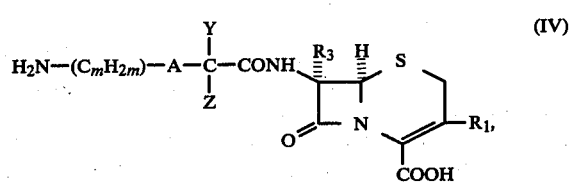

(IV)

in which the amino group may optionally be substituted by a group allowing acylation, and in which the 4-carboxyl group and further functional groups optionally present in the R₁ radical and in the —A—C(Y)(Z)— grouping may be present in protected form, by treating with a reactive functional derivative of an acid of the formula

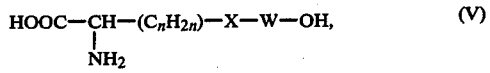

(V)

in which the aminocarboxylic acid grouping HOOC—CH(NH₂)— is present in protected form, or when X—W together represent a —CO— group, also with a corresponding free acid or with a salt thereof, or (c) by acylating the —X—H group in a compound of the formula

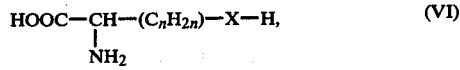

(VI)

in which X represents oxygen, sulphur, or an —NH— group, and in which the aminocarboxylic acid grouping HOOC—CH(NH₂)— is present in protected form, with a reactive functional derivative of a compound of the formula

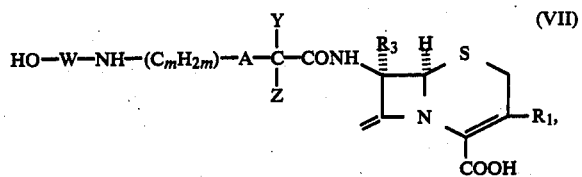

(VII)

in which the 4-carboxyl group and functional groups optionally present in the radical R₁ and in the grouping —A—C(Y)(Z)— may be present in protected form, and, if desired, in a compound obtained protecting still unprotected functional groups or exchanging one protective group for another, and/or, if desired, exchanging a group R₂ in a radical R₁ for another group R₂, and/or, if desired, converting a compound obtained in which R₃ is hydrogen into a compound in which R₃ is methoxy, and/or, if necessary, isomerising an obtained 2-cephem compound or an obtained mixture of a 2-cephem and 3-cephem compound to form the 3-cephem compound, and/or, if desired, separating an obtained isomeric mixture into the individual isomers.

Radicals, substituting the amino group and allowing its acylation, optionally present in a starting material of the formula II or IV are, for example, organic silyl or stannyl groups, also ylidene groups, which together with the amino group form a Schiff's base. The mentioned organic silyl or stannyl groups are, for example, the same as those that are also capable of forming a protected carboxyl group with the 4-carboxyl group on the cephem ring. It is possible in the silylation or stannylation of a carboxyl group in a starting material of the formula II or IV, by using an excess of the silylation or stannylation agent, for the amino group likewise to be silylated or stannylated.

The mentioned ylidene groups are especially arylmethylene groups, wherein aryl represents in particular a carbocyclic, especially monocyclic aryl radical, for example, phenyl optionally substituted, for example, by nitro or hydroxy: such arylmethylene groups are, for example, benzylidene, 2-hydroxybenzylidene or 4-nitrobenzylidene, also oxacycloalkylidene optionally substituted, for example, by carboxy, for example 3-carboxy-2-oxacyclohexylidene.

The remaining functional groups present in the starting materials of the formulae II to VII can be protected by the protective groups already mentioned under the compounds of the formula I. Preferably all the reactive functional groups not taking part in the acylation reaction, but especially acylatable amino, hydroxy and mercapto groups optionally present, are protected.

If a free acid of the formula III or V, in which all the functional groups apart from the reacting carboxyl group are protected, is used for acylation, then normally suitable condensation agents are used, such as carbodiimides, for example N,N'-diethyl-, N,N'-dipropyl-, N,N'-diisopropyl-, N,N'-dicyclohexyl- or N-ethyl-N'-3-dimethylaminopropyl carbodiimide, suitable carbonyl compounds, for example carbonyl diimidazole, or isoxazolinium salts, for example N-ethyl-5-phenylisoxazolinium-3'-sulphonate and N-tert.-butyl-5-methylisoxazolinium perchlorate, or an acylamino compound, for example 2-ethoxy-1-ethoxycarbonyl-1,2-dihydroquinoline.

The condensation reaction is preferably carried out in an anhydrous reaction medium, preferably in the presence of a solvent or diluent, for example methylene chloride, dimethylformamide, acetonitrile or tetrahydrofuran, if desired or necessary while cooling or heating and/or in an inert gas atmosphere.

A reactive, that is to say amide-forming or ester-forming, functional derivative of an acid of the formula III, V or VII, in which all the functional groups apart from the reacting acid group are or can be protected, is especially an anhydride of such an acid, including, and preferably, a mixed anhydride, but also an inner anhydride, that is a corresponding ketene or, in the acid V, when W is the —$SO_2NH$—CO— group, or when X is the —NH— group and W is the —CO— or —CO—$NHSO_2$— group, a corresponding isocyanate. Mixed anhydrides are, for example, those with inorganic acids, such as hydrohalic acids, that is the corresponding acid halides, for example chlorides or bromides, also with hydrazoic acid, that is the corresponding acid azides, with a phosphorus-containing acid, for example phosphoric acid or phosphorous acid, or with a sulphur-containing acid, for example sulphuric acid, or with hydrocyanic acid. Further mixed anhydrides are, for example, those with organic carboxylic acids, such as with lower alkanecarboxylic acids optionally substituted, for example, by halogen, such as fluorine or chlorine, for example pivalic acid or trichloroacetic acid, or with semi-esters, especially lower alkyl semi-esters of carbonic acid, such as the ethyl or isobutyl semi-ester of carbonic acid, or with organic, especially aliphatic or aromatic, sulphonic acids, for example p-toluenesulphonic acid. A mixed inner anhydride of the acid III with the carbonic acid semi-ester of the α-hydroxy group can also be used when Z is hydrogen and Y is hydroxy.

Further acid derivatives suitable for the reaction with the amino, hydroxy or mercapto group, in an acid of the formula III, V or VII, in which all functional groups apart from the reacting carboxyl group are protected or can be protected, are activated esters, such as esters with vinyl-like alcohols (i.e. enols), such as vinyl-like lower alkenols, or aryl esters such as 4-nitrophenyl- or 2,4-dinitrophenyl ester, heteroaromatic esters such as benzotriazole ester, for example 1-benzotriazole ester, or diacyliminoesters such as succinylimino or phthalylimino ester.

The acylation with an acid derivative, such as an anhydride, especially with an acid halide, can be carried out in the presence of an acid-binding agent, for example an organic base, such as an organic amine, for example a tertiary amine, such as tri-lower alkylamine, for example trimethylamine, triethylamine or ethyldiisopropylamine, or N,N-di-lower alkylaniline, for example N,N-dimethylaniline, or a cyclic tertiary amine, such as an N-lower alkylated morpholine, such as N-methylmorpholine, or a base of the pyridine type, for example pyridine, an inorganic base, for example an alkali metal- or alkaline earth metal hydroxide, -carbonate or bicarbonate, for example sodium, potassium or calcium hydroxide, -carbonate or -bicarbonate, or an oxirane, for example a lower 1,2-alkylene oxide such as ethylene oxide or propylene oxide.

The above acylations may be carried out in an inert, preferably anhydrous solvent or solvent mixture, for example in a carboxylic acid amide, such as formamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at reduced or elevated temperature, for example at —40° to approximately 100°, preferably at —10° to +40°, and/or an inert gas atmosphere, for example a nitrogen atmosphere.

In an acylating acid of the formula III, V or VII or in an acid derivative thereof, a protected amino group may be present in ionic form, that is the starting material of the formula III, V or VII may be used in the form of an acid addition salt, preferably with a strong inorganic acid such as a hydrohalic acid, for example hydrochloric acid or sulphuric acid.

Also, an acid derivative can, if desired, be formed in situ. Thus, for example, a mixed anhydride is obtained by treating an acid of the formula III, or an acid of the formula V in which X—W represents a —CO— group, with correspondingly protected functional groups, or a suitable salt thereof, such as an ammonium salt, for example with an organic amine, such as 4-methylmorpholine, or by treating a metal salt, for example an alkali metal salt, with a suitable acid derivative such as a corresponding acid halide of an optionally substituted lower alkanecarboxylic acid, for example trichloroacetyl chloride, or with a semi-ester of a carbonic acid semi-halide, for example chloroformic acid ethyl ester or isobutyl ester, and the mixed anhydride obtainable in this manner is used without isolation.

An acid chloride of an acid of the formula V in which X—W represents a —O—CO—, —S—CO— or —N-H—CO— grouping and in which the aminocarboxylic acid grouping HOOC—$CH(NH_2)$— is present in protected form, may be formed, for example, in situ, by reacting an aminocarboxylic acid of the formula VI in which X represents oxygen, sulphur or an —NH— group and the HOOC—$CH(NH_2)$— grouping is present in protected form, with phosgene in the presence of a hydrochloric acid acceptor in an inert organic solvent or solvent mixture. The hydrochloric acid acceptors, solvents, and reaction conditions are the same as those mentioned for the acylation of compounds of the formula II or IV; for example the reaction can be carried out in the presence of pyridine in methylene chloride and toluene at approximately 0° to approximately +10°.

In the same manner it is possible, for example in situ, to produce an acid chloride of an acid of the formula VII in which W represents a —CO— group, and in which the 4-carboxyl group and further functional groups optionally present in the —A—C(Y)(Z)— groups and $R_1$ are protected, from a correspondingly protected compound of the formula IV by treating with chlorosulphonyl isocyanate.

In a resulting intermediate of the formula I in which at least one of the functional groups is present in protected form, it is possible in the usual manner, known per se, for still unprotected functional groups to be protected or for protective groups present to be exchanged for other protective groups, for example by splitting off the protective group present and introducing the other desired protective group.

In a resulting intermediate of the formula I in which at least one of the functional groups is present in protected form, an $R_2$ group present in the radical $R_1$ can be exchanged for a different $R_2$ group, as explained for this reaction in the case of the end products of the formula I.

In a resulting intermediate of the formula I in which $R_3$ is hydrogen and all the functional groups are present in protected form, the 7α-methoxy group $R_3$ can be introduced in a manner known per se, for example by treating the said intermediate in succession with an anion-forming agent, an N-halogenating agent and methanol.

A suitable anion-forming agent is especially an organometallic base, especially an organo alkali metallic base, particularly an organolithium base. Compounds of this type are in particular corresponding alcoholates, such as suitable lithium-lower alkanolates, especially lithium methylate, or corresponding metal hydrocarbon bases, such as lithium-lower alkanes and phenyl lithium. The reaction with the anion-forming organometallic base is usually carried out while cooling, for example at approximately 0° C. to approximately −80° C., in the presence of a suitable solvent or diluent, for example an ether such as tetrahydrofuran, when using lithium methylate, also in the presence of methanol and, if desired, in a closed vessel and/or in an inert gas atmosphere, for example a nitrogen atmosphere.

The N-halogenating agent used is usually a sterically hindered organic hypohalite, especially hypochlorite, and in particular a corresponding aliphatic hypohalite, for example hypochlorite, such as a tert.-lower alkyl hypohalite, for example hypochlorite. In particular the tert.-butyl hypochlorite that is reacted with the non-isolated product of the anionisation reaction is used.

The N-halogenated intermediate is converted in the presence of an excess of the anion-forming base, especially lithium methylate, under the reaction conditions and without being isolated, into a 7-acyliminocephem compound and this is converted by the addition of methanol into a 7α-methoxycephem compound. If necessary the elements of the hydrohalic acid, especially hydrochloric acid, must be split off from the N-halogenated intermediate; this is effected by the addition of a base that splits off hydrogen halide, such as a suitable alkali metal lower alkanolate, for example lithium tert.-butylate, this reaction usually occurring under the conditions of the anion- and N-halogen compound-forming reaction and it being possible to carry it out in the presence of methanol to obtain the 7α-methoxycephem compound directly instead of the acylimino compound. The starting material is usually a compound of the formula I in which functional groups are present in protected form: this is reacted with an excess of the anion-forming agent, for example lithium methylate or phenyl lithium, in the presence of methanol, the mixture is then treated with the N-halogenating agent, for example tert.-butyl hypochlorite, and the desired compound of the formula I in which functional groups are protected is thus obtained directly. It is also possible to add the methanol subsequently, it being possible for the dehydrohalogenation and the addition of methanol to be carried out at somewhat higher temperatures than the anion- and N-halogen compound-forming reactions, for example at approximately 0° C. to approximately −20° C., if necessary in a closed vessel and/or in an inert gas atmosphere, for example a nitrogen atmosphere.

In the above reactions that are carried out under basic conditions 3-cephem compounds can optionally partially be isomerised to form 2-cephem compounds. A 2-cephem compound obtained or a mixture of a 2- and a 3-cephem compound can be isomerised in a manner known per se to form the desired 3-cephem compound.

This isomerisation can be carried out, for example, by oxidising the 2-cephem compound or the mixture of 2- and 3-cephem compounds obtained in the 1-position and reducing the so-obtained 1-oxides of the corresponding 3-cephem compounds.

Suitable oxidising agents for the oxidation in the 1-position of cephem compounds are, for example, inorganic per acids that have a reduction potential of at least +1.5 volts and consist of non-metallic elements, organic per acids or mixtures of hydrogen peroxide and acids, especially organic carboxylic acids, with a dissociation constant of at least $10^{-5}$. Suitable inorganic per acids are periodic and persulphuric acid. Organic per acids are corresponding percarboxylic and persulphonic acids, which are added as such or can be formed in situ by using at least one equivalent of hydrogen peroxide and a carboxylic acid. It is advantageous in this case to use a large excess of the carboxylic acid if, for example, acetic acid is used as solvent. Suitable per acids are, for example, performic acid, peracetic acid, pertrifluoroacetic acid, permaleic acid, perbenzoic acid, 3-chloroperbenzoic acid, monoperphthalic acid or p-toluenepersulphonic acid.

The oxidation can likewise be carried out using hydrogen peroxide with catalytic amounts of an acid having a dissociation constant of at least $10^{-5}$, it being possible to use low concentrations, for example 1-2% and lower, but also larger amounts of the acid. The activity of the mixture here depends in particular on the strength of the acid. Suitable mixtures are, for example, those of hydrogen peroxide with acetic acid, perchloric acid or trifluoroacetic acid.

The above oxidation can be carried out in the presence of suitable catalysts. For example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually at least equimolar amounts of the oxidising agent, but preferably a small excess of approximately 10% to approximately 20%, are used. The oxidation is carried out under mild conditions, for example at temperatures of approximately −50° C. to approximately +100° C., preferably from approximately −10° C. to approximately +40° C.

The oxidation of 2-cephem compounds to form the 1-oxides of the corresponding 3-cephem compounds can also be carried out by treating them with ozone; or with organic hypohalite compounds, such as lower alkyl hypochlorites, for example tert.-butyl hypochlorite, which are used in the presence of inert solvents, such as optionally halogenated hydrocarbons, for example methylene chloride, and at temperatures of approximately −10° C. to approximately +30° C.; with periodate compounds such as alkali metal periodates, for example potassium periodate, which are preferably used in an aqueous medium at a pH of approximately 6 and at temperatures of approximately −10° C. to approximately +30° C.; with iodobenzene dichloride, which is used in an aqueous medium, preferably in the presence of an organic base, for example pyridine, and while cooling, for example at temperatures of approximately −20° C. to approximately 0°; or with any other oxidising agent that is suitable for converting a thio- to a sulphoxide grouping.

The reduction of the 1-oxides of 3-cephem compounds can be carried out in a manner known per se by treating with a reducing agent, if necessary in the presence of an activating agent. The reducing agents that come into consideration are, for example, as follows: catalytically activated hydrogen, wherein noble metal catalysts are used that contain palladium, platinum or rhodium, and that are optionally used together with a suitable carrier material such as carbon or barium sulphate; reducing tin, iron, copper or manganese cations, which are used in the form of corresponding compounds or complexes of an inorganic or organic nature, for example in the form of tin(II) chloride, fluoride, acetate or formate, iron(II) chloride, sulphate, oxalate or succinate, copper(I) chloride, benzoate or oxide, or manganese(II) chloride, sulphate, acetate or oxide, or in the form of complexes, for example with ethylenediaminetetraacetic acid or nitrolotriacetic acid; reducing dithionite, iodo or iron(II) cyanide anions, which are used in the form of corresponding inorganic or organic salts, such as alkali metal dithionite, for example, sodium or potassium dithionite, sodium or potassium iodide or sodium or potassium iron(II) cyanide, or in the form of the corresponding acids, such as hydroiodic acid; reducing trivalent inorganic or organic phosphorus compounds, such as phosphines, also esters, amides and halides of phosphinous, phosphonous or phosphorous acid, as well as phosphorus-sulphur compounds which correspond to these phosphorus-oxygen compounds, in which organic radicals are especially aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide, etc.; reducing halosilane compounds that have at least one hydrogen atom bonded to the silicon atom, and that part from halogen, such as chlorine, bromine or iodine, may also contain organic radicals, such as aliphatic or aromatic groups, for example optionally substituted lower alkyl or phenyl groups, such as chlorosilane, bromosilane, di- or trichlorosilane, di- or tri-bromosilane, diphenylchlorosilane, dimethylchlorosilane etc.; reducing quaternary chloromethylene iminium salts, especially chlorides or bromides, wherein the iminium group is substituted by a divalent or two monovalent organic radicals, such as optionally substituted lower alkylene or lower alkyl groups, such as N-chloromethylene-N,N-diethyliminium chloride or N-chloromethylenepyrrolidinium chloride; and complex metal hydrides, such as sodium borohydride, in the presence of suitable activating agents, such as cobalt(II) chloride, and borane dichloride.

Activating agents that are used together with those of the above mentioned reducing agents that do not themselves have Lewis acid properties, that is especially those used together with the dithionite, iodo or iron(II) cyanide and the non-halogen-containing trivalent phosphorus reducing agents, or in the catalytic reduction, are in particular organic carboxylic and sulphonic acid halides, also sulphur, phosphorus or silicon halides with the same or higher second order hydrolysis constants than benzoyl chloride, for example phosgene, oxalyl chloride, acetic acid chloride or bromide, chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane, also suitable acid anhydrides, such as trifluoroacetic anhydride, or cyclic sultones, such as ethane sultone, propane-1,3-sultone, butane-1,4-sultone or hexane-1,3-sultone.

The reduction is preferably carried out in the presence of solvents or mixtures thereof, the selection of which is determined chiefly by the solubility of the starting materials and the choice of reducing agent, thus, for example, lower alkanecarboxylic acids or esters thereof, such as acetic acid and ethyl acetate, for the catalytic reduction, and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofuran or dioxan, ketones, for example acetone, or sulphones, especially aliphatic sulphones, for example dimethylsulphone or tetramethylsulphone, etc., together with the chemical reducing agents, wherein these solvents preferably contain no water. The temperatures used are normally from approximately −20° C. to approximately 100° C., and when using very reactive activating agents the reaction can be carried out at lower temperatures.

Starting materials of the formula II and corresponding compounds with protected functional groups are known or can be produced in a manner known per se.

This invention relates also to compounds of the formula III, in which the aminocarboxylic acid grouping HOOC—CH(NH$_2$)— and further functional groups optionally present in the grouping —A—C(Y)(Z)— are present in protected form, which are new.

Such compounds of the formula III, with correspondingly protected functional groups, are produced, for example, by acylating a compound of the formula

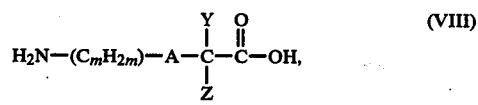

in which the amino group may optionally be substituted by a group allowing acylation, and functional groups optionally present in the grouping —A—C(Y)(Z)— are protected with the intermediate protection of the carboxyl group, with a reactive functional derivative of an acid of the formula V, in which the aminocarboxylic acid grouping HOOC—CH(NH$_2$)— is present in protected form, or, when X—W together represent a —CO— group, also with a corresponding free acid or with a salt thereof, and, if desired, converting a compound obtained into a different compound of the formula III with correspondingly protected functional groups.

The groups allowing acylation, as well as the protective groups of the aminocarboxylic acid grouping HOOC—CH(NH$_2$)— and the grouping —A—C(Y)(Z)—, are the same as those mentioned under the compounds of the formula II or IV as well as I. The carboxyl protective groups already mentioned may likewise be used per se for the intermediate protection of the carboxyl group in the compound of the formula VIII, but the carboxyl protective groups used for the intermediate protection in the acylation under discussion here must differ from the remaining protective groups that are necessarily to remain in the compounds of the formula III in the manner in which they are split off, so that after the acylation reaction they can be selectively split off. If, for example, a protective group that can be split off under conditions of hydrogenolysis, such as one of the optionally substituted benzyl groups mentioned, for example the benzyl- or p-nitrobenzyl group, is used for the intermediate protection of the carboxyl group, then it must not be possible to split off the other protective groups by hydrogenolysis; they can be, for example, the mentioned tert.-lower alkyl groups, such as tert.-butyl or tert.-lower alkoxycarbonyl groups such as tert.-butoxycarbonyl, which can be split off only by acidolysis.

The acylation can otherwise be carried out analogously to the acylation of compounds of the formula IV with an acid of the formula V, or a correspondingly protected and reactive functional derivative thereof.

In a resulting compound of the formula III with correspondingly protected functional groups, a protective group can be split off optionally selectively, or a functional group that has optionally become freed during the acylation reaction can be protected. In a resulting compound of the formula III in which Z represents hydrogen and Y represents hydroxy, the α-hydroxy group can be converted into an α-oxo group by oxidation in the manner described for the oxidation of compounds XI to α-keto acids IX, for example, with temporary protection of the carboxyl group as ester, by treating with manganese dioxide, and in a resulting compound of the formula III in which Z and Y together represent the oxo group, this can be converted into the corresponding oximino group by treating with a hydroxylamine of the formula $H_2N-O-R°$, which reaction can be carried out analogously to the conversion of α-keto acids of the formula IX into oximino compounds of the formula VIIIa.

Compounds of the formula IV, in which the amino group may optionally be substituted by a group allowing acylation and in which the 4-carboxyl group and the other functional groups optionally present in the radical $R_1$ and in the grouping $-A-C(Y)(Z)-$ may be present in protected form, are either known or new. They can be produced according to processes known per se.

In the new compounds of the formula IV the index m, A, $R_1$ and $R_3$ have the meanings given under formula I and X and Z together represent an $=N-O-R°$ group in which R° is hydrogen or optionally substituted lower alkyl. These new compounds in which the carboxyl group is optionally esterified in a form that can be split physiologically, as well as the pharmaceutically acceptable salts thereof, also have an antibiotic activity. Together with the process for their manufacture, they are likewise included in the present invention.

The specified new, antibiotically active compounds of the formula IV may be used as antibacterial antibiotics. For example, they are effective in vitro against enterobacteria, for example *Escherichia coli*, in minimum concentrations of 0.8 mcg/ml and against cocci in minimum concentrations of 0.1 mcg/ml. In vivo, in the case of subcutaneous application to a mouse, they are effective, for example, against enterobacteria such as *Escherichia coli*, in minimum doses of 6 mg/kg and against cocci in minimum doses of 15 mg/kg. The new compounds can therefore be used correspondingly, for example in the form of antibiotically active preparations, for the treatment of infections caused by enterobacteria such as *Escherichia coli*, and by cocci.

Preferred are those compounds of the formula IV in which the index m is 1, A represents thienylene, especially 2,5-thienylene, or furylene, especially 2,5-furylene, Y and Z together represent an $=N-O-R°$ group, especially in the syn-configuration, in which R° represents hydrogen, lower alkyl, especially methyl, or substituted lower alkyl, especially carboxy-lower alkyl, such as 2-carboxyethyl or 3-carboxypropyl, $R_1$ represents a $-CH_2R_2$ group in which $R_2$ is acetoxy, carbamoyloxy or heterocyclylthio, especially substituted tetrazolylthio, such as 1-methyltetrazol-5-ylthio, and $R_3$ represents hydrogen, as well as salts thereof.

Compounds of the formula IV in which optionally the amino group and the other functional groups may be protected or substituted as described, and the salts thereof, can be produced by acylating a compound of the formula II, in which the amino group is optionally substituted by a group allowing acylation and in which the 4-carboxyl group and further functional groups optionally present in the radical $R_1$ may be present in protected form, with an acid of the formula VIII, in which the amino group may optionally be protected, and functional groups optionally present in the $-A-C(Y)(Z)-$ grouping are protected, or with a reactive functional derivative of such an acid or a salt thereof, if desired splitting off the protective groups in a compound obtained and/or, if desired, converting a group $R_1$ in a compound obtained into a different group $R_1$, and/or, if desired, converting a compound obtained in which $R_3$ is hydrogen into a compound in which $R_3$ is methoxy, and/or, if necessary, isomerising a resulting 2-cephem compound or a resulting mixture of a 2-cephem- and 3-cephem compound into the 3-cephem compound, and/or, if desired, separating a resulting isomeric mixture into the isomers, and/or, if desired, converting a resulting compound with a salt-forming group into a salt or a resulting salt into the free compound.

The groups allowing acylation in the compounds of the formula II and VIII and the protective groups are the same as those already mentioned above.

The acylation of corresponding protected compounds of the formula II with an acid of the formula VIII, or with a reactive functional derivative thereof, the splitting off of the protective groups, the conversion of a group $R_1$ into a different group $R_1$, and the introduction of the methoxy group $R_3$ as well as the salt formation can be carried out in an analogous manner to that in the acylation of correspondingly protected compounds of the formula II or IV with an acid of the formula III or V and the corresponding subsequent operations.

Acids of the formula V, reactive functional derivatives thereof, the starting materials for the compounds of the formula $HOOC-CH(NH_2)-(C_nH_{2n})-X-H$ (VI) and correspondingly protected derivatives are known or can be produced according to methods known per se, for example in situ.

Reactive functional derivatives of acids of the formula VII in which the 4-carboxyl group and functional groups optionally present in the radical $R_1$ and in the $-A-C(Y)(Z)-$ grouping may be present in the protected form, are produced in a manner known per se from correspondingly protected compounds of the formula IV.

Acids of the formula VIII and corresponding reactive functional and protected derivatives thereof are either known or can be produced according to methods known per se.

The acids falling under the formula VIII of the formula

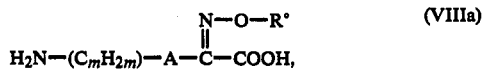

$$H_2N-(C_mH_{2m})-A-\overset{\overset{N-O-R^\circ}{\|}}{C}-COOH, \quad \text{(VIIIa)}$$

in which the index m is 1, and A and R° have the meanings given under formula I, as well as corresponding functional derivatives thereof protected at the amino group and reactive with respect to the carboxyl group, are new and can be produced in a manner known per se by treating an α-keto acid of the formula $H_2N-(C_mH_{2m})-A-C(=O)-COOH$ (IX), in which m and A have the meanings given under formula VIIIa and in which the amino group is present in the protected form, with a hydroxylamino compound of the formula $H_2N-O-R^\circ$ in which R° has the meaning given under formula VIIIa, and, if desired, in a resulting compound of the formula VIIIa having a protected amino group, converting this into the free amino group and/or, if desired, converting the resulting free amino group into a differently protected amino group, and/or, if desired, separating a resulting isomeric mixture into the isomers, and/or, if desired, in a resulting compound of the formula VIIIa in which the amino group is protected, converting the carboxyl group into a reactive functional derivative thereof.

In an α-keto acid of the formula IX A is especially one of the preferred groups mentioned under formula I, especially 2,5-furylene, 2,5-thienylene or 1,4-phenylene. The amino protective group in a compound of the formula IX is one of those mentioned above, for example one of the acyl groups mentioned under formula I that is stable during the reaction and then can readily be split off, especially the trifluoroacetyl group.

The reaction of the α-keto acid with the hydroxylamine compound $H_2N-O-R^\circ$ is carried out in the usual manner, for example, by allowing the two reactants to react in a solvent, such as water or an organic solvent, such as an alcohol, for example methanol, at slightly elevated or reduced temperature, optionally in an inert gas atmosphere, such as a nitrogen atmosphere. The hydroxylamine compound can, also in situ, be liberated from one of its salts, for example a hydrohalide such as hydrochloride, by treating with an inorganic base, such as an alkali metal hydroxide, for example sodium hydroxide, or an organic base, such as a tertiary amine, for example a tri-lower alkylamine such as triethylamine or ethyldiisopropylamine, or a heterocyclic tertiary base such as pyridine.

In a resulting compound of the formula VIIIa the protective group can be split off according to customary methods that have already been mentioned hereinbefore, for example a trifluoroacetyl group can be split off by alkaline hydrolysis.

In a resulting compound of the formula VIIIa the free amino group can be converted into one of the specified protected amino groups according to customary methods mentioned hereinbefore, for example by treating with an acid anhydride, such as the anhydride of carbonic acid mono tert.-butyl ester in the presence of a base, into the corresponding N-acyl-, for example N-tert.-butoxycarbonyl compound.

Compounds of the formula VIIIa and the protected derivatives thereof, when formed from the α-keto acid IX and the hydroxylamine compound $H_2N-O-R^\circ$ usually result in the form of a mixture of syn- and anti-isomers, the syn-isomers usually being formed in a larger quantity. The two isomers may be separated into the syn- and anti-isomers, for example by crystallisation, chromatography, distillation and the like.

The functional derivatives reactive with respect to the carboxyl group, of compounds of the formula VIIIa in which the amino group is protected, are the same as those mentioned under the acids of the formula III and are especially anhydrides, such as mixed anhydrides with the specified inorganic or organic acids, or activated esters, such as those with the specified alcohols.

The conversion of an obtained compound of the formula VIIIa in which the amino group is protected into a corresponding reactive functional derivative with respect to the carboxyl group is effected in a manner known per se, optionally in situ, for example as described for the production of reactive functional derivatives of acids of the formula III or according to the known manufacturing methods for the reactive functional derivatives of the formula III.

Acid halides are produced, for example, by reacting a compound of the formula VIIIa, with a protected amino group, or a salt thereof, with a halogenating agent, for example, phosphorus pentachloride, thionyl chloride or oxalyl chloride. The reaction is preferably carried out in a non-aqueous solvent or solvent mixture, such as a carboxylic acid amide, for example dimethylformamide, and/or in the presence of a base, such as a tertiary amine, such as tri-lower alkylamine, for example triethylamine, or a tertiary cyclic amine, such as N-methylmorpholine.

Symmetrical anhydrides or mixed anhydrides different from halides of compounds of the formula VIIIa having a protected amino group may be produced, for example, by reacting a corresponding compound having a free carboxyl group, preferably a salt, especially an alkali metal salt, for example a sodium, or ammonium, for example a triethylammonium, salt thereof, with a reactive derivative, such as a halide, for example the chloride, of one of the specified acids, for example a lower alkyl haloformate, such as isobutyl chloroformate, or an optionally halogenated lower alkanecarboxylic acid chloride, for example trichloroacetyl chloride.

Activated esters of compounds of the formula VIIIa having a protected amino group can be produced, for example, by reacting a corresponding compound having a free carboxyl group in the presence of a carbodiimide, for example one of the above-mentioned carbodiimides such as N,N'-dicyclohexyl carbodiimide, with a phenol, optionally substituted, for example, by nitro or halogen, such as chlorine, such as, inter alia, nitrophenol, for example 4-nitrophenol or 2,4-dinitrophenol, or a polyhalophenol, for example 2,3,4,5,6-pentachlorophenol, or with 1-hydroxybenzotriazole.

The present invention also relates to α-keto acids of the formula IX which are new. They can be produced in a manner known per se by oxidising the methyl group, in a compound of the formula $H_2N-(C_mH_{2m})-A-C(=O)-CH_3$ (X) in which m and A have the meanings given under formula VIIIa and in which the amino group is present in protected form, to form a carboxyl group, or oxidizing the α-hydroxy group, in an α-hydroxy acid of the formula $H_2N-(C_mH_{2m})-A-CH(OH)-COOH$ (XI) in which m and A have the meanings given under formula VIIIa and in which the amino group is present in protected form, into an α-oxo group.

In a starting material of the formula X or XI, the amino group is protected, for example, by one of the specified acyl protective groups, especially by the trifluoroacetyl group. The oxidation of a compound X is carried out in the usual manner with one of the oxidising agents suitable for the conversion of aromatic acetyl compounds, that is aryl methyl ketones, into corresponding α-keto acids, that is arylglyoxylic acids. Suitable oxidising agents are, for example, oxidising oxides or oxygen-containing acids, such as those of selenium, sulphur, manganese, chromium or nitrogen, or salts of corresponding acids, especially alkali metal salts, such as potassium salts, thereof, wherein the salts are optionally used in the presence of mineral acids such as hydrochloric acid or sulphuric acid, hydrogen peroxide or alternatively oxygen in the presence of a catalyst, such as platinum on carbon. Oxidising agents to be highlighted are selenium dioxide or selenious acid, salts of permanganic acid, such as potassium permanganate, salts of dichromic acid, such as potassium dichromate, and nitrous acid, which is formed in situ from an inorganic nitrite salt, such as a corresponding alkali metal salt or alkaline earth metal salt, for example sodium salt, and an acid, such as hydrochloric or sulphuric acid.

The oxidation is carried out in water or an optionally water-miscible, optionally water-containing organic solvent, such as pyridine, acetic acid, an ether such as tetrahydrofuran or dioxan, or alternatively an alcohol such as a lower alkanol, for example methanol or ethanol, at temperatures of approximately 0° to approximately 100°, the process usually being carried out at elevated temperatures, that is at approximately 60°–90°.

Preferably a compound of the formula X is oxidised with selenium dioxide in a solvent such as pyridine at approximately 80°–90°, or alternatively, according to German Offenlegungsschrift No. 2 528 786, with sodium or potassium nitrite in aqueous hydrochloric, sulphuric or phosphoric acid.

The oxidation of α-hydroxy acids of the formula XI, in which the amino group is present in protected form, to form the corresponding α-keto acids of the formula IX can likewise be carried out in a manner known per se, that is such as the manner known for the oxidation of hydroxy groups to oxo groups. The oxidising agents that come into consideration are again oxidising oxides, such as those of manganese, chromium, nitrogen or sulphur, such as manganese dioxide, chromium trioxide, for example Jones reagent or chromium trioxide in the presence of acetic acid, sulphuric acid or pyridine, dinitrogen tetroxide, dimethyl sulphoxide optionally in the presence of dicyclohexyl carbodiimide or oxygen, and peroxides, such as hydrogen peroxide, oxygen-containing acids such as permanganic acid, chromic acid or hypochlorous acid or salts thereof, such as potassium permanganate, sodium or potassium dichromate or potassium hypochlorite. The α-hydroxy group can also be converted into the α-oxo group by Oppenauer oxidation, that is by treating with the salt of a sterically hindered alcohol, such as aluminium or potassium tert.-butoxide, isopropoxide or phenoxide in the presence of a ketone, such as acetone, cyclohexanone or fluorenone. A further possibility of converting the α-hydroxy group into the α-oxo group consists in dehydrogenation, for example with Raney nickel.

The oxidation is, depending on the oxidising agent, carried out in water or an optionally water-miscible, optionally water-containing solvent, at temperatures of approximately 0° to approximately 100°.

Compounds of the formula XI are known or can be produced in a manner known per se.

The pharmacologically acceptable compounds of the present invention can be used, for example, for the production of pharmaceutical preparations which contain an effective amount of the active substance together or in admixture with inorganic or organic, solid or liquid, pharmaceutically acceptable carriers which are preferably suitable for parenteral administration.

The pharmacologically active compounds of the present invention are preferably used in the form of injectable, for example intravenously administrable, preparations or of infusion solutions. Such solutions are preferably isotonic aqueous solutions or suspensions, wherein these can be produced before use, for example from lyophilised preparations that contain the active substance alone or together with a carrier, for example mannitol. The pharmaceutical preparations may be sterilised and/or may contain adjuvants, for example preservatives, stabilisers, wetting agents and/or emulsifiers, solubilisers, salts for regulating the osmotic pressure and/or buffers. The pharmaceutical preparations in question which, if desired, may contain other pharmacologically valuable substances, are produced in a manner known per se, for example by means of conventional dissolving and lyophilising processes, and contain from approximately 0.1% to 100%, especially from approximately 1% to approximately 50%, in the case of lyophilisates up to 100%, of the active substance. Depending on the nature of the infection and the state of the infected organism, daily dosages of approximately 0.5 g to approximately 5 g s.c. are used to treat warm-blooded animals of approximately 70 kg weight.

The following Examples serve to illustrate the invention: temperatures are given in degrees Celsius.

The following systems are used in the thin layer chromatography:

System 52A: n-butanol/glacial acetic acid/water (67:10:23)

System 96: sec.-butanol/glacial acetic acid/water (67:10:23)

System 101: n-butanol/pyridine/glacial acetic acid/water (38:24:8:30)

System 101A: n-butanol/pyridine/glacial acetic acid/water (42:24:4:30).

$R_f$ details for thin layer chromatography:

CS: chromatography on silica gel ready-made plates SL 254 produced by Messrs. Antec, Birsfelden.

CC: chromatography on cellulose ready-made plates produced by Messrs. Merck, Darmstadt.

The following abbreviations are used in the Examples:

BOC=tert.-butoxycarbonyl
Z=benzoxycarbonyl.

EXAMPLE 1

(a) A mixture of 1.60 g of 7β-{2-[4-((2R)-2-BOC-amino-2-tert.-butoxycarbonylethoxycarbonylamino)-phenyl]acetylamino}-3-[(1-methyl-1H-tetrazol-5-yl)thiomethyl]-3-cephem-4-carboxylic acid diphenylmethyl ester, 1.0 g of anisole, 2.50 ml of methylene chloride and 25 ml of trifluoroacetic acid is stirred for one hour at room temperature with the exclusion of atmospheric moisture. From the solution, which is initially clear, a voluminous precipitate is precipitated. At the end of the reaction time the suspension is poured onto an ice-cold mixture of petroleum ether (300 ml) and diethyl ether (150 ml), the resulting trifluoroacetate is suction-filtered off, washed with diethyl ether and dried at room temperature under high vacuum.

The crude 7β-{2-[4-((2R)-2-amino-2-carboxyethoxycarbonylamino)phenyl]acetylamino}-3-[(1-methyl-1H-tetrazol-5-yl)-thiomethyl]-3-cephem-4-carboxylic acid trifluoroacetate is made into a paste with 25 ml of water, the pH is adjusted to 6.0 by the addition of 1N sodium bicarbonate solution, the suspension is stirred for 15 minutes at room temperature, then the small amount of undissolved product is separated off by treating with activated carbon and filtering through Celite. A large amount of ethanol is added to the clear filtrate, the pH is corrected to 5.5 and the solution is concentrated in a rotary evaporator (high vacuum) at 45°. The aqueous solution is concentrated by evaporation a further two times with ethanol, then the 7β-{2-[4-((2R)-2-amino-2-carboxyethoxycarbonylamino)phenyl]acetylamino}-3-[(1-methyl-1H-tetrazol-5-yl)thiomethyl]-3-cephem-4-carboxylic acid sodium salt is precipitated by adding ethanol, suction-filtered off and washed in succession with ethanol, ethanol/diethyl ether (1:1) and diethyl ether. The product can be further purified by dissolving in water and concentrating by evaporation or precipitating with ethanol. Mp. 185°–190° (with decomposition); $[\alpha]_D = +26 \pm 1°$ (c=3.409; in water); CS: $R_{f524}=0.05$; $R_{f101}=0.32$; $R_{f101A}=0.45$.

The starting material can be obtained as follows:

(b) (2R)-N-BOC-serine tert.-butyl ester is obtained from (2R)-N-BOC-serine (Mp. 89°–90°, $[\alpha]_D = -2 \pm 1°$ (c=3; in methanol)) by reacting with O-tert.-butylisourea in methylene chloride [(E. Vowinkel, Chem. Ber. 100, 16 (1967)]. Mp. 75°–76°, $[\alpha]_D = -8 \pm 1°$ (c=5.2 in chloroform).

(c) A solution of 13.0 g (2R)-N-BOC-serine tert.-butyl ester in 125 ml of methylene chloride is cooled to 0°, 28 ml of phosgene solution (20% in toluene) are added and subsequently a mixture of 6 ml of pyridine and 45 ml of methylene chloride are added dropwise over a period of 30 minutes whilst stirring and cooling at +5° to +10°. The suspension is stirred for 90 minutes in an ice bath, and then a solution of 12.0 g of 4-aminophenylacetic acid benzyl ester in 65 ml of methylene chloride and 6 ml of pyridine is added dropwise over a period of 20 minutes at 0° to +5°, and the reaction mixture is stirred for 3 hours at room temperature. The suspension is diluted with methylene chloride and washed in succession with water, 10% citric acid, water, 1N sodium bicarbonate solution and water. The organic phase is dried over sodium sulphate and the methylene chloride is evaporated off in a rotary evaporator at 50°. The 4-((2R)-BOC-amino-2-tert.-butoxycarbonylethoxycarbonylamino)phenylacetic acid benzyl ester obtained is purified over silica gel and recrystallised from petroleum ether/ethyl acetate (20:1). Mp. 74°–76°; $[\alpha]_D = -22 \pm 1°$ (c=2.85, in chloroform).

(d) A solution of 25.0 g of 4-((2R)-2-BOC-amino-2-tert.-butoxycarbonylethoxycarbonylamino)phenylacetic acid benzyl ester in 300 ml of ethyl acetate is hydrogenated in the presence of 3.0 g of palladium on activated carbon (10%). The catalyst is filtered off, washed with ethyl acetate, the filtrate is concentrated in a rotary evaporator at 50° and the 4-((2R)-2-BOC-amino-2-tert.-butoxycarbonylethoxycarbonylamino)phenylacetic acid is crystallised by the addition of petroleum ether. Mp. 133°–137°; $[\alpha]_D = -36 \pm 1°$ (c=1.06, in chloroform).

(e) A solution of 5.0 g of 7β-amino-3-[(1-methyl-1H-tetrazol-5-yl)thiomethyl]-3-cephem-4-carboxylic acid diphenylmethyl ester and 4.50 g of 4-((2R)-2-BOC-amino-2-tert.-butoxycarbonylethoxycarbonylamino)-phenylacetic acid in a mixture of 30 ml of tetrahydrofuran and 15 ml of N,N-dimethylformamide is cooled with an ice bath to +5°, a solution of 2.0 g of N,N'-dicyclohexyl carbodiimide in 10 ml of tetrahydrofuran is added dropwise over a period of 20 minutes while stirring and cooling, then the ice bath is removed and the reaction mixture is stirred at room temperature. After a reaction time of 3 hours a further 2.0 g of solid N,N'-dicyclohexyl carbodiimide is added to the suspension. After stirring for a total of 6.5 hours, the suspension is suction-filtered off, the filtered material is washed with tetrahydrofuran, a large amount of ethyl acetate is added to the filtrate and the tetrahydrofuran is removed by concentrating in a rotary evaporator at 45°. The resulting solution is diluted with ethyl acetate, washed in succession with water, 1N sodium bicarbonate solution and water, the organic phase is separated off, dried over sodium sulphate and concentrated by evaporation in a rotary evaporator at 45°. The remaining foam is purified by chromatography over 20 times the amount of silica gel. The fractions with methylene chloride/methyl acetate (7:1) and (5:1) as eluant are combined and the 7β-{2-[4-((2R)-2-BOC-amino-2-tert.-butoxycarbonylethoxycarbonylamino)phenyl]acetylamino}-3-[(1-methyl-1H-tetrazol-5-yl)thiomethyl]-3-cephem-4-carboxylic acid diphenylmethyl ester is crystallised from a little ethyl acetate. Mp. 155°–160° CS;(eluant: toluene/chloroform/ethyl acetate/ethanol(16:16:16:1): $R_f=0.51$.

EXAMPLE 2

(a) A mixture of 7.20 g of 7β{2-[4-((2S)-2-BOC-amino-2 tert.-butoxycarbonylethoxycarbonylamino)-phenyl]acetylamino}-3-[(1-methyl-1H-tetrazol-5-yl)thiomethyl]-3-cephem-4-carboxylic acid diphenylmethyl ester, 3.0 ml of anisole, 7.0 ml of methylene chloride and 70 ml of trifluoroacetic acid is stirred for 45 minutes at room temperature with the exclusion of atmospheric moisture. A voluminous precipitate is precipitated from the initially clear solution. At the end of the reaction time the suspension is poured onto an ice-cold mixture of petroleum ether (1000 ml) and diethyl ether (500 ml), the resulting trifluoroacetate is suction-filtered off, washed with diethyl ether and dried at room temperature under high vacuum.

The crude 7β-{2-[4-((2S)-2-amino-2-carboxyethoxycarbonylamino)phenyl]acetylamino}-3-[(1-methyl-1H-tetrazol-5-yl)thiomethyl]-3-cephem-4-carboxylic acid trifluoroacetate is made into a paste with 40 ml of water, the pH is adjusted to 6.0 by the addition of 1N sodium bicarbonate solution, the suspension is stirred for 15 minutes at room temperature, then the small quantity of undissolved product is separated off by treating with activated carbon and filtering through Celite. A large amount of ethanol is added to the clear filtrate, the pH is corrected to 5.5 and the solution is concentrated in a rotary evaporator (high vacuum) at 45°. The aqueous solution is concentrated by evaporation a further two times with ethanol, then the 7β-{2-[4-((2S)-2-amino-2-carboxyethoxycarbonylamino)phenyl]acetylamino}-3-[(1-methyl-1H-tetrazol-5-yl)thiomethyl]-3-cephem-4-carboxylic acid sodium salt is precipitated by adding ethanol, suction-filtered off, and washed in succession with ethanol, ethanol/diethyl ether (1:1) and diethyl ether. The product can be further purified by dissolving in water and concentrating by evaporation or precipitating with ethanol. Mp. 218°–225° (with decomposition); $[\alpha]_D = +23 \pm 1°$ (c=3.002; in water); CS: $R_{f25A}=0.05$, $R_{f101}=0.33$, $R_{f101A}=0.28$.

The starting material can be obtained as follows:

(b) (2S)-N-BOC-serine tert.-butyl ester is obtained from (2S)-N-BOC-serine (Mp. 85°–95°, $[\alpha]_D = +3 \pm 1°$ (c=3; in methanol)) by reacting with O-tert.-butylisourea in methylene chloride [(E. Vowinkel, Chem. Ber. 100, 16 (1967)]. Mp. 95°–103°. $[\alpha]_D = +7 \pm 1°$ (c=4.96, in chloroform).

(c) A solution of 12.1 g of (2S)-N-BOC-serine tert.-butyl ester in 125 ml of methylene chloride is cooled to 0°, 30 ml of phosgene solution (20% in toluene) are added and subsequently a mixture of 5 ml of pyridine and 20 ml of methylene chloride are added dropwise over a period of 30 minutes while stirring and cooling at +5° to +10°. The suspension is stirred for 90 minutes in an ice bath and then a solution of 13.0 g of 4-aminophenylacetic acid benzyl ester in 50 ml of methylene chloride and 6 ml of pyridine is added dropwise over a period of 20 minutes at 0° to +5°, and the reaction mixture is stirred at room temperature for 3 hours. The suspension is diluted with methylene chloride, and washed in succession with water, 10% citric acid, water, 1N sodium bicarbonate solution and water. The organic phase is dried over sodium sulphate and the methylene chloride is evaporated off in a rotary evaporator at 50°. The 4-((2S)-2-BOC-amino-2-tert.-butoxycarbonylethoxycarbonylamino)phenylacetic acid benzyl ester obtained is purified over silica gel and recrystallised from petroleum ether/ethyl acetate (20:1). Mp. 74°–75°; $[\alpha]_D = +21 \pm 1°$ (c=3.02, in chloroform).

(d) A solution of 13.0 g of 4-((2S)-2-BOC-amino-2-tert.-butoxycarbonylethoxycarbonylamino)phenylacetic acid benzyl ester in 200 ml of ethyl acetate is hydrogenated in the presence of 1.50 g of palladium on activated carbon (10%). The catalyst is filtered off, washed with ethyl acetate, the filtrate is concentrated in a rotary evaporator at 50° and the 4-((2S)-2-BOC-amino-2-tert.-butoxycarbonylethoxycarbonylamino)-phenylacetic acid is crystallised by adding petroleum ether. Mp. 150°–156°; $[\alpha]_D = +37 \pm 1°$ (c=2.96, in chloroform).

(e) A solution of 7.50 g of 7β-amino-3-[(1-methyl-1H-tetrazol-5-yl)thiomethyl]-3-cephem-4-carboxylic acid diphenylmethyl ester and 7.0 g of 4-((2S)-2-BOC-amino-2-tert.-butoxycarbonylethoxycarbonylamino)-phenylacetic acid in a mixture of 50 ml of tetrahydrofuran and 15 ml of N,N-dimethylformamide is cooled with an ice bath to +5°, a solution of 3.0 g of N,N'-dicyclohexyl carbodiimide in 20 ml of tetrahydrofuran is added dropwise over a period of 20 minutes while stirring and cooling, then the ice bath is removed and the reaction mixture is stirred at room temperature. After a reaction time of 3 hours, a further 2.0 g of solid N,N'-dicyclohexyl carbodiimide is added to the suspension. After stirring for a total of 6.5 hours, the suspension is suction-filtered off, the filtered material is washed with tetrahydrofuran a large amount of ethyl acetate is added to the filtrate and the tetrahydrofuran is removed by concentrating in a rotary evaporator at 45°. The resulting solution is diluted with ethyl acetate, washed in succession with water, 1N sodium bicarbonate solution and water, the organic phase is separated off, dried over sodium sulphate and concentrated by evaporation in a rotary evaporator at 45°. The remaining foam is purified by chromatography over 20 times the amount of silica gel. The fractions with methylene chloride/methyl acetate (7:1) and (5:1) as eluant are combined and the 7β-(2-[4-{(2S)-2-BOC-amino-2-tert.-butoxycarbonylethoxycarbonylamino)phenyl]acetylamino}-3-[(1-methyl-1H-tetrazol-5-yl)thiomethyl]-3-cephem-4-carboxylic acid diphenylmethyl ester is crystallised from a little ethyl acetate. Mp. 125°–132°. CS (solvent: toluene/chloroform/ethyl acetate/ethanol (16:16:16:1): $R_f=0.50$.

EXAMPLE 3

(a) A mixture of 4.0 g of 7β-{2-[4-((2R)-2-BOC-amino-2-tert.-butoxycarbonylethoxycarbonylamino)-phenyl]acetylamino}-3-methyl-3-cephem-4-carboxylic acid diphenylmethyl ester, 3.2 ml of anisole, 4.0 ml of methylene chloride and 40 ml of trifluororacetic acid is stirred for 1.5 hours at room temperature with the exclusion of atmospheric moisture. A voluminous precipitate is precipitated from the initially clear solution. The suspension is poured onto an ice-cold mixture of petroleum ether (500 ml) and ether (250 ml), the resulting trifluoroacetate is suction-filtered off, washed with ether and dried under a high vacuum at room temperature. The 7β-{2-[4-((2R)-2-amino-2-carboxyethoxycarbonylamino)phenyl]acetylamino}-3-methyl-3-cephem-4-carboxylic acid sodium salt is obtained from the trifluoroacetate in accordance with the process in Example 1. The sodium salt is purified by dissolving and reprecipitating from aqueous solution with ethanol. Mp. 211°–216° (with decomposition); CS: $R_{f52A}=0.17$, $R_{f101}=0.34$, $R_{f101A}=0.25$.

The starting material can be produced as follows:

(b) A solution of 5.0 g of 7β-amino-3-methyl-3-cephem-4-carboxylic acid diphenylmethyl ester and 5.75 g of 4-((2R)-2-BOC-amino-2-tert.-butoxycarbonylethoxycarbonylamino)phenylacetic acid in 50 ml of tetrahydrofuran is reacted with a solution of 2.7 g of N,N'-dicyclohexyl carbodiimide in 10 ml of tetrahydrofuran and with 1.5 g of solid N,N'-dicyclohexyl carbodiimide in accordance with the process of Example 1. The crude product is purified by chromatography over 15 times the amount of silica gel. The fractions with methylene chloride/methyl acetate (9:1) as eluant are combined and the 7β-{2-[4-((2R)-2-BOC-amino-2-tert.-butoxycarbonylethoxycarbonylamino)phenyl]acetylamino}-3-methyl-3-cephem-4-carboxylic acid diphenylmethyl ester is precipitated from ethyl acetate solution with a mixture of petroleum ether and ether. CS (solvent: toluene/chloroform/ethyl acetate/ethanol (33:33:33:1): $R_f=0.32$.

EXAMPLE 4

(a) A mixture of 2.3 g of 7β-{2-[4-((2R)-2-BOC-amino-2-tert.-butoxycarbonylethoxycarbonylamino)-phenyl]acetylamino}cephalosporanic acid diphenylmethyl ester, 1.5 g of anisole, 15 ml of methylene chloride and 120 ml of trifluoroacetic acid is stirred for one hour at room temperature with the exclusion of atmospheric moisture. The suspension is concentrated at 40° in a rotary evaporator in a period of 15 minutes to approximately 50 ml and poured onto an ice-cold mixture of petroleum ether (500 ml) and ether (250 ml). The resulting trifluoroacetate is suction-filtered off, washed with ether and dried at room temperature under a high vacuum.

The 7β-{2-[4-((2R)-2-amino-2-carboxyethoxycarbonylamino)phenyl]acetylamino}cephalosporanic acid sodium salt is obtained from the trifluoroacetate in accordance with the process of Example 1. Mp. 166°–170° (with decomposition). CS: $R_{f52A}=0.07$, $R_{f101}=0.34$, $R_{f101A}=0.46$.

The starting material can be produced as follows:

(b) A solution of 5.0 g of 7β-aminocephalosporanic acid diphenylmethyl ester and 5.0 g of 4-((2R)-2-BOC-amino-2-tert.-butoxycarbonylethoxycarbonylamino)-phenylacetic acid in 50 ml of tetrahydrofuran is reacted with a solution of 2.35 g of N,N'-dicyclohexyl carbodiimide in 10 ml of tetrahydrofuran and with 1.18 g of solid N,N'-dicyclohexyl carbodiimide in accordance with the process of Example 1. The crude product is purified by chromatography over 20 times the amount of silica gel. The fractions with methylene chloride/methyl acetate (9:1) and (5:1) as eluant are combined and the 7β-{2-[4-((2R)-2-BOC-amino-2-tert.-butoxycarbonylethoxycarbonylamino)phenyl]acetylamino}cephalosporanic acid benzyl ester is precipitated from ethyl acetate solution with a mixture of petroleum ether and ether. CS (solvent: toluene/chloroform/ethyl acetate/ethanol (33:33:33:1); $R_f=0.28$.

EXAMPLE 5

(a) A mixture of 3.7 g of 7β-{2-[4-((2R)-2-BOC-amino-2-tert.-butoxycarbonylethoxycarbonylamino)phenyl]acetylamino}-3-carbamoyloxymethyl-3-cephem-4-carboxylic acid diphenylmethyl ester, 3.0 ml of anisole, 4.0 ml of methylene chloride and 40 ml of trifluoroacetic acid is stirred for 1 hour at room temperature with the exclusion of atmospheric moisture. The suspension is then poured onto an ice-cold mixture of petroleum ether (800 ml) and ether (400 ml), the resulting trifluoroacetate is suction-filtered off, washed with diethyl ether and dried under a high vacuum at room temperature.

The 7β-{2-[4-((2R)-2-amino-2-carboxyethoxycarbonylamino)phenyl]acetylamino}-3-carbamoyloxymethyl-3-cephem-4-carboxylic acid sodium salt is obtained from the above trifluoroacetate in accordance with the process of Example 1. Mp. 237°–242° (with decomposition). CS: $R_{f52A}=0.07$; $R_{f101}=0.30$.

The starting material can be produced as follows:

(b) A solution of 5.0 g of 7β-amino-3-carbamoyloxy-3-cephem-4-carboxylic acid diphenylmethyl ester and 4.9 g of 4-((2R)-2-BOC-amino-2-tert.-butoxycarbonylethoxycarbonylamino)-phenylacetic acid in 50 ml of tetrahydrofuran is reacted with a solution of 2.8 g of N,N'-dicyclohexyl carbodiimide in 10 ml of tetrahydrofuran and with 1.5 g of solid N,N'-dicyclohexyl carbodiimide in accordance with the process of Example 1. The crude product is purified by chromatography over 30 times the amount of silica gel. The fractions with methylene chloride/methyl acetate (7:3) and (3:2) as eluant are combined and the 7β-{2-[4-((2R)-2-BOC-amino-2-tert.butoxycarbonylethoxycarbonylamino)phenyl]acetylamino}-3-carbamoyloxymethyl-3-cephem-4-carboxylic acid diphenylmethyl ester is precipitated from ethyl acetate solution with a mixture of petroleum ether and ether. Mp. 95°–114° (with a slow decomposition); CS (solvent: ethyl acetate/toluene/ethanol (47:47:5)): $R_f=0.34$.

The compound obtained according to example 5(a) may also be produced as follows:

(ai) 130 ml of trifluoroacetic acid are added at 0° to a suspension of 24 g of 7β-{2-[4-((2R)-2-BOC-amino-2-diphenylmethoxycarbonylethoxycarbonylamino)phenyl]acetylamino}-3-carbamoyloxymethyl-3-cephem-4-carboxylic acid diphenylmethyl ester in 130 ml of methylene chloride and 6.6 ml of anisole, and the resulting clear solution is stirred for 45 minutes at 0°. By adding 740 ml of diethyl ether/hexane (1:1), the trifluoroacetate of the 7β-{2-[4-((2R)-2-amino-2-carboxyethoxycarbonylamino)phenyl]acetylamino}-3-carbamoyloxymethyl-3-cephem-4-carboxylic acid is precipitated. The precipitate is suction-filtered off, dissolved in 140 ml of water and the solution is adjusted to a pH of 5.5 by adding 1N sodium bicarbonate and filtered. The clear filtrate, concentrated by evaporation in vacuo, produces a residue which is digested with ethanol to form an almost colourless powder, which is suction-filtered off and dried. The sodium salt of 7β-{2-[4-((2R)-2-amino-2-carboxyethoxycarbonylamino)phenyl]acetylamino}-3-carbamoyloxymethyl-3-cephem-4-carboxylic acid is obtained; $[α]_D^{20}=+110±1°$ (c=3, H$_2$O); $[α]_D^{20}=+90±1°$ (c=3, 0.1N sodium bicarbonate). CC: $R_{f101}=0.38$.

The starting material can be obtained as follows:

(c) A suspension of 100 g of (2R)-serine in 1 l of water is made into a solution by the slow addition of 100 g of solid, anhydrous sodium carbonate, then 2 l of dioxan and 346 g of di-tert.-butyl pyrocarbonate are added and the mixture is stirred for 30 minutes at +20°. The dioxan is evaporated off in vacuo and the aqueous phase is extracted at 0° and a pH of 2 with ethyl acetate. 236.7 g of amorphous, crude (2R)-N-BOC-serine, that contains approximately 195 g of pure product, are obtained. The pure compound can be obtained therefrom by triturating with petroleum ether and cooling: Mp 78°–83° (with decomposition).

(d) To a solution of 236.7 g of the resulting crude (2R)-N-BOC-serine in 700 ml of methylene chloride, a solution of approximately 214 g of diphenyl diazomethane in 1 liter of methylene chloride is added dropwise at 22° while cooling, and the mixture is stirred for 1½ hours at 20°. The mixture is concentrated by evaporation in vacuo, the residue is taken up in ethyl acetate and washed at 0° with a phosphate buffer of a pH of 2.0 and then of a pH of 7.0. The dried organic phase yields, on concentration by evaporation, a crystalline residue which is digested in hexane, and after filtration the (2R)-N-BOC-serine diphenylmethyl ester is obtained: Mp. 116°–117° (corrected). $[α]_D^{20}=+6±1°$ (c=1, chloroform).

(e) A suspension of 46.4 g of (2R)-N-BOC-serine diphenylmethyl ester in 340 ml of absolute methylene chloride is added dropwise at 0°, to a mixture of 62 ml of 20% phosgene in toluene and 10 ml of pyridine, and the mixture is stirred for 1 hour at 0° (solution A).

37.5 ml of trimethylchlorosilane are added to a suspension of 18.9 g of p-aminophenylacetic acid in 75 ml of pyridine, whereby with spontaneous heating to 33° a clear solution results. After stirring for 15 minutes the solution is diluted with 70 ml of methylene chloride and stirring is carried out for a further 15 minutes (solution B).

At 0°, solution B is added dropwise over a period of 3 minutes to solution A, and the mixture is then stirred for 30 minutes at 0° and for 30 minutes at +20°. The mixture is stirred with 1.3 l of 0.3M of phosphate buffer, pH 7, and is extracted at a pH of 6 with ethyl acetate. The dried and concentrated organic phase is digested with toluene and after filtration yields 4-((2R)-2-BOC-amino-2-diphenylmethoxycarbonylethoxycarbonylamino)phenylacetic acid; Mp. 165°–166° (corrected), $[\alpha]_D^{20} = +2\pm1°$ (c=1, chloroform).

(f) 8.8 g of chloroformic acid isobutyl ester are added at 0° to a suspension of 38.4 g of 4-((2R)-2-BOC-amino-2-diphenylmethoxycarbonylethoxycarbonylamino)-phenylacetic acid and 7.1 g of N-methylmorpholine in 500 ml of absolute methylene chloride, and the mixture is then stirred for 90 minutes at 0°. This solution of the anhydride is then added dropwise at 0° to a solution of 35.9 g of 3-carbamoyloxymethyl-7-ammonium-3-cephem-4-carboxylic acid diphenylmethyl ester tosylate and 7.1 g of N-methylmorpholine in 300 ml of methylene chloride and the mixture is stirred for 45 minutes at 22°. The mixture is stirred into 600 ml of 0.5M dipotassium hydrogen phosphate buffer. After distilling off the methylene chloride in vacuo, extraction is carried out in the cold with ethyl acetate. The organic phase is washed with phosphate buffer of a pH of 2.0, dried, concentrated in vacuo and yields the 7β-{2-[4-((2R)-2-BOC-amino-2-diphenylmethoxycarbonylethoxycarbonylamino)phenyl]acetylamino}-3-carbamoyloxymethyl-3-cephem-4-carboxylic acid diphenylmethyl ester; Mp. 167°–169°; $[\alpha]_D^{20} = +46\pm1°$ (c=3 dimethyl sulphoxide).

EXAMPLE 6

(a) A mixture of 2.2 g of 7β-{2-[4-((5R,S)-5-BOC-amino-5-tert.-butoxycarbonylphenylaminocarbonylamino)phenyl]acetylamino}-cephalosporanic acid diphenylmethyl ester, 1.9 g of anisole, 15 ml of methylene chloride and 120 ml of trifluoroacetic acid is stirred for 1 hour at room temperature with the exclusion of atmospheric moisture. The suspension is then poured onto an ice-cold mixture of petroleum ether (600 ml) and ether (300 ml), the resulting trifluoroacetate is suction-filtered off, washed with ether and dried at room temperature under a high vacuum.

The 7β-{2-[4-((5R,S)-5-amino-5-carboxypentylaminocarbonylamino)phenyl]acetylamino}-cephalosporanic acid sodium salt is obtained from the above trifluoroacetate in accordance with the process of Example 1. Mp. 248°–255° (with decomposition): cs: $R_{fS2A}=0.05$, $R_{f101}=0.32$, $R_{f101A}=0.47$.

The starting material can be produced as follows:

(b) The oily (2R,S)-$N^2$-BOC-$N^6$-Z-lysine tert.-butyl ester is obtained from (2R,S)-$N^2$BOC-$N^6$Z-lysine by reacting with O-tert.-butylisourea in methylene chloride [(E. Vowinkel, Chem. Ber. 100 16 (1967)]. The crude product is purified by chromatography over 20 times the amount of silica gel, and the fractions with toluene/ethyl acetate (5:1) as eluant are combined. CS (Solvent: toluene/ethyl acetate (2:1)); $R_f=0.56$.

(c) A solution of 30.0 g of (2R,S)-$N^2$-BOC-$N^6$-Z-lysine tert.-butyl ester in 300 ml of methanol is hydrogenated in the presence of 4.0 g of palladium on activated carbon (10%). After approximately 4 hours, the hydrogen absorption comes to a standstill. The catalyst is filtered off, washed with methanol, and the filtrate is concentrated by evaporation in a rotary evaporator at 50°. The (2R,S)-$N^2$-BOC-lysine tert.-butyl ester is oily.

(d) A mixture of 66 ml of phosgene solution (20% in toluene) and 450 ml of methylene chloride is cooled with an ice bath to 0° and a solution of 36.0 g of (2R,S)-$N^2$-BOC-lysine tert.-butyl ester in 180 ml of methylene chloride and 10 ml of pyridine is added dropwise over a period of 1 hour while stirring and cooling at +5° to +8°. The suspension is stirred in the ice bath for one hour and then a solution of 26.1 g of 4-aminophenylacetic acid benzyl ester in 280 ml of methylene chloride and 22 ml of pyridine is added at 0° to +5°. The reaction mixture is stirred for 2 hours at room temperature. The suspension is diluted with methylene chloride and is washed in succession with water, 10% citric acid, water, 1N sodium bicarbonate solution and water. The organic phase is dried over sodium sulphate and the solvent is evaporated off in a rotary evaporator at 50°. The crude product is purified by chromatography over 25 times the amount of silica gel and the fractions obtained with methylene chloride/methyl acetate (4:1) as eluant are combined. The 4-((5R,S)-5-BOC-amino-5-tert.-butoxycarbonylpentylaminocarbonylamino)-phenylacetic acid benzyl ester is oily. CS (solvent: toluene/chloroform/ethyl acetate/ethanol (3:3:3:0.3): $R_f 0.32$.

(e) A solution of 7.60 g of 4-((5R,S)-5-BOC-amino-5-tert.-butoxycarbonylpentylaminocarbonylamino)-phenylacetic acid benzyl ester in 200 ml of ethyl acetate is hyrogenated in the presence of 1.0 g of palladium on activated carbon (10%). After approximately 2 hours the calculated amount of hydrogen has been absorbed. The catalyst is filtered off, washed with ethyl acetate, the filtrate is concentrated in a rotary evaporator at 45° and the 4-((5R,S)-5-tert.-butoxycarbonylpentylaminocarbonylamino)phenylacetic acid is crystallised by adding petroleum ether. Mp: 121°–124°.

(f) A solution of 4.40 g of 7β-aminocephalosporanic acid diphenylmethyl ester and 4.80 g of 4-((5R,S)-5-BOC-amino-5-tert.-butoxycarbonylpentylaminocarbonylamino)phenylacetic acid in 40 ml of tetrahydrofuran is reacted with a solution of 2.0 g of N,N'-dicyclohexyl carbodiimide in 10 ml of tetrahydrofuran and with 1.0 g of solid N,N'-dicyclohexyl carbodiimide in accordance with the process of Example 1. The crude product is purified by chromatography over 30 times the amount of silica gel. The fractions with methylene chloride/methyl acetate (1:1) are combined and the 7β-{2-[4-((5R,S)-5-BOC-amino-5-tert.-butoxycarbonylpentylaminocarbonylamino)phenyl]acetylamino}-cephalosporanic acid diphenylmethyl ester is precipitated from ethyl acetate solution with a mixture of petroleum ether and ether. Mp. 120°–128° (with decomposition). CS (solvent: toluene/ethanol (12.1)): $R_f=0.17$.

EXAMPLE 7

(a) A mixture of 1.60 g of 7β-{2-[(4-((3R)-3-BOC-amino-3-tert.-butoxycarbonylpropionylamino)phenyl]acetylamino}-3-[(1-methyl-1H-tetrazol-5-yl)thiomethyl]-3-cephem-4-carboxylic acid diphenylmethyl ester, 1.0 g of anisole, 2.50 ml of methylene chloride and 25 ml of trifluoroacetic acid is stirred for 40 minutes at room temperature with the exclusion of atmospheric moisture. The suspension obtained is poured onto an ice-cold mixture of petroleum ether (400 ml) and diethyl ether (200 ml), the resulting trifluoroacetate is suction-filtered off, washed with diethyl ether and dried at room temperature under high vacuum.

The 7β-{2-[4-((3R)-3-amino-3-carboxypropionylamino)phenyl]acetylamino}-3-[(1-methyl-1H-tetrazol-5-yl)thiomethyl]-3-cephem-4-carboxylic acid sodium salt is obtained from the trifluoroacetate in accordance with the process of Example 1. Mp. 248°–252° (with decomposition). CS: $R_{fS2A}=0.09$, $R_{f101}=0.33$, $R_{f101A}=0.28$.

The starting material can be produced as follows:

(b) (2R)-N-BOC-aspartic acid-α-tert.-butyl ester is obtained by hydrolysing (2R)-N-BOC-aspartic acid (β-methyl ester)-α-tert.-butyl ester [Mp 50°-51° (with decomposition); $[α]_D = -17 \pm 1°$ (c=2.93 in chloroform)] with 1N sodium hydroxide (P. M. Hardy et al., J. Chem. Soc., Perkin. Trans. 1, 605 (1972)) in acetone. Mp. 96°-100° (with decomposition); $[α]_D = -15 \pm 1°$ (c=2.88 in chloroform).

(c) A solution of 10.0 g of (2R)-N-BOC-aspartic acid α-tert.-butyl ester and 8.35 g of 4-aminophenylacetic acid benzyl ester in 125 ml of tetrahydrofuran is cooled with an ice bath of +5°, a solution of 7.15 g of N,N'-dicyclohexyl carbodiimide in 30 ml of tetrahydrofuran is added dropwise over a period of 20 minutes while stirring and cooling, then the ice bath is removed and the reaction mixture is stirred at room temperature. After a reaction time of 3 hours, 4.0 g of solid N,N'-dicyclohexyl carbodiimide is added to the reaction mixture. After stirring for a total of 7 hours, the suspension is suction-filtered off, the filtered material is washed with ethyl acetate, a large amount of ethyl acetate is added to the filtrate and the tetrahydrofuran is removed by concentration in a rotary evaporator at 45°. The solution obtained is diluted with ethyl acetate and washed in succession with water, 1N sodium bicarbonate solution and water. The organic phase is dried over sodium sulphate and concentrated by evaporation in a rotary evaporator at 45°. The resulting 4-((3R)-3-BOC-amino-3-tert.-butoxycarbonylpropionylamino)phenylacetic acid benzyl ester is recrystallized from a mixture of benzene and petroleum ether. Mp. 130°-133° (with decomposition); $[α]_D = -15 \pm 1°$ (c=1.51 in chloroform).

(d) A solution of 12.2 g of 4-((3R)-3-BOC-amino-3-tert.-butoxycarbonylpropionylamino)phenylacetic acid benzyl ester in a mixture of ethyl acetate (360 ml) and ethanol (40 ml) is hydrogenated in the presence of 4.0 g of palladium on activated carbon (10%) at room temperature. After approximately 1 hour the calculated quantity of hydrogen has been absorbed. The catalyst is filtered off, washed with a mixture of ethyl acetate/ethanol (9:1) and the filtrate is concentrated by evaporation in a rotary evaporator at 45°. The 4-((3R)-3-BOC-amino-3-tert.-butoxycarbonylpropionylamino)phenylacetic acid is precipitated by mixing with petroleum ether. Mp. 160°-166° (with decomposition); $[α]_D = +2 \pm 1°$ (c=1.92, in methanol).

(e) A solution of 5.0 g of 7β-amino-3-[(1-methyl-1H-tetrazol-5-yl)thiomethyl]-3-cephem-4-carboxylic acid diphenylmethyl ester and 4.40 g of 4-((3R)-3-BOC-amino-3-tert.-butoxycarbonylpropionylamino)phenylacetic acid in a mixture of 30 ml of tetrahydrofuran and 10 ml of N,N-dimethylformamide is reacted with a solution of 2.5 g of N,N'-dicyclohexyl carbodiimide in 10 ml of tetrahydrofuran and 2.0 g of solid N,N'-dicyclohexyl carbodiimide in accordance with the process of Example 1. The crude product is purified by chromatography over 20 times the amount of silica gel. The fractions with methylene chloride/methyl acetate (4:1) are combined and the 7β-{2-[4-((3R)-3-BOC-amino-3-tert.-butoxycarbonylpropionylamino)phenyl]acetylamino}-3-[(1-methyl-1H-tetrazol-5-yl)thiomethyl]-3-cepehm-4-carboxylic acid diphenylmethyl ester is crystallised from ethyl acetate. Mp. 155°-160° (with decomposition); CS (solvent: toluene/ethyl acetate/chloroform/ethanol (16:16:16:1)): $R_f = 0.26$.

EXAMPLE 8

(a) A mixture of 1.80 g of 7β-{2-[4-((3R)-3-BOC-amino-3-tert.-butoxycarbonylpropionylamino)phenyl]acetylamino}-3-carbamoyloxymethyl-3-cephem-4-carboxylic acid diphenylmethyl ester, 0.8 ml of anisole and 20 ml of trifluoroacetic acid is stirred for 1 hour at room temperature with the exclusion of atmospheric moisture. The suspension is poured onto an ice-cold mixture of petroleum ether (400 ml) and diethyl ether (200 ml), the resulting trifluoroacetate is suction-filtered off, washed with diethyl ether and dried at room temperature under a high vacuum. The 7β-{2-[4-((3R)-3-amino-3-carboxypropionylamino)phenyl]acetylamino}-3-carbamoyloxymethyl-3-cephem-4-carboxylic acid sodium salt is obtained from the trifluoroacetate in accordance with the process of Example 1. Mp. 250°-254° (with decomposition); CS: $R_{f524} = 0.045$, $R_{f101} = 0.25$, $R_{f101A} = 0.17$.

The starting material can be produced as follows:

(b) A solution of 5.0 g of 7β-amino-3-carbamoyloxymethyl-3-cephem-4-carboxylic acid diphenylmethyl ester and 4.90 g of 4-((3R)-3-BOC-amino-3-tert.-butoxycarbonylpropionylamino)phenylacetic acid in a mixture of 40 ml of tetrahydrofuran and 40 ml of methylene chloride is reacted with a solution of 3.0 g of N,N'-dicyclohexyl carbodiimide and 1.50 g of solid N,N'-dicyclohexyl carbodiimide in 20 ml of tetrahydrofuran in accordance with the process of Example 1. After a reaction time of 7.5 hours, the suspension is suction-filtered off, the filtered material is washed with a mixture of ethyl acetate/methyl acetate (1:1) and the filtrate is concentrated in a rotary evaporator at 45°. The solution is diluted with a large amount of ethyl acetate/methyl acetate (1:1) and washed in succession with water, 1N sodium bicarbonate solution and water. The organic phase is dried over sodium sulphate. By concentrating the solution in a rotary evaporator at 45°, the solid 7β-{2-[4-((3R)-3-BOC-amino-3-tert.-butoxycarbonylpropionylamino)phenyl]-acetylamino}-3-carbamoyloxymethyl-3-cephem-4-carboxylic acid diphenylmethyl ester is precipitated. The product is suction-filtered off and washed with a small amount of ethyl acetate. Mp. 158°-165° (with decomposition); CS (solvent: ethyl acetate/chloroform/ethanol 12:12:1): $R_f = 0.51$.

EXAMPLE 9

(a) A paste of 1.07 g (1 mmole) of 7β-{2-[5-((2R)-2-BOC-amino-2-diphenylmethoxycarbonylethoxycarbonylaminomethyl)-2-furyl]-2-syn-methoxyiminoacetylamino}-3-[(1-methyl-1H-tetrazol-5-yl)thiomethyl]-3-cephem-4-carboxylic acid diphenylmethyl ester in 3 ml of anisole is cooled to 0°, 12 ml of trifluoroacetic acid are added, and the mixture is stirred for 20 minutes at 0°. Subsequently the process of adding tolune and concentrating by evaporation in vacuo is carried out twice. The residue, containing the trifluoroacetate of the end product, is taken up in ethyl acetate/water and the organic phase is separated off. The aqueous phase is adjusted to a pH of 6.1 with 1N sodium hydroxide solution, concentrated in vacuo to approximately 1.5 ml and 60 ml of ethanol are added, whereupon the sodium salt of 7β-{2-[5-((2R)-2-amino-2-carboxyethoxycarbonylaminomethyl)-2-furyl]-2-syn-methoxyiminoacetylamino}-3-[(1-methyl-1H-tetrazol-5-yl)thiomethyl]-3-cephem-4-carboxylic acid is precipitated. CS: $R_{f524} = 0.05$.

The starting material can be produced as follows:

(b) 150 ml of trifluoroacetic acid are added dropwise, while cooling with ice, to 50 g (0.51 mole) of furfurylamine. The solution is warmed to 45°, 150 ml of acetic anhydride are added dropwise and the mixture is then stirred for 3 hours at 50°–55° and overnight at room temperature. The mixture is concentrated in vacuo and the process of adding toluene and concentrating by evaporation in vacuo is carried out a further two times. The crystallising 2-acetyl-5-trifluoroacetylaminomethylfuran is filtered off and washed with diethyl ether. Mp. 96°; IR-spectrum (in CHCl₃): absorption bands at 2.90, 3.03, 5.78, 5.97 and 6.57μ.

(c) A solution of 100 g (0.42 mole) of 2-acetyl-5-trifluoroacetylaminomethylfuran and 72 g (0.65 mole) of selenium dioxide in 300 ml pyridine is carefully heated, while stirring well, to 85°, and is stirred at 90° for 3 hours. It is then filtered through Celite, the filtrate is concentrated in vacuo, the residue is taken up in ethyl acetate and washed with dilute sulphuric acid and saturated sodium chloride solution. After drying the organic phase over sodium sulphate, it is concentrated to dryness and the resulting 2-(5-trifluoroacetylaminoethyl-2-furyl)-2-oxoacetic acid is purified by chromatography over silica gel (system: methylene chloride/ethyl acetate 9:1). IR-spectrum (dioxan): absorption bands at 3.08, 5.67, 5.81, 5.98 and 6.45μ; CS: $R_{f524}=0.35$; Mp. 126°–128°.

(d) 8.07 ml of pyridine (102 mmole) and 8.5 g of O-methylhydroxylamine hydrochloride (102 mmole) are added to a suspension of 27 g (102 mmole) of 2-(5-trifluoroacetylaminomethyl-2-furyl)-2-oxoacetic acid in 250 ml of methanol. The solution obtained is stirred for 1½ hours at room temperature under nitrogen, is then concentrated to dryness in vacuo, the residue is taken up in ethyl acetate and the solution is washed with dilute sulphuric acid and saturated sodium chloride solution. The organic phase is dried over sodium sulphate and concentrated. The 2-(5-trifluoroacetylaminomethyl-2-furyl)-2-syn-methoxyiminoacetic acid is isolated in the form of a partially crystallising foam (more than 85% syn-isomer). The pure syn-isomer is obtained by recrystallisation from ethyl acetate/hexane. Mp. 115°–117°; IR-spectrum (Nujol): absorption bands at 3.2, 5.67, 5.82 and 6.36, μ; CS: $R_f=0.41$ (n-butanol/acetic acid/water (67:10:23)).

(e) A solution of 31 g (102 mmole) of 2-(5-trifluoroacetylaminomethyl-2-furyl)-2-syn-methoxyiminoacetic acid in 150 ml of water and 200 ml of dioxan is stirred for 1 hour at room temperature with 27 ml (202 mmole) of 7.5N sodium hydroxide solution. The solution is adjusted to a pH of 6 and concentrated in vacuo to 30 ml. The crystallised zwitter ion of the 2-(5-aminomethyl-2-furyl)-2-syn-methoxyiminoacetic acid is filtered off and washed with acetone. Mp. 230° (with decomposition). IR-spectrum (Nujol): absorption bands at 3.25, 6.12, 6.29 and 6.52μ; CS: $R_{f524}=0.1$.

(f) A solution of 560 mg (1.5 mmole) of (2R)-N-BOC-serine diphenylmethyl ester (produced from (2R)-N-BOC-serine and diphenyldiazomethane) in 10 ml of methylene chloride is cooled to 0° and in succession 0.12 ml (1.5 mmole) of pyridine and 0.72 ml of phosgene (20% in toluene) are added. The solution is stirred at 0° under nitrogen for 1 hour (solution I).

0.93 ml of bis-trimethylsilylacetamide (3.75 mmole) is added to a suspension of 250 mg (1.25 mmole) of 2-(5-aminomethyl-2-furyl)-2-syn-methoxyiminoacetic acid in 1 ml of acetonitrile, then the mixture is stirred for ¾ hour at room temperature under nitrogen (solution II).

Solution II is now pipetted into solution I and after adding 0.2 ml (1.4 mmole) of triethylamine the mixture is stirred for 1½ hours. After shaking with 2N sulphuric acid and sodium chloride solution the organic phase is dried over sodium sulphate and concentrated in vacuo. The oily residue is chromatographed over silica gel (system: methylene chloride/ethyl acetate 9:1).

The 2-[5-((2R)-2-BOC-amino-2-diphenylmethoxycarbonylethoxycarbonylaminomethyl)-2-furyl]-2-syn-methoxyiminoacetic acid is isolated in the form of a foam. IR-spectrum (in CHCl₃): absorption bands at 2.94, 5.78, 5.84, 5.95, 6.15 and 6.66μ. CS: $R_{f524}=0.53$.

(g) A solution of 10 g (16.8 mmole) of 2-[5-((2R)-2-BOC-amino-2-diphenylmethoxycarbonylethoxycarbonylaminomethyl)-2-furyl]-2-syn-methoxyiminoacetic acid in 50 ml of methylene chloride is cooled to −20°, and 1.87 ml (16.8 mmole) of N-methylmorpholine and 1.9 ml (14 mmole) of chloroformic acid isobutyl ester are added. After a reaction time of 1½ hours at −15°, 6.92 g of 7β-amino-3-[(1-methyl-1H-tetrazol-5-yl)thiomethyl]-3-cephem-4-carboxylic acid diphenylmethyl ester are added and the solution is brought to a temperature of 0°. After 3 hours the reaction mixture is washed in succession with 2N sulphuric acid, dilute aqueous sodium bicarbonate solution and concentrated, aqueous sodium chloride solution, dried over sodium sulphate, filtered and concentrated by evaporation. By chromatography of the residue over silica gel (system: toluene/ethyl acetate 3:1) the 7β-{2-[5-((2R)-BOC-amino-2-diphenylmethoxycarbonylethoxycarbonylaminomethyl)-2-furyl]-2-syn-methoxyiminoacetylamino}-3-[(1-methyl-1H-tetrazol-5-yl)thiomethyl]-3-cephem-4-carboxylic acid diphenylmethyl ester is isolated in a pure form. IR-spectrum (CHCl₃): absorption bands at 2.92, 5.61, 5.74, 5.84 and 6.66μ; CS: $R_f=0.41$ (toluene/ethyl acetate 1:1).

The same compound may also be produced as follows:

(h) 27 ml (202 mmole) of 7.5N sodium hydroxide solution are added to a solution of 31 g (102 mmole) of 2-(5-trifluoroacetylaminomethyl-2-furyl)-2-syn-methoxyiminoacetic acid in 150 ml of water and 200 ml of dioxan and the mixture is stirred for 1 hour at room temperature. 32.4 g (306 mmole) of sodium carbonate and 66.7 (306) mmole of di-tert.-butyl pyrocarbonate are added and the mixture is stirred thoroughly at room temperature for 2½ hours. The solution is concentrated and the residue is dissolved in ethyl acetate/water. The aqueous phase is separated off, adjusted to a pH of 2.4 with concentrated phosphoric acid and extracted with ethyl acetate. After drying the organic phase over sodium sulphate and concentrating the solution in vacuo the 2-(5-BOC-aminomethyl-2-furyl)-2-syn-methoxyiminoacetic acid is obtained in the form of an amorphous residue. IR-spectrum (in CHCl₃): absorption bands at 2.99, 3.10, 5.88, and 6.71μ; CS $R_{f524}=0.48$.

(i) A solution of 5 g (16.8 mmole) of 2-(5-BOC-aminomethyl-2-furyl)-2-syn-methoxyiminoacetic acid in 50 ml of methylene chloride is cooled to −20°, and 1.87 ml (16.8 mmole) of N-methylmorpholine and 1.90 ml (14 mmole) of chloroformic acid isobutyl ester are added. After a reaction time of 1½ hours at −15°, 6.92 g of 7β-amino-3-[(1-methyl-1H-tetrazol-5-yl)thiomethyl]-3-cephem-4-carboxylic acid diphenylmethyl ester are added and the solution is brought to 0°. After 3 hours the solution is washed in succession with 2N sulphuric acid, dilute aqueous sodium bicarbonate solution and concentrated aqueous sodium chloride solution. The organic phase is dried over sodium sulphate, filtered and concentrated by evaporation. The residue is chromatographed over silica gel (system: hexane/toluene/acetone 3:4:2) and yields pure amorphous 7β-[2-(5-

BOC-aminomethyl-2-furyl)-2-syn-methoxyiminoacetylamino]-3-[(1-methyl-1H-tetrazol-5-yl)thiomethyl]-3-cephem-4-carboxylic acid diphenylmethyl ester. IR-spectrum (in CHCl₃): absorption bands at 2.89, 2.94, 5.58 5.84 and 6.66μ; CS: R$_f$=0.11 (hexane/toluene/acetone 3:4:2); R$_f$=0.1 (toluene/ethyl acetate 3:1).

(j) A solution of 1.7 g (2.2 mmole) of 7β-[2-(5-BOC-aminomethyl-2-furyl)-2-syn-methoxyiminoaceylamino]-3-[(1-methyl-1H-tetrazol-5-yl)thiomethyl]-3-cephem-4-carboxylic acid diphenylmethyl ester and 0.83 g (4.4 mmole) of p-toluenesulphonic acid (monohydrate) in 17 ml of acetonitrile is stirred for 2½ hours at room temperature, then concentrated in vacuo and the residue is taken up in ethyl acetate and water. The organic phase is washed with sodium bicarbonate solution and sodium chloride solution, dried over sodium sulphate and concentrated to dryness. The 7β-[2-(5-aminomethyl-2-furyl)-2-syn-methoxyiminoacetylamino]-3-[(1-methyl-1H-tetrazol-5-yl)thiomethyl]-3-cephem-4-carboxylic acid diphenylmethyl ester is taken up in approximately 15 ml of methylene chloride (solution I).

0.188 ml (2.64 mmole) of pyridine and 1.43 ml of phosgene in toluene (20% strength) (2.64 mmole) are added to a solution of 0.98 g (2.64 mmole) of (2R)-N-BOC-serine diphenylmethyl ester in 17 ml of methylene chloride at 0° and the mixture is stirred for 1¾ hours at 0° under nitrogen (solution II).

Solution I is added to solution II and the mixture is stirred for 1 hour at 0° under nitrogen. After shaking with 2N sulphuric acid, sodium bicarbonate solution and sodium chloride solution, the organic phase is dried over sodium sulphate, filtered and concentrated by evaporation in vacuo. The residue is purified by chromatography over silica gel (system: toluene/ethyl acetate 3:1) and yields 7β-{2-[5-((2R)-2-BOC-amino-2-diphenylmethoxycarbonylethoxycarbonylaminomethyl)-2-furyl]-2-syn-methoxyiminoacetylamino}-3-[(1-methyl-1H-tetrazol-5-yl)thiomethyl]-3-cephem-4-carboxylic acid diphenylmethyl ester (colourless foam). IR-spectrum (in CHCl₃): absorption bands at 2.92, 5.61, 5.74, 5.86 and 6.66μ; CS: R$_f$=0.41 (toluene/ethyl acetate 1:1).

EXAMPLE 10

(a) A paste of 0.36 g (0.35 mmole) of 7β-{2-[5-((2R)-2-BOC-amino-2-diphenylmethoxycarbonylethoxycarbonylaminomethyl)-2-furyl]-2-syn-methoxyiminoacetylamino}-3-carbamoyloxymethyl-3-cephem-4-carboxylic acid diphenylmethyl ester in 1 ml of anisole is cooled to 0°, 4 ml of trifluoroacetic acid are added and the mixture is stirred for 20 minutes at 0°. Subsequently the process of adding toluene and concentrating in vacuo is carried out twice. The residue, containing the trifluoroacetate of the end product, is taken up in ethyl acetate/water and the organic phase is separated off. The aqueous phase is adjusted to a pH of 6.1 with 1N sodium hydroxide solution, concentrated in vacuo to approximately 1 ml and ethanol (approximately 20 ml) is added, whereupon the sodium salt of 7β-{2-[5-((2R)-2-amino-2-carboxyethoxycarbonylaminomethyl)-2-furyl]-2-syn-methoxyiminoacetylamino}-3-carbamoyloxymethyl-3-cephem-4-carboxylic acid is precipitated. CS: R$_{f52A}$=0.05.

The starting material can be produced as follows:

(b) In succession, at −15°, 0.385 ml (3.45 mmole) of N-methylmorpholine and 0.39 ml (2.88 mmole) of chloroformic acid isobutyl ester are added to a solution of 2.05 g (3.45 mmole ) of 2-[5-((2R)-2-BOC-amino-2-diphenylmethoxycarbonylethoxycarbonylaminomethyl)-2-furyl]-2-syn-methoxyiminoacetic acid in 10 ml of methylene chloride and the mixture is stirred for 1½ hours at −15° C. under nitrogen. After adding 1.26 g (2.88 mmole) of 7β-amino-3-carbamoyloxymethyl-3-cephem-4-carboxylic acid diphenylmethyl ester, the solution is brought to 0° and stirred at this temperature for 2½ hours. The reaction mixture is diluted with methylene chloride, washed in succession with 2N sulphuric acid, sodium bicarbonate solution and sodium chloride solution, dried over sodium sulphate, filtered and concentrated by evaporation. The crude product is chromatographed over silica gel (system: toluene/ethyl acetate 1:1) and yields the pure 7β-{2-[5-((2R)-2-BOC-amino-2-diphenylmethoxycarbonylethoxycarbonylaminomethyl)-2-furyl]-2-syn-methoxyiminoacetylamino}-3-carbamoyloxymethyl-3-cephem-4-carboxylic acid diphenylmethyl ester. IR-spectrum (in CHCl₃): absorption bands at 2.93, 5.58, 5.81 and 6.66μ; CS: R$_f$=0.21 (toluene/ethyl acetate 1:1).

The same compound can also be produced in the following manner:

(c) In succession, at −15°, 3.85 ml (34.5 mmole) of N-methylmorpholine and 3.9 ml (28.8 mmole) of chloroformic acid isobutyl ester are added to a solution of 10.3 g (34.5 mmole) of 2-(5-BOC-aminomethyl-2-furyl)-2-syn-methoxyiminoacetic acid in 100 ml of methylene chloride and the mixture is then stirred for 1½ hours at −15° under nitrogen. After adding 12.6 g (28.8 mmole) of 7β-amino-3-carbamoyloxymethyl-3-cephem-4-carboxylic acid diphenylmethyl ester, the solution is brought to 0° and stirred at this temperature for 2½ hours. The reaction mixture is diluted with methylene chloride, washed in succession with 2N sulphuric acid, sodium bicarbonate solution and sodium chloride solution, dried over sodium sulphate, filtered and concentrated by evaporation. The crude product is chromatographed over silica gel (system: toluene/ethyl acetate 2:1) and yields 7β-[2-(5-BOC-aminomethyl-2-furyl)-2-syn-methoxyiminoacetylamino]-3-carbamoylmethyl-3-cephem-4-carboxylic acid diphenylmethyl ester, which is recrystallised from ethyl acetate/diethyl ether. Mp. 145°−148°; IR-spectrum (CHCl₃): absorption bands at 2.93, 3.00, 5.61, 5.84, 6.33 and 6.66μ; CS: R$_f$=0.1 (toluene/ethyl acetate 2:1).

(d) A solution of 0.8 g (1.11 mmole) of 7β-[2-(5-BOC-aminomethyl-2-furyl)-2-syn-methoxyiminoacetylamino]-3-carbamoyloxymethyl-3-cephem-4-carboxylic acid diphenylmethyl ester and 0.42 g (2.22 mmole) of p-toluenesulphonic acid monohydrate in 8 ml of acetonitrile is stirred for 2½ hours at room temperature, concentrated in vacuo and the residue is taken up in ethyl acetate and water. The organic phase is washed with sodium bicarbonate solution and sodium chloride solution, dried over sodium sulphate and concentrated to dryness. The 7β-[2-(5-aminomethyl-2-furyl)-2-syn-methoxyiminoacetylamino]-3-carbamoyloxymethyl-3-cephem-4-carboxylic acid diphenylmethyl ester obtained in taken up in 5 ml of methylene chloride (solution I).

0.095 ml (1.33 mmole) of pyridine and 0.752 ml of phosgene in toluene (20% strength) (1.33 mmole) are added to a solution of 0.493 g (1.33 mmole) of (2R)-N-BOC-serine diphenylmethyl ester in 9 ml of methylene chloride at 0°, and the mixture is stirred for 1 hour at 0° (solution II).

Solution I is added to solution II and the mixture is allowed to stand for 1 hour at 0° under nitrogen. After shaking with 2N sulphuric acid, sodium bicarbonate solution and sodium chloride solution, the organic phase is dried over sodium sulphate, filtered and concentrated by evaporation in vacuo. The residue is purified by chromatography over silica gel (system: toluene/ethyl acetate 1:1) and yields 7β-{2-[5-((2R)-2-BOC-amino-2-diphenylmethoxycarbonylethoxycarbonylaminomethyl)-2-furyl]-2-syn-methoxyiminoacetylamino}-3-carbamoyloxymethyl-3-cephem-4-carboxylic acid diphenylmethyl ester. IR-spectrum (in CHCl$_3$): absorption bands at 2.93, 5.58, 5,81 and 6.66μ; CS: R$_f$=0.21 (toluene/ethyl acetate 1:1).

EXAMPLE 11

(a) A paste of 1.06 g (1 mmole) of 7β-{2-[5-((2R)-2-BOC-amino-2-diphenylmethoxycarbonylethoxycarbonylaminomethyl)-2-thienyl]-2-syn-2-methoxyiminoacetylamino}-3-acetoxymethyl-3-cephem-4-carboxylic acid diphenylmethyl ester in 3 ml of anisole is cooled to 0°, 12 ml of trifluoroacetic acid are added and the mixture is stirred for 20 minutes at 0°. Subsequently the process of adding toluene and concentrating by evaporation in vacuo is carred out twice. The residue, containing the trifluoroacetate of the end product, is taken up in ethyl acetate/water and the organic phase is separated off. The aqueous phase is adjusted to a pH of 6.1 with 1N sodium hydroxide solution, concentrated in vacuo to approximately 1.5 ml and 60 ml of ethanol are added, whereupon the sodium salt of 7β-{2-[5-((2R)-2-amino-2-carboxyethoxycarbonylaminomethyl)-2-thienyl]-2-syn-methoxyiminoacetylamino}-3-acetoxymethyl-3-cephem-4-carboxylic acid is precipitated. CS: R$_{f52A}$=0.05.

The starting material can be produced as follows:

(b) A solution of 100 g (0.40 mole) of 2-acetyl-5-trifluoroacetylaminomethylthiophene (which can be produced analogously to Example 9b) from 2-aminomethylthiophene, trifluoroacetic acid and acetic anhydride) and 72 g (0.65 mole) of selenium dioxide in 300 ml of pyridine is carefully heated to 85° while stirring well, and is stirred for 3 hours at 90°. Filtration is then carried out through Celite, the filtrate is concentrated in vacuo, the residue is taken up in ethyl acetate and washed with dilute sulphuric acid and saturated sodium chloride solution. After drying the organic phase over sodium sulphate, concentration to dryness is carried out and the 2-(5-trifluoroacetylaminomethyl-2-thienyl)-2-oxoacetic acid is purified by chromatography over silica gel (system: methylene chloride/ethyl acetate 9:1). IR-spectrum (dioxan): absorption bands at 3.08, 5.67, 5.81, 5.90 and 6.45μ; CS: R$_{f52A}$=0.35.

(c) 8.07 ml of pyridine (102 mmole) and 8.5 g of O-methylhydroxylamine hydrochloride (102 mmole) was added to a suspension of 28 g (100 mmole) of 2-(5-trifluoroacetylaminomethyl-2-thienyl)-2-oxoacetic acid in 250 ml of methanol. The solution obtained is stirred for 1½ hours at room temperature under nitrogen, then concentrated to dryness in vacuo, the residue is taken up in ethyl acetate and the solution is washed with dilute sulphuric acid and saturated sodium chloride solution. The organic phase is dried over sodium sulphate and concentrated. The 2-(5-trifluoroacetylaminomethyl-2-thienyl)-syn-methoxyiminoacetic acid is isolated in the form of a foam (approximately 70% syn-isomer). IR-spectrum (Nujol): absorption bands at 3.2, 5.67, 5.82 and 6.36μ; CS: R$_{f52A}$=0.41.

(d) A solution of 31 g (100 mmole) of 2-(5-trifluoroacetylaminomethyl-2-thienyl)-2-syn-methoxyiminoacetic acid in 150 ml of water and 200 ml of dioxan is stirred at room temperature for 1 hour with 27 ml (202) mmole) of 7.5N sodium hydroxide solution. The solution is adjusted to a pH of 6 and concentrated in vacuo to 30 ml. The precipitated zwitter ion of the 2-(5-aminomethyl-2-thienyl)-syn-methoxyiminoacetic acid is filtered off and washed with acetone. IR-spectrum (Nujol): absorption bands at 3.25, 6.12, 6.29 and 6.52μ; CS: R$_{f52A}$=0.1.

(e) A solution of 560 mg (1.5 mmole) of (2R)-N-BOC-serine diphenylmethyl ester (produced from (2R)-N-BOC-serine and diphenyldiazomethane) in 10 ml of methylene chloride is cooled to 0° and 0.12 ml (1.5 mmole) of pyridine and 0.72 ml of phosgene (20% strength in toluene) are added in succession. The solution is stirred at 0° for 1 hour under nitrogen (solution I).

0.93 ml of bis-trimethylsilylacetamide (3.75 mmole) is added to a suspension of 250 mg (1.25 mmole) of 2-(5-aminomethyl-2-thienyl)-2-syn-methoxyiminoacetic acid, and the mixture is stirred for ¾ hour at room temperature under nitrogen (solution II).

Solution II is then pipetted into solution I and after adding 0.2 ml (1.4 mmole) of triethylamine the mixture is stirred for 1½ hours. After shaking with 2N sulphuric acid and sodium chloride solution the organic phase is dried over sodium sulphate and concentrated in vacuo. The oily residue is chromatographed over silica gel (system: methylene chloride/ethyl acetate 9:1).

The 2-[5-((2R)-2-BOC-amino-2-diphenylmethoxycarbonylethoxycarbonylaminomethyl)-2-thienyl]-2-syn-methoxyiminoacetic acid is isolated in the form of a foam. IR-spectrum (in CHCl$_3$): absorption bands at 2.94, 5.78, 5.84, 5,95, 6.15 and 6.66μ; CS: R$_{f52A}$=0.53.

(f) A solution of 10 g (16.0 mmole) of 2-[5-((2R)-2-BOC-amino-2-diphenylmethoxycarbonylethoxycarbonylaminomethyl)-2-thienyl]-2-syn-methoxyiminoacetic acid in 50 ml of methylene chloride is cooled to −20°, and 1.87 ml (16.8 mmole) of N-methylmorpholine and 1.9 ml (14 mmole) of chloroformic acid isobutyl ester are added. After a reaction time of 1½ hours at −15°, 6.92 g of 7β-amino-3-acetylmethyl-3-cephem-4-carboxylic acid diphenylmethyl ester are added and the solution is brought to 0°. After 3 hours the reaction mixture is washed in succession with 2N sulphuric acid, dilute aqueous sodium bicarbonate solution and concentrated aqueous sodium chloride solution, dried over sodium sulphate, filtered and concentrated by evaporation. The 7β-{2-[5-((2R)-2-BOC-amino-2-diphenylmethoxycarbonylethoxycarbonylaminomethyl)-2-thienyl]-2-syn-methoxymonoacetylamino}-3-acetoxymethyl-3-cephem-4-carboxylic acid diphenylmethyl ester is isolated in pure form by chromatography of the residue over silica gel (system: toluene/ethyl acetate 3:1). IR-spectrum (CHCl$_3$): absorption bands at 2.92, 5.61, 5.74, 5.84 and 6.66μ; CS: R$_f$=0.41 (toluene/ethyl acetate 1:1).

The same compound can also be obtained in the following manner:

(g) 27 ml (202 mmole) of 7.5N sodium hydroxide solution are added to a solution of 31 g (100 mmole) of 2-(5-trifluoroacetylaminomethyl-2-thienyl)-2-syn-methoxyiminoacetic acid in 150 ml of water and 200 ml of dioxan and the mixture is stirred for 1 hour at room temperature, 32.4 g (306 mmole) of sodium carbonate and 66.7 g (306 mmole) of di-tert.-butyl pyrocarbonate are added and the mixture is stirred thoroughly at room temperature for 2½ hours. The solution is concentrated and the residue is dissolved in ethyl acetate/water. The aqueous phase is separated off, adjusted to a pH of 2.4 with concentrated phosphoric acid and extracted with ethyl acetate. After drying the organic phase over sodium sulphate and concentrating the solution in vacuo, the 2-(5-BOC-aminomethyl-2-thienyl)-2-syn-methoxyiminoacetic acid is obtained in the form of an amorphous residue. IR-spectrum (in CHCl$_3$): absorption bands at 2.99, 3.10, 5.88 and 6.71 μ; CS: R$_f$=0.48 (n-butanol/acetic acid/water 67:10:23).

(h) A solution of 5 g (16.0 mmole) of 2-(5-BOC-aminomethyl-2-thienyl)-2-syn-methoxyiminoacetic acid in 50 ml of methylene chloride is cooled to −20°, and 1.87 ml (16.8 mmole) of N-methylmorpholine and 1.90 ml (14 mmole) of chloroformic acid isobutyl ester are added. After a reaction time of 1½ hours at −15°, 6.92 g of 7β-amino-3-acetoxymethyl-3-cephem-4-carboxylic acid diphenylmethyl ester are added and the solution is brought to 0°. After 3 hours, the solution is washed in succession with 2N sulphuric acid, dilute aqueous sodium bicarbonate solution and concentrated aqueous sodium chloride solution. The organic phase is dried over sodium sulphate, filtered and concentrated by evaporation. The residue is chromatographed over silica gel (system: hexane/toluene/acetone 3:4:2) and yields the amorphous, pure 7β-[2-(5-BOC-aminomethyl-2-thienyl)-2-syn-methoxyiminoacetylamino]-3-acetoxymethyl-3-cephem-4-carboxylic acid diphenylmethyl ester. IR-spectrum (in CHCl$_3$): absorption bands at 2.89, 2.94, 5.58, 5.84 and 6.66μ; CS: R$_f$=0.11 (hexane/toluene/acetone 3:4:2); R$_f$=0.1 (toluene/ethyl acetate 3:1).

(i) A solution of 1.7 g (2.2 mmole) of 7β-[2-(5BOC-aminomethyl-2-thienyl)-2-syn-methoxyiminoacetylamino]-3-acetoxymethyl-3-cephem-4-carboxylic acid diphenylmethyl ester and 0.83 g (4.4 mmole) of p-toluenesulphonic acid (monohydrate) in 17 ml of acetonitrile is stirred at room temperature for 2½ hours, then concentrated in vacuo and the residue is taken up in ethyl acetate and water. The organic phase is washed with sodium bicarbonate solution and sodium chloride solution, dried over sodium sulphate and concentrated to dryness. The 7β-[2-(5-aminomethyl-2-thienyl)-2-syn-methoxyiminoacetylamino]-3-acetoxymethyl-3-cephem-4-carboxylic acid diphenylmethyl ester obtained is taken up in approximately 15 ml of methylene chloride (solution I).

At 0°, 0.188 ml (2.64 mmole) of pyridine and 1.43 ml of phosgene in toluene (20% strength) (2.64 mmole) are added to a solution of 0.98 g (2.64 mmole) of (2R)-N-BOC-serine diphenylmethyl ester in 17 ml of methylene chloride and the mixture is stirred for 1¾ hours at 0° under nitrogen (solution II).

Solution I is added to solution II and the mixture is stirred for 1 hour at 0° under nitrogen. After shaking with 2N sulphuric acid, sodium bicarbonate solution and sodium chloride solution, the organic phase is dried over sodium sulphate, filtered and concentrated by evaporation in vacuo. The residue is purified by chromatography over silica gel (system: toluene/ethyl acetate 3:1) and yields 7β-{2-[5-((2R)-2-BOC-amino-2-diphenylmethoxycarbonylethoxycarbonylaminomethyl)-2-thienyl]-2-syn-methoxyiminoacetylamino}-3-acetoxymethyl-3-cephem-4-carboxylic acid diphenylmethyl ester (colourless foam). IR-spectrum (in CHCl$_3$): absorption bands at 2.92, 5.61, 5.74, 5.84, and 6.66 μ; CS: R$_f$=0.41 (toluene/ethyl acetate 1:1).

EXAMPLE 12

(a) At 0°, 3 ml of trifluoroacetic acid are added to a suspension of 0.58 g of 7β-{2-[4-((2R)-2-BOC-amino-2-diphenylmethoxycarbonylethoxycarbonylaminosulphonylamino)phenyl]acetylamino}-3-carbamoyloxymethyl-3-cephem-4-carboxylic acid diphenylmethyl ester and 0.15 ml of anisole in 3 ml of methylene chloride, and the mixture is stirred for 45 minutes at 0°. By adding 17 ml of diethyl ether/hexane 1:1 the trifluoroacetate of the end product is precipitated and is filtered off after 10 minutes at 0° and dissolved in 15 ml of water. The aqueous solution is washed three times with 20 ml of ethyl acetate each time, is adjusted to a pH of 4.6 with 1N sodium hydroxide solution, diluted with acetone and concentrated in vacuo. The precipitating 7β-{2-[4-((2R)-2-amino-2-carboxyethoxycarbonylaminosulphonylamino)phenyl]acetylamino}-3-carbamoyloxymethyl-3-cephem-4-carboxylic acid sodium salt is filtered off and dried in vacuo; [α]$_D^{20}$=+79±1° (c=3; water).

The starting material is produced as follows:

(b) At 20°, a solution of 1.94 g of (2R)-N-BOC-serine diphenylmethyl ester and 0.69 g of pyridine in 10 ml of methylene chloride is added dropwise to a solution of 0.69 g of chlorosulphonyl isocyanate in 1.3 ml of methylene chloride. After stirring for 20 minutes at 40° the clear solution is cooled to 0° (solution A).

1.29 g of trimethylchlorosilane is added to a suspension of 0.75 g of aminophenylacetic acid in 2.91 g of pyridine, a clear solution resulting and the temperature increasing to 38°. After stirring for 20 minutes at 40°–45°, the solution is cooled to 0° (solution B).

At 0° solution B is added dropwise to solution A and the mixture is then stirred for 30 minutes at 0° and for 1 hour at +22°. The mixture is poured, while stirring, onto 80 ml of 0.2M dipotassium hydrogen phosphate solution, freed of methylene chloride in vacuo and the remaining aqueous phase is extracted in the cold at a pH of 2 with ethyl acetate. By concentrating the organic phase by evaporation, the 2-[4-((2R)-2-BOC-amino-2-diphenylmethoxycarbonylethoxycarbonylaminosulphonylamino)phenyl]-acetic acid is obtained in the form of a foam.

(c) At 0°, 0.43 g of chloroformic acid isobutyl ester is added to a solution of 2.08 g of 2-[4-((2R)-2-BOC-amino-2-diphenylmethoxycarbonylethoxycarbonylaminosulphonylamino)phenyl]acetic acid and 0.32 g of N-methylmorpholine in 28 ml of methylene chloride, and the mixture is then stirred for 1 hour at 0°. This solution of the resulting mixed anhydride is added dropwise at 0° to a solution of 1.62 g of 7β-amino-3-carbamoyloxymethyl-3-cephem-4-carboxylic acid diphenylmethyl ester p-tosylate and 0.34 g of N-methylmorpholine in 14 ml of methylene chloride. After stirring for 1½ hours at 0° and for 1 at +22° the mixture is stirred into 100 ml of 0.3M potassium dihydrogen phosphate solution and freed of organic solvents in vacuo. The remaining aqueous phase is extracted at 0° and a pH of 2.0 with ethyl acetate. The organic phase is washed with 0.5M dipotassium hydrogen phosphate solution, dried with sodium sulphate, concentrated by evaporation in vacuo and yields 7β-{2-[4-((2R)-2-BOC-amino-2-diphenylmethoxycarbonylethoxycarbonylaminosulphonylamino)phenyl]acetylamino}-3-carbamoyloxymethyl-3-cephem-4-carboxylic acid diphenylmethyl ester.

EXAMPLE 13

(a) A mixture of 1.00 g (1.29 mmole) of 7β-[2-(5-BOC-aminomethyl-2-furyl)-2-syn-methoxyiminoacetylamino]-3-[(1-methyl-1H-tetrazol-5-yl)thiomethyl]-3-cephem-4-carboxylic acid diphenylmethyl ester in 2 ml of anisole is cooled to 0°, 8 ml of trifluoroacetic acid are added, and the mixture is stirred for 15 minutes at 0°. Then the process of adding toluene and concentrating by evaporation in vacuo is carried out twice. The residue, containing the trifluoroacetate of the end product, is taken up in ethyl acetate/water and the organic phase is separated off and extracted by shaking twice with water. The combined aqueous phases are washed three times with ethyl acetate, adjusted to a pH of 5.7 with triethylamine (20% solution in ethanol), concentrated slightly in vacuo, and acetone is added, whereupon 7β-[2-(5-aminomethyl-2-furyl)-2-syn-methoxyiminoacetylamino]-3-[(1-methyl-1H-tetrazol-5-yl)-thiomethyl]-3-cephem-4-carboxylic acid is precipitated. CS: $R_{f52A}=0.096$; IR-spectrum (Nujol): absorption bands at 2.85 (shoulder), 3.11, 5.66, 6.00, 6.25 and 6.45 μ.

EXAMPLE 14

(a) A mixture of 3 g (4.25 mmole) of 7β-[2-(5-BOC-aminomethyl-2-furyl)-2-syn-methoxyiminoacetylamino]-3-carbamoyloxymethyl-3-cephem-4-carboxylic acid diphenylmethyl ester in 7.5 ml of anisole is cooled to 0°, 30 ml of trifluoroacetic acid are added and the mixture is stirred for 20 minutes at 0°. Subsequently, the process of adding toluene and concentrating by evaporation in vacuo is carried out three times. The residue, containing the trifluoroacetate of the end product, is taken up in ethyl acetate/water, the organic phase is separated off and extracted by shaking twice with water. The combined aqueous phases are washed three times with ethyl acetate, filtered, adjusted to a pH of 5.7 with triethylamine (20% solution in ethanol), concentrated to approximately 5 ml in vacuo and acetone is added, whereupon 7β-[2-(5-aminoethyl-2-furyl)-2-synmethoxyiminoacetylamino]-3-carbamoyloxymethyl-3-cephem-4-carboxylic acid is precipitated. CS: $R_{f52A}=0.062$; IR-spectrum (Nujol): absorption bands at 2.87 (shoulder), 3.09, 5.65, 5.87, 5.98, 6.23 and 6.47μ.

EXAMPLE 15

(a) A solution of 10.5 g of 7β-{(2R,S)-2-[4-((2R)-2-BOC-amino-2-tert.-butoxycarbonylethoxycarbonylamino)phenyl]-2-(2,2,2-trichloroethoxycarbonyloxy)acetylamino}-3-carbamoyloxymethyl-3-cephem-4-carboxylic acid diphenylmethyl ester in 100 ml of acetonitrile and 100 ml of glacial acetic acid is cooled in an ice bath and while stirring vigorously at +3° a total of 20.5 g of zinc powder is added in portions at equal intervals over a period of 2 hours. The suspension is subsequently stirred for a further 3 hours in an ice-bath, then suction-filtered off through Celite and the filtered material is washed with a large amount of ethyl acetate. The filtrate is washed in succession with a large amount of water, 1N sodium bicarbonate and water. The ethyl acetate solution is dried over sodium sulphate, the solvent is evaporated off in a rotary evaporator at 45° and the residue is purified by chromatography over 25 times the amount of silica gel. The fractions with methylene chloride/methyl acetate (7:3) as eluant are combined and 7β-{(2R,S)-2-[4-((2R)-2-BOC-amino-2-tert.-butoxycarbonylethoxycarbonylamino)phenyl]-2-hydroxyacetylamino}-3-carbamoyloxymethyl-3-cephem-4-carboxylic acid diphenylmethyl ester is precipitated from ethyl acetate solution with a mixture of petroleum ether and diethyl ether. CS (solvent: chloroform/ethyl acetate/ethanol (5:5:0.1)): $R_f=0.20$ and 0.32 (diastereomeric mixture).

A mixture of 2.70 g of 7β-{(2R,S)-2-[4-((2R)-2-BOC-amino-2-tert.-butoxycarbonylethoxycarbonylamino)phenyl]-2-hydroxyacetylamino}-3-carbamoyloxymethyl-3-cephem-4-carboxylic acid diphenylmethyl ester, 2.70 ml of methylene chloride, 1.70 ml of anisole and 27.0 ml of trifluoroacetic acid is stirred for 1 hour at room temperature with the exclusion of atmospheric moisture. The suspension is then poured onto an ice-cold mixture of petroleum ether (500 ml) and diethyl ether (250 ml), the resulting trifluoroacetate is suction-filtered off, washed with diethyl ether and dried at room temperature under high vacuum. The trifluoroacetate of 7β-{(2R,S)-2-[4-((2R)-2-amino-2-carboxyethoxycarbonylamino)phenyl]-2-hydroxyacetylamino}-3-carbamoyloxymethyl-3-cephem-4-carboxylic acid obtained is converted in a manner analogous to that described in Example 1a) into the corresponding sodium salt. Mp. from 220° (with decomposition). CS:$R_{f101}=0.24$, $R_{f101A}=0.17$.

The starting material can be produced as follows:

(b) 16 g of (R,S)-4-aminomandelic acid are suspended in 80 ml of water, adjusted to a pH of 7.5 by adding dropwise while stirring 2N sodium hydroxide solution, and the solution is cooled by means of an ice bath to +3° to +5°. A solution of 22.2 g of chloroformic acid 2,2,2-trichloroethyl ester in 50 ml of tetrahydrofuran is then added dropwise at +5° over a period of 20 minutes while stirring vigorously and cooling, and by the dropwise addition of 2N sodium hydroxide solution the pH of the reaction mixture is held between 7 and 8. The mixture is subsequently stirred for 1 hour at +5°, then diluted with 100 ml of water and extracted twice with ethyl acetate. The aqueous phase is separated off, given a coating layer of ethyl acetate, cooled in an ice bath, adjusted to an acid pH of 2 by adding dilute hydrochloric acid (1:1) while stirring, and extracted twice with ethyl acetate. The organic extracts are combined, washed once with salt water solution, dried over sodium sulphate and the solvent evaporated off in a rotary evaporator at 50°. (R,S)-4-(2,2,2-trichloroethoxycarbonylamino)mandelic acid is recrystallized from ethyl acetate/petroleum ether. Mp. 202°–205° (with decomposition).

(c) 27 ml of benzyl bromide are added dropwise to a solution of 64 g of (R,S)-4-(2,2,2-trichloroethoxycarbonylamino)mandelic acid in 140 ml of N,N-dimethylformamide and 38.4 ml of triethylamine at room temperature over a period of 2 hours, while stirring. The reaction mixture is stirred for 18 hours at room temperature, the suspension is poured onto a large amount of water and extracted twice with a mixture of ethyl acetate/diethyl ether (1:1). The organic extracts are combined, washed twice with salt water solution and dried over sodium sulphate. After evaporating off the solvent, the product is digested with petroleum ether and (R,S)-4-(2,2,2-trichloroethoxycarbonylamino)mandelic acid benzyl ester is obtained in crystalline form. Mp. 72°–76° (with decomposition).

(d) A total of 21 g of zinc powder is added in portions at equal intervals over a period of 3 hours at room temperature while stirring to a solution of 20 g of (R,S)-4-(2,2,2-trichloroethoxycarbonylamino)mandelic acid benzyl ester in 200 ml of glacial acetic acid. Subsequently the suspension is stirred for a further 2 hours at room temperature, then suction-filtered through Celite, the filtered material is washed with ethyl acetate and the filtrate is strongly concentrated in a rotary evaporator at 50°. The residue is poured onto water, given a coating layer of ethyl acetate, adjusted to a slightly alkaline pH of 7.5–8.0 by the addition of solid sodium bicarbonate and extracted twice with ethyl acetate. The organic extracts are combined, washed in succession with salt water solution, 1N sodium bicarbonate and salt water solution, dried over sodium sulphate and the solvent is evaporated off in a rotary evaporator at 45°. The (R,S)-4-aminomandelic acid benzyl ester has a melting point of 88°–92° (with decomposition).

(e) A solution of 2.50 ml of pyridine in 10 ml of methylene chloride is added dropwise over a period of 4 minutes while stirring and cooling at 0° to +5° to a mixture of 16 ml of phosgene solution (20% in toluene) and 10 ml of methylene chloride. A solution of 8.0 g of N-BOC-(R)-serine tert.-butyl ester in 40 ml of methylene chloride is then added dropwise over a period of 15 minutes to the above suspension and the reaction mixture is subsequently stirred for one hour at 0° to +5°. After adding a solution of 7.8 g of (R,S)-4-aminomandelic acid benzyl ester in 80 ml of methylene chloride and 2.7 ml of pyridine over a period of 3 minutes at 0°, the suspension is stirred for 30 minutes at 0° and for 30 minutes at room temperature, then diluted with 400 ml of diethyl ether and washed in succession with water, citric acid solution (5%), water, 0.1N hydrochloric acid and water. After drying and evaporating off the solvent the oily (R,S)-4-((2R)-2-BOC-amino-2-tert.-butoxycarbonylethoxycarbonylamino)mandelic acid benzyl ester is brought to crystallization by triturating with petroleum ether. Mp. 98°–100°; $[\alpha]_D = -17\pm1°$ (c=2.83 in chloroform); CS (solvent: toluene/chloroform/ethyl acetate (1:1:1)): $R_f=0.46$.

(f) A solution of 20.0 g of (R,S)-4-((2R)-2-BOC-amino-2-tert.-butoxycarbonylethoxycarbonylamino)-mandelic acid benzyl ester in 40 ml of tetrahydrofuran and 40 ml of pyridine is cooled in an ice bath and a solution of 6.90 ml of chloroformic acid 2,2,2-trichloroethyl ester in 40 ml of tetrahydrofuran is added dropwise while stirring over a period of 20 minutes at 0° to +5°. The reaction mixture is stirred at 0° for 3 hours, diluted with diethyl ether and the organic phase is washed in succession with water, citric acid solution (15%), water, 1N sodium bicarbonate and water. The solution is dried over sodium sulphate and the solvent is evaporated off in a rotary evaporator at 45°. By mixing with petroleum ether the (αR,S)-4-((2R)-2-BOC-amino-2-tert.-butoxycarbonylethoxycarbonylamino)-α-(2,2,2-trichloroethoxycarbonyloxy)phenylacetic acid benzyl ester solidifies. Mp. 85°–90° (with decomposition). $[\alpha]_D = -15\pm1°$ (c=3.02 in chloroform): CS (solvent: toluene/chloroform/ethyl acetate (4.5:4.5:1)): $R_f=0.42$.

(g) A solution of 18.0 g of (αR,S)-4-((2R)-2-BOC-amino-2-tert.-butoxycarbonylethoxycarbonylamino)-α-(2,2,2-trichloroethoxycarbonyloxy)phenylacetic acid benzyl ester in 250 ml of ethyl acetate is hydrogenated in the presence of 3.0 g of palladium on activated carbon (10%). After approximately 2 hours the calculated amount of hydrogen has been absorbed. The catalyst is filtered off, washed with ethyl acetate, the filtrate is concentrated in a rotary evaporator at 45° and (αR,S)-4-((2R)-2-BOC-amino-2-tert.-butoxycarbonylethoxycarbonylamino)-α-(2,2,2-trichloroethoxycarbonyloxy)-phenylacetic acid is precipitated by adding petroleum ether. Mp. 94°–100° (with decomposition): $[\alpha]_D = -18\pm1°$ (c=0.93 in chloroform).

(h) A solution of 7.25 g of 7β-amino-3-carbamoyloxymethyl-3-cephem-4-carboxylic acid diphenylmethyl ester and 10.0 g of (αR,S)-4-((2R)-2-BOC-amino-2-tert.-butoxycarbonylethoxycarbonyl-amino)-α-(2,2,2-trichloroethoxycarbonyloxy)phenylacetic acid in 125 ml of tetrahydrofuran is reacted with a solution of 3.75 g of N,N'-dicyclohexyl carbodiimide in 25 ml of tetrahydrofuran and later with a second portion of 1.75 g of solid N,N'-dicyclohexyl carbodiimide in accordance with the process of Example 1. The crude product is purified by chromatography over 25 times the amount of silica gel. The fractions with methylene chloride/methyl acetate (17:3) as eluant are combined and 7β-{(2R,S)-2-[4-((2R)-2-BOC-amino-2-tert.-butoxycarbonylethoxycarbonylamino)phenyl]-2-(2,2,2-trichloroethoxycarbonyloxy)acetylamino}-3-carbamoyloxymethyl-3-cephem-4-carboxylic acid diphenylmethyl ester is precipitated from ethyl acetate solution with a mixture of petroleum ether and diethyl ether. Mp. 138°–145° (with decomposition). CS (solvent: toluene/ethyl acetate/ethanol (5:5:0.1)=$R_f=0.54$.

EXAMPLE 16

(a) A solution of 8.50 g of 7β-{(2R,S)-2-[4-((2R)-2-BOC-amino-2-tert.-butoxycarbonylethoxycarbonylamino)-phenyl]-2-(2,2,2-trichloroethoxycarbonyloxy)acetylamino}-3-[(1-methyl-1H-tetrazol-5-yl)thiomethyl]-3-cephem-4-carboxylic acid diphenylmethyl ester in 85 ml of acetonitrile and 85 ml of glacial acetic acid is cooled in an ice bath and a total of 22 g of zinc powder is added in portions at equal intervals over a period of 90 minutes at +2° while stirring vigorously. Subsequently the suspension is stirred in the ice bath for a further 2 hours and worked up as in Example 15a). The crude product is purified by chromatography over 30 times the amount of silica gel. The fractions with methylene chloride/methyl acetate (17:3) as eluant are combined and 7β-{(2R,S)-2-[4-((2R)-2-BOC-amino-2-tert.-butoxycarbonylethoxycarbonylamino)phenyl]-2-hydroxyacetylamino}-3-[(1-methyl-1H-tetrazol-5-yl)thiomethyl]-3-cephem-4-carboxylic acid diphenylmethyl ester is precipitated from ethyl acetate solution with a mixture of petroleum ether and diethyl ether. Mp. 150°–155° (with decomposition). CS (solvent: toluene/chloroform/ethyl acetate (1:1:1)): $R_f=0.09$ and 0.15 (diastereomeric mixture).

A mixture of 2.40 g of 7β-{(2R,S)-2-[4-((2R)-2-BOC-amino-2-tert.-butoxycarbonylethoxycarbonylamino)-phenyl]-2-hydroxyacetylamino}-3-[(1-methyl-1H-tetrazol-5-yl)thiomethyl]-3-cephem-4-carboxylic acid diphenylmethyl ester, 1.60 ml of methylene chloride, 1.00 ml of anisole and 48 ml of trifluoroacetic acid is stirred for 75 minutes at room temperature with the exclusion of atmospheric moisture. The suspension is subsequently poured onto an ice-cold mixture of petroleum ether (500 ml) and diethyl ether (250 ml), the resulting trifluoroacetate of 7β-{(2R,S)-2-[4-((2R)-amino-2-carboxyethoxycarbonylamino)phenyl]-2-hydroxyacetylamino}-3-[(1-methyl-1H-tetrazol-5-yl)thiomethyl]-3-cephem-4-carboxylic acid is suction-filtered off, washed with diethyl ether and dried at room temperature under a high vacuum.

The corresponding sodium salt is obtained from the trifluoroacetate in accordance with the process of Example 1(a). Mp. from 170° (with decomposition) CS: $R_{f101}=0.27$, $R_{f101A}=0.21$, $R_{fS2A}=0.06$.

The starting material can be produced as follows:

(b) A solution of 7.85 g of 7β-amino-3-[(1-methyl-1H-tetrazol-5-yl)thiomethyl]-3-cephem-4-carboxylic acid diphenylmethyl ester and 10.0 g of (αR,S)-4-((2R)-2-BOC-amino-2-tert.-butoxycarbonylethoxycarbonyloxy)phenylacetic acid in 40 ml of tetrahydrofuran and 20 ml of N,N-dimethylformamide is reacted with a solution of 3.25 g of N,N'-dicyclohexyl carbodiimide in 15 ml of tetrahydrofuran and with 1.60 g of solid N,N'-dicyclohexyl carbodiimide in accordance with the process of Example 1. The crude product is purified by filtering through 15 times the amount of silica gel. The fractions with methylene chloride/methyl acetate (93:7) as eluant are combined and 7β-{(2R,S)-2-[4-((2R)-2-BOC-amino-2-tert.-butoxycarbonylethoxycarbonylamino)-phenyl]-2-(2,2,2-trichloroethoxycarbonyloxy)acetylamino}-3-[(1-methyl-1H-tetrazol-5-yl)thiomethyl]-3-cephem-4-carboxylic acid diphenylmethyl ester is precipitated from ethyl acetate solution with a mixture of petroleum ether and diethyl ether. CS (solvent: toluene/chloroform/ethyl acetate (1:1:1)): $R_f=0.19$.

EXAMPLE 17

(a) A mixture of 2.0 g of 7β-{(2R)-2-[4-((2R)-2-BOC-amino-2-diphenylmethoxycarbonylethoxycarbonylamino)phenyl]-2-hydroxyacetylamino}-3-[(1-methyl-1H-tetrazol-5-yl)thiomethyl]-3-cephem-4-carboxylic acid diphenylmethyl ester, 2.0 ml of methylene chloride, 1.2 ml of anisole and 16 ml of ice-cold trifluoroacetic acid is stirred for 15 minutes at room temperature with the exclusion of atmospheric moisture. A voluminous precipitate is precipitated from the initially clear solution. Subsequently the suspension is poured onto an ice-cold mixture of petroleum ether (400 ml) and diethyl ether (200 ml), the resulting trifluoroacetate of 7β-{(2R)-2-[4-((2R)-2-amino-2-carboxyethoxycarbonylamino)phenyl]-2-hydroxyacetylamino}-3-[(1-methyl-1H-tetrazol-5-yl)thiomethyl]-3-cephem-4-carboxylic acid is suction-filtered off, washed with diethyl ether and dried at room temperature under a high vacuum. The corresponding sodium salt is obtained from the trifluoroacetate in accordance with the process of Example 1(a). Mp. from 165° (with decomposition); $[α]_D=-3±1°$ (c=1.83 in 0.1N sodium bicarbonate); CS: $R_{f101}=0.30$, $R_{f101A}=0.23$, $R_{fS2A}=0.07$.

The starting material can be produced as follows:

(b) A solution of 5.70 g of pyridine in 10 ml of methylene chloride is added dropwise while stirring and cooling at 0° to +3° to 105 ml of phosgene solution (20% strength in toluene) and the reaction mixture is stirred for 10 minutes at 0°. After adding dropwise a solution of 25.0 g of (R)-N-BOC-serine diphenylmethyl ester over a period of 20 minutes at 0°, the mixture is stirred for 1 hour in an ice bath and then diluted with methylene chloride. The methylene chloride solution is washed three times with ice-cold water, dried over sodium sulphate and the solvent is evaporated off in a rotary evaporator at 45°. On triturating with petroleum ether the (2R)-2-BOC amino-2-diphenylmethoxycarbonylethoxycarbonyl chloride solidifies. Mp. 79°-80° (with decomposition).

(c) 8.86 g of (R)-4-aminomandelic acid are made into a paste with a mixture of 90 ml of acetonitrile and 20 ml of tetrahydrofuran, cooled to 0° and a total of 25 ml of N,O-bis(trimethylsilyl)acetamide are added in portions at 0° over a period of 75 minutes while stirring, resulting in a clear solution. This solution is cooled to −15° and while stirring with 4.2 ml of pyridine, subsequently a solution of 23 g of (2R)-2-BOC-amino-2-diphenylmethoxycarbonylethoxycarbonyl chloride in a mixture of 90 ml of acetonitrile and 90 ml of tetrahydrofuran are added. After stirring in an ice bath for 2.5 hours the mixture is diluted with ethyl acetate, washed three times with water, dried over sodium sulphate and the solvent is distilled off in a rotary evaporator at 45°. On adding petroleum ether (R)-4-((2R)-2-BOC-amino-2-diphenylmethoxycarbonylethoxycarbonylamino)mandelic acid solidifies. Mp. 65°-71°; $[α]_D=-36°±1°$ (c=2.93 in dimethyl sulphoxide); CS (solvent: chloroform/ethyl acetate/glacial acetic acid (5:5:0.2)): $R_f=0.23$.

(d) A solution of 7.55 g of 7β-amino-3-[(1-methyl-1H-tetrazol-5-yl)thiomethyl]-3-cephem-4-carboxylic acid diphenylmethyl ester, 8.50 g of (R)-4-((2R)-2-BOC-amino-2-diphenylmethoxycarbonylethoxycarbonylamino)mandelic acid and 2.85 g of 1-hydroxybenzotriazole (moistened with 10% water) in a mixture of 30 ml of N,N-dimethylformamide and 45 ml of tetrahydrofuran is cooled with an ice bath to 0° to +3°, a solution of 1.70 g of N,N'-dicyclohexyl carbodiimide in 20 ml of tetrahydrofuran is added dropwise over a period of 30 minutes while cooling and stirring, and the reaction mixture is further stirred in the ice bath. After 35 hours, a further solution of 1.50 g of N,N'-dicyclohexyl carbodiimide in 20 ml of tetrahydrofuran is added dropwise. After a total of 7.5 hours at 0° the suspension is suction-filtered off, the filtered material is washed with ethyl acetate, the filtrate is diluted with a large amount of ethyl acetate and the ethyl acetate solution is washed in succession with water, 1N sodium bicarbonate and water. The crude product is purified by chromatography over 25 times the amount of silica gel. The fractions with chloroform/methyl acetate (14:1) as eluant are combined and 7β-{(2R)-2-[4-((2R)-2-BOC-amino-2-diphenylmethoxycarbonylethoxycarbonylamino)phenyl]-2-hydroxyacetylamino}-3-[(1-methyl-1H-tetrazol-5-yl)thiomethyl]-3-cephem-4-carboxylic acid diphenylmethyl ester is crystallised from ethyl acetate. Mp. 169°-172° (with decomposition). CS (solvent: chloroform/ethyl acetate/ethanol (5:5:0.2)): $R_f=0.57$. $[α]_D=-52±1°$ (c=1.75 in dimethyl sulphoxide).

EXAMPLE 18

(a) A mixture of 2.0 g of 7β-{(2R)-2-[4-((2R)-2-BOC-amino-2-diphenylmethoxycarbonylethoxycarbonylamino)phenyl]-2-hydroxyacetylamino}-3-carbamoyloxymethyl-3-cephem-4-carboxylic acid diphenylmethyl ester, 2.0 ml of methylene chloride, 1.20 ml of anisole and 16.0 ml of ice-cold trifluoroacetic acid is stirred for 15 minutes at room temperature with the exclusion of atmospheric moisture. The suspension is then poured onto an ice-cold mixture of petroleum ether (400 ml) and diethyl ether (200 ml), the resulting trifluoroacetate of 7β-{(2R)-2-[4-((2R)-2-amino-2-carboxyethoxycarbonylamino)phenyl]-2-hydroxyacetylamino}-3-carbamoyloxymethyl-3-cephem-4-carboxylic acid is suction-filtered off, washed with diethyl ether and dried under high vacuum at room temperature. The corresponding sodium salt is obtained from the trifluoroacetate in accordance with the process of Example 1(a). Mp. from 230° (with decomposition): $[\alpha]_D = +62\pm1°$ (c=1.93 in 0.1N sodium bicarbonate); CS: $R_{f524}=0.06$, $R_{f101}=0.32$, $R_{f101A}=0.24$.

The starting material can be produced as follows:

(b) A solution of 8.0 g of 7β-amino-3-carbamoyloxymethyl-3-cephem-4-carboxylic acid diphenylmethyl ester, 10.0 g of (R)-4-((2R)-2-BOC-amino-2-diphenylmethoxycarbonylethoxycarbonylamino)mandelic acid and 3.40 g of 1-hydroxybenzotriazole in 80 ml of tetrahydrofuran is cooled to +3°, then, while stirring and cooling, a solution of 4.0 g of N,N'-dicyclohexyl carbodiimide in 20 ml of tetrahydrofuran is added dropwise over a period of 30 minutes and the reaction mixture is stirred for 7 hours in an ice bath. Subsequently the suspension is worked up in accordance with the process of Example 17d. The crude product is purified by chromatography over 30 times the amount of silica gel. The fractions with chloroform/methyl acetate (4:1) as eluant are combined and the product is crystallised from chloroform. 7β-{(2R)-2-[4-((2R)-2-BOC-amino-2-diphenylmethoxycarbonylethoxycarbonylamino)-phenyl]-2-hydroxyacetylamino}-3-carbamoyloxymethyl-3-cephem-4-carboxylic acid diphenylmethyl ester melts at 129°–133° (with decomposition); $[\alpha]_D=+22\pm1°$ (c=3.41 in dimethyl sulphoxide); CS (solvent: chloroform/ethyl acetate/ethanol (5:5:0.1)): $R_f=0.32$.

EXAMPLE 19

(a) A mixture of 2.10 g of 7α-methoxy-7β-{2-[4-((2R)-2-BOC-amino-2-diphenylmethoxycarbonylethoxycarbonylamino)phenyl]-acetylamino}-3-[(1-methyl-1H-tetrazol-5-yl)thiomethyl]-3-cephem-4-carboxylic acid diphenylmethyl ester, 2.0 ml of methylene chloride, 1.1 ml of anisole and 15 ml of ice-cold trifluoroacetic acid is stirred for 15 minutes at room temperature with the exclusion of atmospheric moisture. The suspension is then poured onto an ice-cold mixture of petroleum ether (400 ml) and diethyl ether (200 ml), the resulting trifluoroacetate is suction-filtered off, washed with diethyl ether and dried at room temperature under a high vacuum. 7α-methoxy-7β-{2-[4-((2R)-2-amino-2-carboxyethoxycarbonylamino)phenyl]acetylamino}-3-[(1-methyl-1H-tetrazol-5-yl)thiomethyl]-3-cephem-4-carboxylic acid sodium salt is obtained from the trifluoroacetate in accordance with the process of Example 1. Mp. from 170° (with decomposition); CS: $R_{f524}=0.05$; $R_{f101}=0.33$, $R_{f101A}=0.47$.

The starting material can be produced as follows:

(b) 7β-{2-[4-((2R)-2-BOC-amino-2-diphenylmethoxycarbonylethoxycarbonylamino)phenyl]acetylamino}-3-[(1-methyl-1H-tetrazol-5-yl)thiomethyl]-3-cephem-4-carboxylic acid diphenylmethyl ester is obtained by reacting 7β-amino-3-[(1-methyl-1H-tetrazol-5-yl)thiomethyl]-3-cephem-4-carboxylic acid diphenylmethyl ester with 4-((2R)-2-BOC-amino-2-diphenylmethoxycarbonylethoxycarbonylamino)phenylacetic acid in accordance with the process of Example 5f). Mp. 128°–135° (with decomposition) (crystallised from chloroform). CS (solvent: toluene/ethyl acetate (3:2)): $R_f=0.34$.

(c) The following reaction is carried out in a nitrogen atmosphere. A solution of 5.0 g of 7β-{2-[4-((2R)-2-BOC-amino-2-diphenylmethoxycarbonylethoxycarbonylamino)phenyl]acetylamino}-3-[(1-methyl-1H-tetrazol-5-yl)thiomethyl]-3-cephem-4-carboxylic acid diphenylmethyl ester in 400 ml of absolute tetrahydrofuran is cooled to −75° (dry ice/acetone bath) and a precooled solution of lithium methoxide in methanol (130 mg of lithium dissolved in 16 ml of methanol) is added dropwise over a period of 2 minutes, the temperature rising to −70° and an orange-coloured solution being formed. The reaction mixture is stirred for a further 2 minutes at −75°, then 0.90 ml of tert.-butyl hypochlorite is added and stirring at −75° is continued. After 5 minutes a further 0.20 ml of tert.-butyl hypochlorite is added to the brown-coloured solution. After 20 minutes 3 ml of glacial acetic acid are added dropwise to the reaction mixture. The cooling bath is removed and the solution is heated to room temperature. The mixture is diluted with ethyl acetate, the tetrahydrofuran is evaporated off in a rotary evaporator at 45°, the ethyl acetate solution is washed in succession with water, 1N sodium bicarbonate and water, dried over sodium sulphate and the solvent is evaporated off. The crude product is chromatographed over 30 times the amount of silica gel. The fractions with methylene chloride/methyl acetate (20:1) as eluant are combined. The Δ2/Δ3 isomeric mixture of 7α-methoxycephalosporin derivative is obtained. CS (solvent: toluene/ethyl acetate (3:2)):$R_f=0.36$.

1.30 g of Δ2/Δ3 isomeric mixture of 7α-methoxycephalosporin derivative are dissolved in 6 ml of chloroform, cooled in an ince bath, while stirring and cooling a solution of 0.24 g of 3-chloroperbenzoic acid (85%) is added dropwise and the reaction mixture is stirred for 1.5 hours at 0°. The solution is diluted with ethyl acetate, washed in succession with water, 1N sodium bicarbonate, water, sodium bisulphite solution (5%) and water, dried over sodium sulphate and the solvent is evaporated off in a rotary evaporator at 45°. The crude product is purified by filtering through 10 times the amount of silica gel. The 7α-methoxy-7β-{2-[4-((2R)-2-BOC-amino-2-diphenylmethoxycarbonylethoxycarbonylamino)phenyl]acetylamino}-3-[(1-methyl-1H-tetrazol-5-yl)thiomethyl]-3-cephem-4-carboxylic acid diphenylmethyl ester 1β-oxide is eluted with a mixture of methylene chloride/methyl acetate (7:3). CS (solvent: ethyl acetate): $R_f=0.38$.

(d) A solution of 2.40 g of 7α-methoxy-7β-{2-[4-((2R)-2-BOC-amino-3-diphenylmethoxycarbonylamino)phenyl]acetylamino}-3-[(1-methyl-1H- tetrazol-5-yl)thiomethyl]-3-cephem-4-carboxylic acid diphenylmethyl ester 1β-oxide in a mixture of 150 ml of methylene chloride and 10 ml of N,N-dimethylacetamide is cooled to 0°, while stirring and cooling 0.50 ml of phosphorus trichloride is added and the mixture is stirred for 15 minutes in an ice bath. The reaction mixture is diluted with methylene chloride, washed in succession with water. 1N sodium bicarbonate and water, dried over sodium sulphate and the solvent is evaporated off in a rotary evaporator at 45°. The product is purified by chromatography over 20 times the amount of silica gel. The fractions with methylene chloride/methyl acetate (20:1) as eluant are combined. 7α-methoxy-7β-{2-[4-((2R)-2-BOC-amino-2-diphenylmethoxycarbonylethoxycarbonylamino)phenyl]acetylamino}-3-[(1-methyl-1H-tetrazol-5-yl)thiomethyl]-3-cephem-4-carboxylic acid diphenylmethyl ester is precipitated from ethyl acetate solution with a mixture of petroleum ether and ether. CS (solvent: toluene/ethyl acetate (3:2)): $R_f=0.36$.

EXAMPLE 20

(a) A suspension of 3.0 g of 7β-{(2R,S)-2-[4-((2R)-2-amino-2-diphenylmethoxycarbonylethoxycarbonylamino)phenyl]-2-sulphoacetylamino}-3-[(1-methyl-1H-tetrazol-5-yl)thiomethyl]-3-cephem-4-carboxylic acid diphenylmethyl ester in 25 ml of methylene chloride and 1.0 ml of anisole is cooled to 0°, 4.65 ml of ice-cold trifluoroacetic acid are added and the mixture is stirred for 40 minutes in an ice bath with the exclusion of atmospheric moisture. A greasy precipitate is precipitated from the initially clear solution. At the end of the reaction time the grease is quickly made into a solution by the addition of 10 ml of ice-cold trifluoroacetic acid, then poured onto an ice-cold mixture of petroleum ether (500 ml) and diethyl ether (250 ml). The resulting trifluoroacetate is suction-filtered off, washed with diethyl ether and dried at room temperature under a high vacuum. 7β-{(2R,S)-2-[4-((2R)-2-amino-2-carboxyethoxycarbonylamino)phenyl]-2-sulphoacetylamino}-3-[(1-methyl-1H-tetrazol-5-yl)thiomethyl]-3-cephem-4-carboxylic acid disodium salt is obtained from the trifluoroacetate in accordance with the process of Example 1a). Mp. from 205° (with decomposition). CS: $R_{f101}=0.23$, $R_{f101A}=0.14$.

The starting material can be produced as follows:

(b) A solution of 88 g of (αR,S)-4-nitro-α-sulphophenylacetic acid in 430 ml of water is hydrogenated in the presence of 12.5 g of palladium on activated carbon (10%). After approximately 12 hours the hydrogen absorption comes to a standstill. The catalyst is filtered off, washed with a little water, the filtrate is cooled in an ice bath, while stirring and cooling adjusted to an acid pH of 1.2 by adding dropwise concentrated hydrochloric acid, and the suspension is allowed to stand for a few hours in an ice bath. The resulting (αR,S)-4-amino-α-sulphophenylacetic acid is suction-filtered off and washed with ice-cold water. Mp. above 300° (with decomposition). CS: $R_{f52A}=0.03$.

(c) 17.5 g of (αR,S)-4-amino-α-sulphophenylacetic acid are made into a paste with a mixture of 120 ml of methylene chloride and 40 ml of acetonitrile and, while stirring, a total of 60 ml of N,O-bis-(trimethylsilyl)acetamide are added in portions over a period of 75 minutes. The clear solution obtained is stirred for a further hour at room temperature, cooled to 0°, and in succession 6.10 ml of pyridine and a solution of 34 g of (2R)-2-BOC-amino-2-diphenylmethoxycarbonylethoxycarbonyl chloride in 200 ml of methylene chloride are added. After stirring for one hour in an ice-bath and for 1.5 hours at room temperature, the reaction mixture is poured into 4 liters of ethyl acetate, washed in succession with 0.1N hydrochloric acid, water and salt water solution, dried over sodium sulphate and the solvent is evaporated off in a rotary evaporator at 45°. On mixing with petroleum ether the (αR,S)-4-((2R)-2-BOC-amino-2-diphenylmethoxycarbonylethoxycarbonylamino)-α-sulphophenylacetic acid solidifes. Mp. from 160° (with decomposition). CS: $R_{f52A}=0.42$, $R_{f67}=0.31$.

A suspension of 26.5 g of (αR,S)-4-((2R)-2-BOC-amino-2-diphenylmethoxycarbonylethoxycarbonylamino)-α-sulphophenylacetic acid and 40 g of toluene-4-sulphonic acid monohydrate in 430 ml of acetonitrile is stirred for 5 hours at room temperature, then 250 ml of water are added and the acetonitrile is evaporated off in a rotary evaporator at 50°. The resulting product is suction-filtered off and washed with water. The (αR,S)-4-((2R)-2-amino-2-diphenylmethoxycarbonylethoxycarbonylamino)-α-sulphophenylacetic acid is purified by dissolving in water at a pH of 6.8 (addition of 2N sodium hydroxide solution), filtering and acidifying the clear solution with 2N hydrochloric acid (pH 1.5). Mp. from 190° (with decomposition); $[α]_D=+11\pm1°$ (c=2.55 in dimethyl sulphoxide); CS: $R_{f52A}=0.23$.

(d) The following reaction is carried out in a nitrogen atmosphere. 2.6 g of N,N'-dicyclohexyl carbodiimide are added to a solution of 5.1 g of 7β-amino-3-[(1-methyl-1H-tetrazol-5-yl)thiomethyl]-3-cephem-4-carboxylic acid diphenylmethyl ester and 5.0 g of (αR,S)-4-((2R)-2-amino-2-diphenylmethoxycarbonylethoxycarbonylamino)-α-sulphophenylacetic acid in a mixture of 270 ml of tetrahydrofuran and 30 ml of water, and the reaction mixture is stirred for 8 hours at room temperature. The suspension is then suction-filtered off, the filtrate stirred with a mixture of 1.4 liters of petroleum ether and 0.7 liter of diethyl ether and the resulting product suction-filtered off. The filtered material is made into a paste with a mixture of ethanol (150 ml)/diethyl ether (150 ml)/petroleum ether (150 ml), suction-filtered off and dried under high vacuum at room temperature. The crude product is stirred with 250 ml of methylene chloride, the insoluble portion is separated off, the clear solution is evaporated off in a rotary evaporator at 45° and the remaining foam is chromatographed over 25 times the amount of silica gel. The fractions with methylene chloride/trifluoroethanol/water (7:4:0.2) are combined. 7β-{(2R,S)-2-[4-((2R)-2-amino-2-diphenylmethoxycarbonylamino)-phenyl]-2-sulphoacetylamino}-3-[(1-methyl-1H-tetrazol-5-yl)thiomethyl]-3-cephem-4-carboxylic acid diphenylmethyl ester is obtained therefrom. Mp. 173°-175° (with decomposition). CS (solvent: methyl acetate/ethanol (4:1)): $R_f=0.42$.

EXAMPLE 21

(a) 25 ml of trifluoroacetic acid are added to a solution, cooled to 0°, of 5.4 g (5.3 mmole) of 7β-{(2R)-2-BOC-amino-2-[3-((2R)-2-BOC-amino-2-diphenylmethoxycarbonylethoxycarbonylamino)phenyl]acetylamino}-3-methoxy-3-cephem-4-carboxylic acid diphenylmethyl ester and 5.4 ml of anisole in 30 ml of absolute methylene chloride and the mixture is stirred for 30 minutes with the exclusion of moisture. After adding 250 ml of petroleum ether/diethyl ether (1:1), the precipitate formed is filtered off, washed with diethyl ether and dried. The aqueous solution (35 ml) of the crude ditrifluoroacetate is extracted with ethyl acetate (3×20 ml), adjusted to a pH of 5 with 2N sodium hydroxide solution and 130 ml of isopropanol are added dropwise. The 7β-{(2R)-2-amino-2-[3-(2R)-2-amino-2-carboxyethoxycarbonylamino)phenyl]acetylamino}-3-methoxy-3-cephem-4-carboxylic acid obtained is recrystallised from 140 ml of water/isopropanol (1:3), extracted twice with a small amount of water to remove isopropanol and dried under a high vacuum. Mp. 170° (with decomposition). CS: $R_{f96}=0.1$; $[α_D=112\pm1°$ (c=1.17 in 0.1N HCl).

The starting material can be produced as follows:

(b) 6.2 ml of 20% phosgene in toluene are added to a solution, cooled to 0°, of 4.45 g (12 mmole) of (2R)-N-BOC-serine diphenylmethyl ester and 1.0 ml of absolute pyridine in 100 ml of absolute methylene chloride while stirring and with the exclusion of moisture, and the mixture is stirred for 3 hours at room temperature (solution A).

3.2 ml of bis(trimethylsilyl)acetamid are added, under nitrogen, to 3.2 g (12 mmole) of (2R)-2-BOC-amino-2-(3-amino)phenylacetic acid dissolved in 100 ml of absolute methylene chloride and the mixture is stirred for one hour at room temperature (solution B).

At 0° solution B is added dropwise to solution A over a period of 5 minutes, then 1.3 ml of N-methylmorpholine are added and the mixture is stirred for 30 minutes at 0° and for 3 hours at 25°. The solution is washed with iced water and saturated sodium chloride solution, dried over sodium sulphate and concentrated in a rotary evaporator. The crude product is purified over silica gel with diethyl ether as eluant, from which (2R)-2-BOC-amino-2-[3-(2R)-2-BOC-amino-2-diphenylmethoxycarbonylethoxycarbonylamino]phenylacetic acid is isolated in the form of a colourless amorphous powder. CS: $R_{f96}=0.9$.

(e) 0.67 ml (5.1 mmole) of chloroformic acid isobutyl ester is added to a solution, cooled to −20°, of 3.4 g (5.1 mmole) of (2R)-2-BOC-amino-2-[3-((2R)-2-BOC-amino-2-diphenylmethoxycarbonylethoxycarbonylamino)phenyl]acetic acid and 0.59 ml (5.1 mmole) of N-methylmorpholine in 150 ml of absolute methylene chloride while stirring and with the exclusion of moisture. In one portion 2.21 g (5.1 mmole) of 7β-amino-3-methoxy-3-cephem-4-carboxylic acid diphenylmethyl ester hydrochloride, then 0.57 ml of N-methylmorpholine are added at −10° to the so-obtainable mixed anhydride. After a reaction time of 2 hours at 0°, the solution is diluted with ethyl acetate (500 ml), washed with iced water and saturated sodium chloride solution, dried over sodium sulphate and concentrated in a rotary evaporator. The residue is purified over silica gel with diethyl ether as eluant, from which the 7β-{(2R)-2-BOC-amino-2-[3-((2R)-2-BOC-amino-2-diphenylmethoxycarbonylethoxycarbonylamino)phenyl]acetylamino}-3-methoxy-3-cephem-4-carboxylic acid diphenylmethyl ester, uniform according to thin layer chromatography, is isolated in the form of an amorphous product. CS (solvent: ethyl acetate): $R_f=0.60$; IR-spectrum in methylene chloride: characteristic bands at 3380, 1778, 1720, 1680, 1490 and 1160 cm$^{-1}$.

EXAMPLE 22

(a) 30 ml of trifluoroacetic acid are added to a solution, cooled to 0°, of 6.0 g (6.1 mmole) of 7β-{(2R,S)-2-hydroxy-2-[3-((2R)-2-BOC-amino-2-diphenylmethoxycarbonylethoxycarbonylamino)phenyl]acetylamino}-3-carbamoyloxymethyl-3-cephem-4-carboxylic acid diphenylmethyl ester and 6 ml of anisole in 30 ml of methylene chloride, with the exclusion of atmospheric moisture and while stirring. After 45 minutes 300 ml of petroleum ether/diethyl ether (1:1) are added at 0° over a period of approximately 30 minutes to the clear solution. The resulting trifluoroacetate is filtered off, washed with diethyl ether, dried for 30 minutes at 10 torr, and partially dissolved in 20 ml of water. The solution is adjusted to a pH of 6 by adding saturated aqueous sodium bicarbonate solution, and is extracted with ethyl acetate (5×15 ml). The slightly turbid aqueous phase is adjusted to a pH of 4 with 2N hydrochloric acid, filtered clear through Celite, and isopropanol is added. The precipitate is filtered off, to remove isopropanol dried twice under a high vacuum with 10 ml of water each time and the 7β-[(2R,S)-2-hydroxy-2-[3-((2R)-2-amino-2-carboxyethoxycarbonylamino)phenyl]acetylamino}-3-carbamoyloxymethyl-3-cephem-4-carboxylic acid sodium salt monohydrate is obtained in the form of a pale yellow powder. Mp. from 160° (with decomposition); $[\alpha]_D=126\pm 1°$ (c=0.89, in H$_2$O); CS $R_{f96}=0.14$.

The starting material can be produced as follows:

(b) 1.1 ml (10 mmole) of N-methylmorpholine are added at room temperature to a paste of 6.11 g (10.0 mmole) of 7β-amino-3-carbamoyloxymethyl-3-cephem-4-carboxylic acid diphenylmethyl ester p-toluenesulphonic acid salt in 100 ml of absolute tetrahydrofuran while stirring and with the exclusion of mositure, then after approximately 5 minutes 2.8 g (12 mmole) of 3-nitro-(R,S)-mandelic acid O-carboxyanhydride dissolved in 20 ml of absolute tetrahydrofuran are added at 0°. After a reaction time of 1 hour at 0° and 16 hours at room temperature the solvent is removed in a rotary evaporator. The residue, taken up in ethyl acetate (500 m), is washed with 2×50 ml iced water, saturated sodium bicarbonate solution and sodium chloride solution, dried over sodium sulphate and concentrated in a rotary evaporator. The crude 7β-[(2R,S)-2-hydroxy-2-(3-nitrophenyl)acetylamino]-3-carbamoyloxymethyl-3-cephem-4-carboxylic acid diphenylmethyl ester is purified over silica gel with diethyl ether/ethyl acetate (9:1) as eluant. CS (solvent: diethyl ether/ethyl acetate 1:1) $R_f=0.63$ and 0.74 (epimeric mixture); IR-spectrum in methylene chloride: characteristic bands at 3500, 3380, 1780, 1730, 1690, 1530 and 1350 cm$^{-1}$.

(c) A solution of 8 g (13.3 mmole) of 7β-[(2R,S)-2-hydroxy-2-(3-nitrophenyl)acetylamino]-3-carbamoyloxymethyl-3-cephem-4-carboxylic acid diphenylmethyl ester in 150 ml of ethyl acetate is hydrogenated in the presence of 4 g of palladium on activated carbon (10%). After removing the catalyst by filtration through Celite, the filtrate is concentrated in a rotary evaporator and the crude product is purified over silica gel with methylene chloride/ethyl acetate (1:1) as eluant. The fractions, uniform according to thin layer chromatography, containing the 7β-[(2R,S)-2-hydroxy-2-(3-aminophenyl)acetylamino]-3-carbamoyloxymethyl-3-cephem-4-carboxylic acid diphenylmethyl ester are combined and dried under high vacuum. CS (solvent: diethyl ether/ethyl acetate 9:1): $R_f=0.46$ and 0.51 (epimeric mixture).

(d) 4.2 ml of 20% phosgene in toluene are added at 0°, while stirring and with the exclusion of moisture, to a solution of 2.97 g (8 mmole) of (2R)-N-BOC-serine diphenylmethyl ester and 0.68 ml of pyridine in 80 ml of absolute methylene chloride, and the mixture is allowed to react for 1 hour at 0° (solution A).

2.2 ml (8.8 mmole) of bis-(trimethylsilyl)acetamide are added at room temperature, while stirring and with the exclusion of moisture, to a solution of 4.7 g (8 mmole) of 7β-[(2R,S)-2-hydroxy-2-(3-aminophenyl)acetylamino]-3-carbamoyloxymethyl-3-cephem-4-carboxylic acid diphenylmethyl ester in 10 ml of absolute methylene chloride, and the mixture is stirred for 1 hour (solution B).

Solution B, cooled to 0°, is added dropwise over a period of 5 minutes to solution A, and after adding 0.95 ml (8.8 mmole) of N-methylmorpholine the mixture is stirred for 30 minutes at 0° and for 2 hours at room temperature. The reaction mixture, diluted with 400 ml of ethyl acetate, is washed with iced water and saturated sodium chloride solution, dried of sodium sulphate and concentrated in a rotary evaporator. The foamy residue is purified over silica gel with diethyl ether as eluant, and yields the 7β-{(2R,S)-2-hydroxy-2-[3-((2R)-2-BOC-amino-2-diphenylmethoxycarbonylethoxycarbonylamino)phenyl]acetylamino}-3-carbamoyloxymethyl-3-cephem-4-carboxylic acid diphenylmethyl ester in the form of an amorphous powder.

CS (solvent: diethyl ether): $R_f=0.29$; IR-spectrum in methylene chloride: characteristic bands at 3380, 1780, 1730, 1690, 1490, 1200, 1155 and 1070 cm$^{-1}$.

EXAMPLE 23

(a) 25 ml of trifluoroacetic acid are added, with the exclusion of atmospheric moisture and while stirring, to a solution, cooled to 0° C., of 4.9 g (5.2 mmole) of 7β-{(2R,S)-2-hydroxy-2-[3-((2R)-2-BOC-amino-2-diphenylmethoxycarbonylethoxycarbonylamino)-phenyl]acetylamino}-3-methoxy-3-cephem-4-carboxylic acid diphenylmethyl ester and 5 ml of anisole in 25 ml of methylene chloride. After 30 minutes 200 ml of petroleum ether/diethyl ether (1:1) are added to the clear solution. The precipitating 7β-{(2R,S)-2-hydroxy-2-[3-((2R)-2-amino-2-carboxyethoxycarbonylamino)-phenyl]acetylamino}-3-methoxy-3-cephem-4-carboxylic acid trifluoroacetate is filtered off, washed with diethyl ether, dried under high vacuum. dissolved in 35 ml of water and extracted with ethyl acetate (3×20 ml). The aqueous phase is adjusted to a pH of 3 with 1N sodium hydroxide solution, and to purify the crude product, chromatography over an Amberlite XAD-2 column with water/isopropanol (9:1) as eluant is carried out. After removing the solvent in a rotary evaporator the 7β-{(2R,S)-2-hydroxy-2-[3-((2R)-2-amino-2-carboxyethoxycarbonylamino)phenyl]acetylamino}-3-methoxy-3-cephem-4-carboxylic acid is obtained in the form of the monohydrate. Mp. from 130° (with decomposition); $[\alpha]_D=124\pm1°$ (c=1.119, in 0.1N HCl); CS: $R_{f96}=0.18$.

The starting material can be obtained as follows:

(b) 150 ml of 20% phosgene solution in toluene are added to a solution of 29.55 g (0.15 mole) of 3-nitro-(R,S)-mandelic acid [manufacture cf. E. Adlarova, Collection Czech, Chem. Commun., 29, 97 (1964)] in 300 ml of absolute tetrahydrofuran, and the mixture is left to stand for 3 days at 25° in a closed flask. After removing the excess phosgene and the solvent with the exclusion of moisture in a rotary evaporator, the 3-nitro-(R,S)-mandelic acid O-carboxyanhydride obtained is dried under high vacuum. IR-spectrum in methylene chloride: characteristic bands at 1900, 1825, 1540, 1355, 1240, 1070 and 950 cm$^{-1}$.

(c) Under nitrogen, 6.66 ml (0.06 mole) of N-methylmorpholine and after 10 minutes a solution of 13.98 g (0.06 mole) of 3-nitro-(R,S)-mandelic acid O-carboxyanhydride in 150 ml of tetrahydrofuran, are added to a paste, cooled to 0°, of 25.98 g (0.06 mole) of 7β-amino-3-methoxy-3-cephem-4-carboxylic acid diphenylmethyl ester hydrochloride in 400 ml of absolute tetrahydrofuran. After a reaction time of 3 hours at room temperature the solvent is distilled off. The residue is taken up in ethyl acetate and extracted with water (2×150 ml), dilute sodium bicarbonate solution (2×150 ml) and saturated sodium chloride solution. The organic phase is dried over sodium sulphate and the solvent is evaporated off in a rotary evaporator at 30°.

The crude 7β-[(2R,S)-2-hydroxy-2-(3-nitrophenyl-)acetylamino]-3-methoxy-3-cephem-4-carboxylic acid diphenylmethyl ester obtained is purified over silica gel with diethyl ether/ethyl acetate (1:1) as eluant. CS (solvent: diethyl ether/ethyl acetate (1:1): $R_f=0.54$ and 0.65 (epimeric mixture). IR-spectrum in methylene chloride: characteristic bands at 3600, 1780, 1725, 1535, 1355, 1210 and 1050 cm$^{-1}$.

(d) A solution of 26 g (0.045 mole) of 7β-[(2R,S)-2-hydroxy-2-(3-nitrophenyl)acetylamino]-3-methoxy-3-cephem-4-carboxylic acid diphenylmethyl ester in 500 ml of ethyl acetate is hydrogenated in the presence of 13 g of palladium on activated carbon (10%). After removing the catalyst by filtration through Celite, the filrate is concentrated in a rotary evaporator and the crude product is purified over silica gel with diethyl ether/ethyl acetate as eluant. The fractions, uniform according to thin-layer chromatography, of 7β-[(2R,S)-2-hydroxy-2-(3-aminophenyl)acetylamino]-3-methoxy-3-cephem-4-carboxylic acid diphenylmethyl ester are combined and dried under high vacuum. CS (solvent: ethyl acetate): $R_f=0.46$; IR-spectrum in methylene chloride: characteristic bands at 3380, 1780, 1720 and 1220 cm$^{-1}$.

(e) 6.2 ml of 20% phosgene in toluene are added to a solution of 4.45 g (12 mmole) of (2R)-N-BOC-serine diphenylmethyl ester and 1.0 ml of pyridine in 100 ml of absolute methylene chloride at 0° while stirring and the mixture is further stirred for 1 hour at 0° (solution A).

3.3 ml of bis-(trimethylsilyl)acetamide are added to a solution of 6.55 g (12 mmole) of 7β-[(2R,S)-2-hydroxy-2-(3-aminophenyl)acetylamino]-3-methoxy-3-cephem-4-carboxylic acid diphenylmethyl ester in 100 ml of absolute methylene chloride at room temperature while stirring and with the exclusion of moisture, and the mixture is stirred for one hour (solution B).

Solution B is added dropwise over a period of 5 minutes to solution A at 0°, then 1.3 ml (12 mmole) of N-methylmorpholine are added and the mixture is stirred for 30 minutes at 0° and for 1 hour at 25°.

The reaction mixture, diluted with ethyl acetate (600 ml), is extracted with 3×150 ml in each case of iced water, dilute hydrochloric acid and saturated sodium chloride solution. The organic phase is dried over sodium sulphate and freed of solvent in a rotary evaporator. The crude product obtained is purified over silica gel with diethyl ether/ethyl acetate (9:1) as eluant. 7β-{(2R,S)-2-hydroxy-2-[3-((2R)-2-BOC-amino-2-diphenylmethoxycarbonylethoxycarbonylamino)-phenyl]acetylamino}-3-methoxy-3-cephem-4-carboxylic acid diphenylmethyl ester, uniform according to thin-layer chromatography, is obtained, CS (solvent: diethyl ether/ethyl acetate 1:1): $R_f=0.44$; IR-spectrum in methylene chloride: characteristic bands at 3400, 1780, 1735, 1720, 1600, 1495, 1205 and 1160 cm$^{-1}$.

EXAMPLE 24

(a) 0.5 ml of trifluoroacetic acid is added at 0° to a solution of 90 mg of 7β-[5-((2R)-2-BOC-amino-2-diphenylmethoxycarbonylethoxycarbonylaminomethyl)thien-2-ylacetamido]-7α-methoxy-3-(1-methyl-1H-tetrazol-5-ylthiomethyl)-3-cephem-4-carboxylic acid in 0.5 ml of methylene chloride and the solution is stirred for 45 minutes at 0°. The crude product is precipitated with 5 ml of diethyl ether/hexane (1:1) in the form of trifluoroacetic acid salt and this is digested with methanol/pyridine (9:1). In this manner 7β-[5-((2R)-2-amino-2-carboxyethoxycarbonylaminomethyl)thien-2-ylacetamido]-7α-methoxy-3-(1-methyl-1H-1,2,3,4-tetrazol-5-ylthiomethyl)-3-cephem-4-carboxylic acid is obtained. CS: $R_{f52A}=0.24$ (running distance with intermediate drying: 3 times 10 cm).

The starting compound can be produced as follows:

(b) A solution of 445 mg of (R)-N-BOC-serine diphenylmethyl ester and 95 mg of pyridine in 3 ml of methylene chloride is added dropwise at 0° to 5° to 0.6 ml of a 20% solution of phosgene in toluene and the mixture is then stirred for 1 hour at this temperature. The mixture is concentrated by evaporation in vacuo, the residue is dissolved in 3 ml of tetrahydrofuran and this solution is added dropwise at 0° to 5° to a solution, adjusted to a pH of 9 by means of a titrator (0.1N sodium hydroxide solution), of 510 mg of 7β-(5-aminomethylthien-2-yl-acetamido)-7α-methoxy-3-(1-methyl-1H-tetrazol-5-ylthiomethyl)-3-cephem-4-carboxylic acid in 4 ml of water and 2 ml of tetrahydrofuran. The mixture is stirred at a pH of 9 (maintained constant by titrator) for 45 minutes at 0° to 5° and for 30 minutes at 20°. The mixture is added to 50 ml of 0.5 molar potassium dihydrogen phosphate solution, the pH is adjusted to 6.1 and the organic solvents are evaporated off in vacuo. The remaining aqueous phase is extracted 3 times with 50 ml of ethyl acetate each time. The extract, dried over sodium sulphate, is concentrated by evaporation and the residue is digested with diethyl ether. A crude product is obtained which is chromatographed over 10 g of silica gel. The fractions eluted with acetone/methanol (1:1) contain the pure 7β-[5-((2R)-BOC-amino-2-diphenylmethoxycarbonylethoxycarbonylaminomethyl)thien-2-ylacetamido]-7α-methoxy-3-(1-methyl-1H-tetrazol-5-ylthiomethyl)-3-cephem-4-carboxylic acid. CS: $R_{f52A}=0.45$.

EXAMPLE 25

5.29 g (9.9 mmole) of 7β-[4-((2R)-2-amino-2-carboxyethoxycarbonylamino)phenylacetamido]cephalosporanic acid sodium salt are added to a solution of a temperature of 70° of 16.3 g of sodium iodide, 1.62 g (13.3 mmole) of isonicotinic acid amide and 0.59 ml (10.3 mmole) of glacial acetic acid in 7.7 ml of water, and the mixture is stirred for 1½ hours at 70° under a nitrogen atmosphere. The warm solution is added dropwise to 200 ml of cold acetone and after 30 minutes at −20° the precipitate is filtered off. The residue is digested twice with 70 ml of methanol each time, and the insoluble portion is filtered off. A solution of this crude product in 17 ml of water is decolorised with 160 mg of activated carbon, filtered clear and the filtrate is added dropwise to 870 ml of ethanol while stirring. After stirring for 45 minutes at 0° the 7β-[4-((2R)-2-amino-2-carboxyethoxycarbonylamino)phenylacetamido]-3-(4-carbamoylpyridiniomethyl)-3-cephem-4-carboxylate (betaine) is filtered off. CS: $R_{f101}=0.18$.

EXAMPLE 26

(a) A mixture of 8.0 g of 7β-{2-[4-((4R)-4-BOC-amino-4-tert.-butoxycarbonylbutyrylamino)phenyl]acetylamino}-3-[(1-methyl-1H-tetrazol-5-yl)thiomethyl]-3-cephem-4-carboxylic acid diphenylmethyl ester, 3.0 ml of anisole, 8.0 ml of methylene chloride and 80 ml of trifluoroacetic acid is stirred for 35 minutes at room temperature with the exclusion of atmospheric moisture. The suspension obtained is poured onto an ice-cold mixture of petroleum ether (1 liter) and diethyl ether (500 ml), the resulting trifluoroacetic is suction-filtered off, washed with diethyl ether and dried at room temperature under a high vacuum.

7β-{2-[4-((4R)-4-amino-4-carboxybutyrylamino)-phenyl]acetylamino}-3-[1-methyl-1H-tetrazol-5-yl)thiomethyl]-3-cephem-4-carboxylic acid sodium salt is obtained from the trifluoroacetic according to the process of Example 1. Mp. from 200° (with decomposition). CS: $R_{f52A}=0.06$, $R_{f101}=0.28$, $R_{f101A}=0.28$.

The starting material can be produced as follows:

(b) A mixture of 10.5 g of (2R)-glutamic acid γ-benzyl ester (produced according to the process of R. L. Prestidge et. al, J.O.C. 40, 3287 (1975)), 90 ml of dioxan, 30 ml of water and 13 ml of di-tert.-butyl dicarbonate is stirred at room temperature, and the pH of the reaction mixture is maintained between 7 and 7.6 by the dropwise addition of 1N sodium hydroxide solution. After 2 hours the clear solution is concentrated to approximately 50 ml in a rotary evaporator at 50° and extracted with ethyl acetate. The aqueous phase is separated off, acidified with 20% citric acid solution (pH 3) and extracted 3 times with ethyl acetate. The organic extracts are combined, washed once with salt water solution, dried over sodium sulphate and the solvent is evaporated off in a rotary evaporator at 45°. By mixing with petroleum ether and cooling, the (2R)-N-BOC-glutamic acid γ-benzyl ester solidifies. Mp. 50°–58° (with decomposition). $[\alpha]_D=-13\pm1°$ (c+3.11 in chloroform).

The oily (2R)-N-BOC-glutamic acid (γ-benzyl ester)-α-tert.-butyl ester is obtained from (2R)-N-BOC-glutamic acid γ-benzyl ester by reacting with O-tert.-butylisourea in methylene chloride [E. Vowinkel, Chem. Ber. 100, 16 (1967)]. The crude product is purified by chromatography over 20 times the amount of silica gel. CS (solvent: toluene/ethyl acetate/chloroform (3:1:1)): $R_f=0.58$ (developed with ninhydrin); $[\alpha]_D=8\pm1°$ (c=3.17 in chloroform).

(c) A solution of 28 g of (2R)-N-BOC-glutamic acid (γ-benzyl ester)-α-tert.-butyl ester in 250 ml of ethyl acetate is hydrogenated in the presence of 4.0 g of palladium on activated carbon (10%). After approximately 4 hours the calculated amount of hydrogen has been absorbed. The catalyst is filtered off, washed with ethyl acetate, the filtrate is concentrated in a rotary evaporator at 45° and (2R)-N-BOC-glutamic acid α-tert.-butyl ester is crystallised by adding petroleum ether. Mp. 109°–112° (with decomposition). $[\alpha]_D=-5\pm1°$ (c=2.66 in chloroform).

(d) A solution of 9.0 g of (2R)-N-BOC-glutamic acid α-tert.-butyl ester and 7.50 g of 4-aminophenylacetic acid benzyl ester in 80 ml of tetrahydrofuran is cooled with an ice bath to +5°, a solution of 6.50 g of N,N′-dicyclohexyl carbodiimide in 20 ml of tetrahydrofuran is added dropwise over a period of 20 minutes while stirring and cooling, then the ice bah is removed and the reaction mixture is stirred at room temperature. After a reaction time of 3 hours 3.0 g of solid N,N′-dicyclohexyl carbodiimide is added to the reaction mixture. After stirring for a total of 7 hours the suspension is suction-filtered off, the filtered material is washed with ethyl acetate, a large amount of ethyl acetate is added to the filtrate and the tetrahydrofuran is removed by concentrating in a rotary evaporator at 45°. The solution obtained is diluted with ethyl acetate and washed in succession with water, 1N sodium bicarbonate solution and water. The organic phase is dried over sodium sulphate and concentrated by evaporation in a rotary evaporator at 45°. The crude product is purified by filtering over 10 times the amount of silica gel. The fractions with methylene chloride/methyl acetate (10:0.5) as eluant are combined. The 4-((4R)-4-BOC-amino-4-tert.-butyoxycarbonylbutyrylamino)phenylacetic acid benzyl ester obtained is recrystallised from a mixture of ethyl acetate and petroleum ether. Mp. 101°–104° (with decomposition).

(e) A solution of 20.0 g of 4-((4R)-4-BOC-amino-4-tert.-butoxycarbonylbutyrylamino)phenylacetic acid benzyl ester in a mixture of ethyl acetate (150 ml) and ethanol (150 ml) is hydrogenated at room temperature in the presence of 5.0 g of palladium on activated carbon (10%). After approximately 5 hours the calculated amount of hydrogen has been absorbed. The catalyst is filtered off, washed with a mixture of ethyl acetate and ethanol (1:1) and the filtrate is concentrated by evaporation in a rotary evaporator at 45°. The 4-((4R)-4-BOC-amino-4-tert.-butoxycarbonylbutyrylamino)phenylacetic acid is precipitated by mixing with petroleum ether. Mp. 129°-136° (with decomposition); $[\alpha]_D = +10 \pm 1°$ (c=3.04, in methanol).

(f) A solution of 9.5 g of 7β-amino-3-[(1-methyl-1H-tetrazol-5-yl)thiomethyl]-3-cephem-4-carboxylic acid diphenylmethyl ester and 8.0 g of 4-((4R)-4-BOC-amino-4-tert.-butoxycarbonylbutyrylamino)phenylacetic acid in a mixture of 50 ml of tetrahydrofuran and 15 ml of N,N-dimethylformamide is reacted with a solution of 4.0 g of N,N′-dicyclohexyl carbodiimide in 20 ml of tetrahydrofuran and 2.0 g of solid N,N′-dicyclohexyl carbodiimide in accordance with the process of Example 1, and the reaction mixture is worked up. On concentrating the ethyl acetate solution the crystalline 7β-{2-[4-((4R)-4-BOC-amino-4-tert.-butoxycarbonylbutyrylamino)phenyl]acetamido}-3-[(1-methyl-1H-tetrazol-5-yl)thiomethyl]-3-cephem-4-carboxylic acid diphenylmethyl ester is precipitated. Mp. 172°-178° (with decomposition). CS (solvent: toluene-/ethyl acetate/methylene chloride/ethanol (16:16:16:1): $R_f = 0.32$.

EXAMPLE 27

In a manner analogous to that described in the above Examples the following compounds may be produced from the corresponding compounds in which the carboxyl groups, the amino groups and optionally the hydroxyl groups are present in protected form:

7β-{2-[4-((4R)-4-amino-4-carboxybutyrylamino)-phenyl]acetylamino}-3-carbamoyloxymethyl-3-cephem-4-carboxylic acid;

7β-{(R,S)-2-[4-((2R)-2-amino-2-carboxyethoxycarbonylamino)phenyl]-2-formyloxyacetylamino}-3-[(1-methyl-1H-tetrazol-5-yl)-thiomethyl]-3-cephem-4-carboxylic acid;

7β-{(2R,S)-2-[4-((2R)-2-amino-2-carboxyethoxycarbonylamino)phenyl]-2-formyloxyacetylamino}-3-carbamoyloxymethyl-3-cephem-4-carboxylic acid;

7β-{(2-[4-((2R)-2-amino-2-carboxyethoxycarbonylamino)phenyl]-2-syn-methoxyiminoacetylamino}-3-[(1-methyl-1H-tetrazol-5-yl)-thiomethyl]-3-cephem-4-carboxylic acid;

7β-{2-[4-((2R)-2-amino-2-carboxyethoxycarbonylamino)phenyl]-2-syn-methoxyiminoacetylamino}-3-carbamoyloxymethyl-3-cephem-4-carboxylic acid;

7β-{2-[4-((2R)-2-amino-2-carboxyethoxycarbonylamino)phenyl]acetylamino}-3-[1-(2-dimethylaminoethyl)-1H-tetrazol-5-yl]thiomethyl]-3-cephem-4-carboxylic acid;

7β-{2-[4-((2R)-2-amino-2-carboxyethoxycarbonylamino)phenyl]acetylamino}-3-[(1-carboxymethyl-1H-tetrazol-5-yl)thiomethyl]-3-cephem-4-carboxylic acid;

7β-{2-[4-((2R)-2-amino-2-carboxyethoxycarbonylamino)phenyl]acetylamino}-3-[(1-sulphomethyl-1H-tetrazol-5-yl)thiomethyl]-3-cephem-4-carboxylic acid;

7β-{(2R,S)-2-[4-((2R)-2-amino-2-carboxyethoxycarbonylamino)phenyl]-2-hydroxyacetylamino}-3-[(1-carboxymethyl-1H-tetrazol-5-yl)thiomethyl]-3-cephem-4-carboxylic acid;

7α-methoxy-7β-{2-[4-((2R)-2-amino-2-carboxyethoxycarbonylamino)phenyl]acetylamino}-3-acetoxymethyl-3-cephem-4-carboxylic acid;

7α-methoxy-7β-{2-[4-((2R)-2-amino-2-carboxyethoxycarbonylamino)phenyl]-acetylamino}-3-carbamoyloxymethyl-3-cephem-4-carboxylic acid;

7α-methoxy-7β-{(2R,S)-2-[4-((2R)-2-amino-2-carboxyethoxycarbonylamino)phenyl]-2-hydroxyacetylamino}-3-carbamoyloxymethyl-3-cephem-4-carboxylic acid.

7α-methoxy-7β-{(2R,S)-2-[4-((2R)-2-amino-2-carboxyethoxycarbonylamino)phenyl]-2-hydroxyacetylamino}-3-[(1-methyl-1H-tetrazol-5-yl)thiomethyl]-3-cephem-4-carboxylic acid;

and the corresponding (4S)-4-amino-4-carboxybutyrylamino, (2S)-2-amino-2-carboxyethoxycarbonylamino, and (2R)-2-hydroxyacetylamino, (2S)-2-hydroxyacetylamino, (2R)-2-formyloxyacetylamino and (2S)-2-formyloxyacetylamino compounds, and corresponding salts, for example, sodium salts, thereof.

EXAMPLE 28

Dry ampoules or phials, containing 0.5 g of 7β-{2-[4-((2R)-2-amino-2-carboxyethoxycarbonylamino)phenyl]acetylamino}-3-[(1-methyl-1H-tetrazol-5-yl)thiomethyl]-3-cephem-4-carboxylic acid sodium salt, are produced as follows:

| | |
|---|---|
| 7β-{2-[4-((2R)-2-amino-2-carboxyethoxycarbonyl-amino)phenyl]acetylamino}-3-[(1-methyl-1H—tetrazol-5-yl)thiomethyl]-3-cephem-4-carboxylic acid sodium salt | 0.5 g |
| mannitol | 0.05 g |

A sterile aqueous solution of 7β-{2-[4-((2R)-2-amino-2-carboxyethoxycarbonylamino)phenyl]acetylamino}-3-[(1-methyl-1H-tetrazol-5-yl)thiomethyl]-3-cephem-4-carboxylic acid sodium salt and of mannitol is sealed under aspectic conditions in 5 ml ampoules or 5 ml phials and examined.

EXAMPLE 29

Dry ampoules or phials, containing 0.5 g of 7β-{(2R)-2-[4-((2R)-2-amino-2-carboxyethoxycarbonylamino)-phenyl]-2-hydroxyacetylamino}-3-[(1-methyl-1H-tetrazol-5-yl)thiomethyl]-3-cephem-4-carboxylic acid sodium salt, are produced as follows:

| | |
|---|---|
| 7β-{(2R)-2-[4-((2R)-2-amino-2-carboxyethoxy-carbonylamino)phenyl]-2-hydroxyacetylamino}-3-[(1-methyl-1H—tetrazol-5-yl)thiomethyl]-3-cephem-4-carboxylic acid sodium salt | 0.5 g |
| mannitol | 0.05 g |

A sterile aqueous solution of the 7β-{(2R)-2-[4-((2R)-2-amino-2-carboxyethoxycarbonylamino)phenyl]-2-hydroxyacetylamino}-3-[(1-methyl-1H-tetrazol-5-yl)thiomethyl]-3-cephem-4-carboxylic acid sodium salt and mannitol is sealed under aseptic conditions in 5 ml ampoules or 5 ml phials and examined.

We claim:

1. Compounds of the formula $$\text{HOOC}-\underset{\underset{\text{NH}_2}{|}}{\text{CH}}-(C_nH_{2n})-X-W-NH-(C_mH_{2m})-A-\underset{\underset{Z}{|}}{\overset{\overset{Y}{|}}{C}}-\overset{O}{\overset{\|}{C}}-OH, \quad (III)$$

in which n represent an integer from 1 to 4, m represents 0 or 1,

X represents oxygen, sulphur or the —NH— group,

W represents a —CO—, —CO—NHSO$_2$— or SO$_2$—NHSO$_2$— group, or

X—W together represent a —CO— or —CO—NHSO$_2$—group,

A represents phenylene, thienylene or furylene, or such groups substituted by lower alkyl, lower alkoxy and/or halogen, Y represents hydrogen, hydroxyl, formyloxy, amino or sulpho, Z represents hydrogen, or Y and Z together represent an oxo group or an =N—OR° group in which R° represents hydrogen, lower alkyl, or lower alkyl substituted by lower alkoxy, halogen, hydroxy, lower alkanoyloxy, sulpho, carboxy or lower alkoxycarbonyl, and in which the aminocarboxylic acid grouping HOOC—CH(NH$_2$)— and further functional groups optionally present in the grouping —A—C(Y)(Z)— are protected by an eliminatable protecting group, their mixed anhydrides with a hydrohalic acid, hydrazoic, phosphoric, phosphorous, sulfuric or hydrocyanic acid, a lower alkanecarboxylic acid optionally substituted by halogen, a lower alkyl semi-ester of carbonic acid, or a sulfonic acid, and their lower alkenol-, 4-nitrophenyl-, 2,4-dinitrophenyl-, benzotriazole-, succinylimino- or phthalylimino ester.

2. Compounds of formula III according to claim 1, in which the —(CH$_2$)— group is unbranched and the indices n and m have the meanings given in claim 1, X represents oxygen or the —NH— groups, W represents the —CO— or —CO—NHSO$_2$ group, or X—W together represent the —CO or —CO—NHSO$_2$— group, A represents p- or m-phenylene, 2,5-thienylene or 2,5-furylene, Y represents hydrogen, hydroxyl, amino or sulpho, Z represents hydrogen, or Y and Z together represent a =N—O—R° group, in which R° is hydrogen or methyl, and in which the aminocarboxylic acid grouping HOOC—CH(NH$_2$)— and further functional groups optionally present in the grouping —A—C(Y)(Z)— are protected by an eliminatable protecting group, their mixed anhydride with hydrogen chlorine, a lower alkane carboxylic acid optionally substituted by halogen, a lower alkyl semi-ester of carbonic acid, or a sulfonic acid, and their lower alkenol-, 4-nitrophenyl-, 2,4-dinitrophenyl or phthalylimino ester.

3. Compounds of formula I according to claim 1, wherein the —(CH$_2$)— Group is unbranched and the indices n and m have the meanings given in claim 1, X represents oxygen or the —NH—group, W represents the —CO— or —CONHSO$_2$— group, or X—W together represent the —CO— or —CONHSO$_2$— group, A represents p- or m-phenylene, or, if m is 1, A also represents 2,5-thienylene or 2,5-furylene, Y represents hydrogen, hydroxyl, amino or sulpho, Z represents hydrogen, or Y and Z together represent a =N—O—R° group in which R° is hydrogen or methyl, and in which the aminocarboxylic acid grouping HOOC—CH(NH$_2$)— and further functional groups optionally present in the grouping —A—C(Y)(Z)— are protected by an eliminatable protecting group, their mixed anhydrides with hydrogen chloride, a lower alkanecarboxylic acid optionally substituted by halogen, a lower alkyl semi-ester of carbonic acid, or a sulfonic acid, and their lower alkenol-, 4-nitrophenyl, 2,4-dinitrophenyl or phthalymino ester.

4. 4-((2R)-2-BOC-amino-2-tert.-butoxy-carbonylethoxycarbonylamino)phenylacetic acid according to claim 2.

5. 4-((2R)-2-BOC-amino-2-diphenylmethoxy-carbonylethoxycarbonylamino)phenylacetic acid according to claim 2.

6. 4-((5R,S)-5-tert.-butoxycarbonylpentylaminocarbonylamino)phenylacetic acid according to claim 2.

7. 4-((3R)-3-BOC-amino-3-tert.-butoxycarbonylpropionylamino)phenylacetic acid according to claim 2.

8. 2-[5-((2R)-2-BOC-amino-2-diphenylmethoxycarbonylethoxycarbonylaminomethyl)-2-furyl]-2-syn-methoxyiminoacetic acid according to claim 2.

9. 2-[5-((2R)-2-BOC-amino-2-diphenylmethoxycarbonylethoxycarbonylaminomethyl)-2-thienyl]-2-syn-methoxyiminoacetic acid according to claim 2.

10. 2-[4-((2R)-2-BOC-amino-2-diphenylmethoxycarbonylethoxycarbonylaminosulphonylamino)-phenyl]-acetic acid according to claim 2.

11. (αR,S)-4-((2R)-2-BOC-amino-2-tert.-butoxycarbonylethoxycarbonylamino)-α-(2,2,2-trichloroethoxycarbonyloxy) phenylacetic acid according to claim 1.

12. (R)-4-((2R)-2-BOC-amino-2-diphenylmethoxycarbonylethoxycarbonylamino)mandelic acid according to claim 1.

13. (αR,S)-4-((2R)-2-BOC-amino-2-diphenylmethoxycarbonylethoxycarbonylamino)-α-sulphophenylacetic acid according to claim 1.

14. (2R)-2-BOC-amino-2-[3-(2R)-2-BOC-amino-2-diphenylmethoxycarbonylethoxycarbonylamino]-phenylacetic acid according to claim 1.

15. 4-((4R)-4-BOC-amino-4-tert.-butoxycarbonylbutyrylamino)phenylacetic acid according to claim 1.

* * * * *

UNITED STATES PATENT AND TRADEMARK OFFICE
CERTIFICATE OF CORRECTION

PATENT NO.  : 4,467,101

DATED       : August 21, 1984

INVENTOR(S) : Karoly Kocsis et al

It is certified that error appears in the above-identified patent and that said Letters Patent is hereby corrected as shown below:

| | |
|---|---|
| 1st page, under "U.S. Patent Documents" | 2nd line, delete "Brever" and substitute --Breuer-- |
| Col. 5, line 20 | Delete "pyridimidinylthio" and substitute --pyrimidinylthio-- |
| Col. 6, line 60 | Delete "butysilyl" and substitute --butylsilyl-- |
| Col. 7, line 53 | After "substituted" insert --phenyl-- |
| Col. 9, line 1 | Delete "alkyleneaminea" and substitute --alkyleneamines-- |
| Col. 18, line 32 | Delete "reacting" and substitute --treating-- |
| Col. 22, line 62 | After "and" insert --of-- |
| Col. 31, line 5 | After "CS: $R_f$" delete "$25A$" and substitute --$52A$-- |
| Col. 31, line 62 | After "tetrahydrofuran" insert --,-- |
| Col. 35, line 46 | After "-$N^2$" insert -- - -- and after "-$N^6$" insert -- - -- |

UNITED STATES PATENT AND TRADEMARK OFFICE
CERTIFICATE OF CORRECTION

PATENT NO. : 4,467,101

DATED : August 21, 1984

INVENTOR(S) : Karoly Kocsis et al

It is certified that error appears in the above-identified patent and that said Letters Patent is hereby corrected as shown below:

| | |
|---|---|
| Col. 38, line 51 | Delete "tolune" and substitute --toluene-- |
| Col. 41, line 42 | Delete "5.86" and substitute --5.84-- |
| Col. 43, line 26 | Delete "carred" and substitute --carried-- |
| Col. 43, line 36 | After "CS:R" delete "$_F$" and --$_f$-- |
| Col. 43, line 56 | Delete "was" and substitute --are-- |
| Col. 46, line 59 | After "1" insert --hour-- |
| Col. 47, line 44 | After "syn" insert -- - -- |
| Col. 50, line 32 and Col. 51, line 20 | End of line after "BO" insert -- - -- |
| Col. 51, line 27 | After "$R_f=$" delete "0.19" and substitute --0.49-- |
| Col. 52, line 58 | Delete "methyhlene" and substitute --methylene-- |
| Col. 54, line 29 | Delete "ince" and substitute --ice-- |
| Col. 57, line 1 | Delete "acetamid" and substitute --acetamide-- |
| Col. 57, line 18 | Delete "(e) and substitute --(c)-- |
| Col. 58, line 10 | Delete "mositure" and substitute --moisture-- |
| Col. 58, line 17 | Delete "m)" and substitute --ml)-- |

UNITED STATES PATENT AND TRADEMARK OFFICE
CERTIFICATE OF CORRECTION

PATENT NO. : 4,467,101

DATED : August 21, 1984

INVENTOR(S) : Karoly Kocsis et al

It is certified that error appears in the above-identified patent and that said Letters Patent is hereby corrected as shown below:

Col. 60, line 8      Delete "filrate" and substitute --filtrate--

Col. 64, line 54      Insert --Composition for 1 ampoule or phial)--

Signed and Sealed this

Fourth Day of June 1985

[SEAL]

Attest:

DONALD J. QUIGG

Attesting Officer      Acting Commissioner of Patents and Trademarks